US011974497B2

(12) United States Patent
Koo et al.

(10) Patent No.: US 11,974,497 B2
(45) Date of Patent: Apr. 30, 2024

(54) COMPOUND AND ORGANIC ELECTRONIC ELEMENT COMPRISING SAME

(71) Applicant: LG CHEM, LTD., Seoul (KR)

(72) Inventors: Ki Dong Koo, Daejeon (KR); Hyunseok Jeong, Daejeon (KR); Kongkyeom Kim, Daejeon (KR); Younghee Lee, Daejeon (KR); Woochul Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 714 days.

(21) Appl. No.: 16/308,231

(22) PCT Filed: Jul. 3, 2017

(86) PCT No.: PCT/KR2017/007022
§ 371 (c)(1),
(2) Date: Dec. 7, 2018

(87) PCT Pub. No.: WO2018/004315
PCT Pub. Date: Jan. 4, 2018

(65) Prior Publication Data

US 2019/0198769 A1 Jun. 27, 2019

(30) Foreign Application Priority Data

Jul. 1, 2016 (KR) ........................ 10-2016-0083592

(51) Int. Cl.
*H10K 85/60* (2023.01)
*C07D 307/91* (2006.01)
(Continued)

(52) U.S. Cl.
CPC ......... *H10K 85/636* (2023.02); *C07D 307/91* (2013.01); *C07D 471/00* (2013.01); (Continued)

(58) Field of Classification Search
None
See application file for complete search history.

(56) References Cited

U.S. PATENT DOCUMENTS

2002/0121860 A1* 9/2002 Seo ............................... 313/506
2004/0251816 A1 12/2004 Leo et al.
(Continued)

FOREIGN PATENT DOCUMENTS

CN 106397398 2/2017
EP 2796529 A1 10/2014
(Continued)

OTHER PUBLICATIONS

Zuoquan Jiang et al. "Multifunctional Fluorene-Based Oligomers with Novel Spiro-Annulated Triarylamine: Efficient, Stable Deep-Blue Electroluminescence, Good Hole Injection, and Transporting Materials with Very High Tg", Adv. Func. Mater. 2009, vol. 19, p. 3987-3995 (Year: 2009).*
(Continued)

*Primary Examiner* — Dylan C Kershner
*Assistant Examiner* — Seokmin Jeon
(74) *Attorney, Agent, or Firm* — BRYAN CAVE LEIGHTON PAISNER LLP

(57) ABSTRACT

A compound of Chemical Formula 4 or 5:

Chemical Formula 4

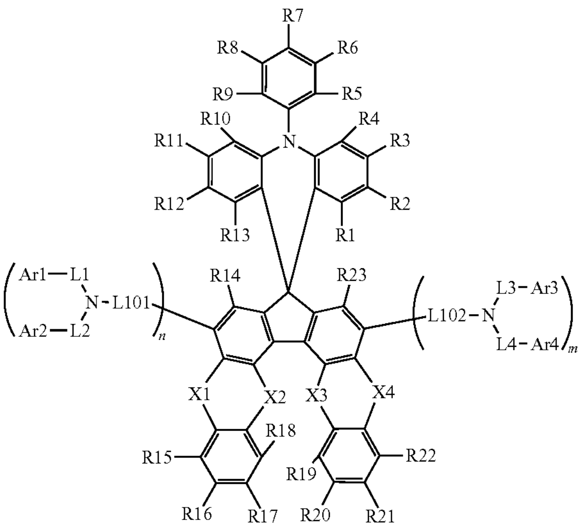

Chemical Formula 5

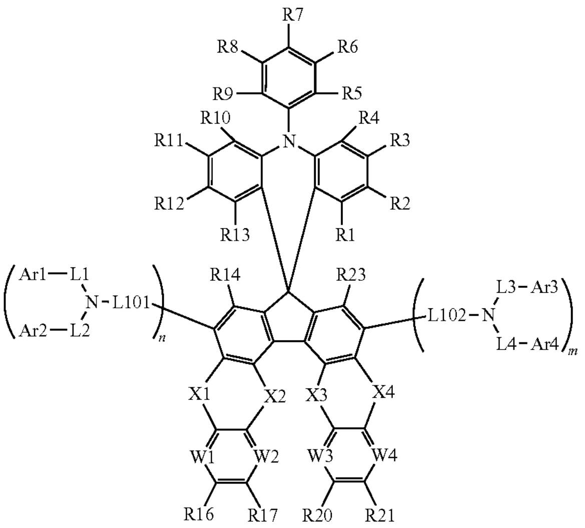

wherein: one of X1 and X2 is a direct bond, and the other is O, S, or CY1Y2, one of X3 and X4 is a direct bond, and
(Continued)

the other is O, S, or CY3Y4, W1 to W4 are each independently N or CRa, and one or more of W1 to W4 are N, Y1 to Y4 are the same as or different from each other, and are each independently an alkyl group having 1 to 20 carbon atoms, and the other substituents are as defined in the specification; and an organic light emitting device comprising the same. The compound can lower the driving voltage, improve the light efficiency, and enhance service life characteristics of the device due to thermal stability of the compound.

12 Claims, 3 Drawing Sheets

(51) Int. Cl.

| | |
|---|---|
| ***C07D 471/00*** | (2006.01) |
| ***C07D 491/147*** | (2006.01) |
| ***C07D 491/20*** | (2006.01) |
| ***C07D 491/22*** | (2006.01) |
| ***C07D 495/14*** | (2006.01) |
| ***C07D 495/20*** | (2006.01) |
| ***C07D 495/22*** | (2006.01) |
| ***C07F 7/08*** | (2006.01) |
| ***C09K 11/06*** | (2006.01) |
| ***H10K 50/00*** | (2023.01) |
| ***H10K 50/11*** | (2023.01) |
| ***H10K 85/40*** | (2023.01) |
| ***H10K 99/00*** | (2023.01) |

(52) U.S. Cl.

CPC ....... *C07D 491/147* (2013.01); *C07D 491/20* (2013.01); *C07D 491/22* (2013.01); *C07D 495/14* (2013.01); *C07D 495/20* (2013.01); *C07D 495/22* (2013.01); *C07F 7/0812* (2013.01); *C09K 11/06* (2013.01); *H10K 50/00* (2023.02); *H10K 85/40* (2023.02); *H10K 99/00* (2023.02); *H10K 50/11* (2023.02); *H10K 85/654* (2023.02); *H10K 85/6572* (2023.02); *H10K 85/6574* (2023.02)

(56) References Cited

U.S. PATENT DOCUMENTS

| | | | | |
|---|---|---|---|---|
| 2007/0247059 | A1* | 10/2007 | Cho | 313/499 |
| 2008/0303434 | A1 | 12/2008 | Cho et al. | |
| 2010/0289008 | A1 | 11/2010 | Jang et al. | |
| 2011/0278549 | A1 | 11/2011 | Kim et al. | |
| 2015/0065730 | A1* | 3/2015 | Montenegro | H01L 51/0058 548/440 |
| 2016/0204355 | A1* | 7/2016 | Kim | H01L 51/0061 |
| 2017/0062729 | A1* | 3/2017 | Cha | H01L 51/0061 |

FOREIGN PATENT DOCUMENTS

| | | | |
|---|---|---|---|
| IN | 280588 | | 4/2007 |
| JP | 2008-510800 | A | 4/2008 |
| JP | 2008-510801 | A | 4/2008 |
| JP | 2009-530809 | A | 8/2009 |
| JP | 2013-510848 | A | 3/2013 |
| KR | 10-2006-0051613 | A | 5/2006 |
| KR | 10-2007-0033383 | A | 3/2007 |
| KR | 10-2012-0135501 | A | 12/2012 |
| KR | 10-2014-0045153 | A | 4/2014 |
| KR | 10-1429035 | B1 | 8/2014 |
| KR | 10-2015-0030309 | | 3/2015 |
| KR | 10-2015-0034612 | A | 4/2015 |
| KR | 10-2016-0064027 | A | 6/2016 |
| WO | 2003/012890 | A2 | 2/2003 |
| WO | 2006/033564 | | 3/2006 |
| WO | 2006/033564 | A1 | 3/2006 |
| WO | 2006/080640 | | 8/2006 |
| WO | 2007/105906 | | 9/2007 |

OTHER PUBLICATIONS

Shou-Cheng Dong et al. “Spiro-annulated triarylamine-based hosts incorporating dibenzothiophene for highly efficient single-emitting layer white phosphorescent organic light-emitting diodes”, J. Mater. Chem. C, 2013, vol. 1, p. 6575-6584 (Year: 2013).*

Cong Fan et al. “Tetraphenylsilane derivatives spiro-annulated by triphenylamine/carbazole with enhanced HOMO energy levels and glass transition temperatures without lowering triplet energy: host materials for efficient blue phosphorescent OLEDs”, J. Mater. Chem. C, 2013, vol. 1, p. 463-469 (Year: 2013).*

* cited by examiner

[Figure 1]
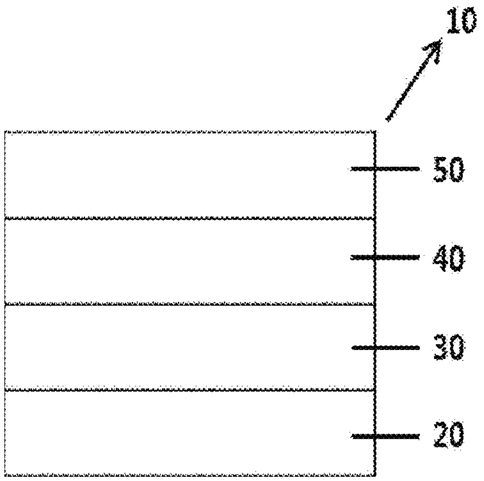
[Figure 2]
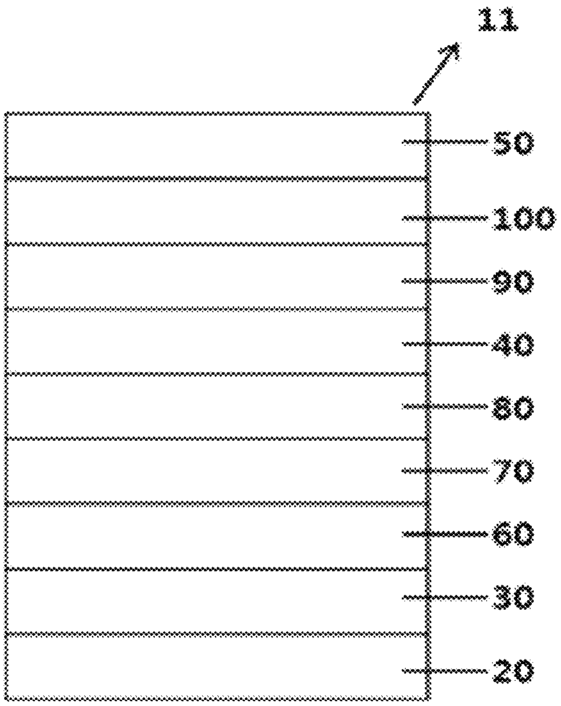

[Figure 3]
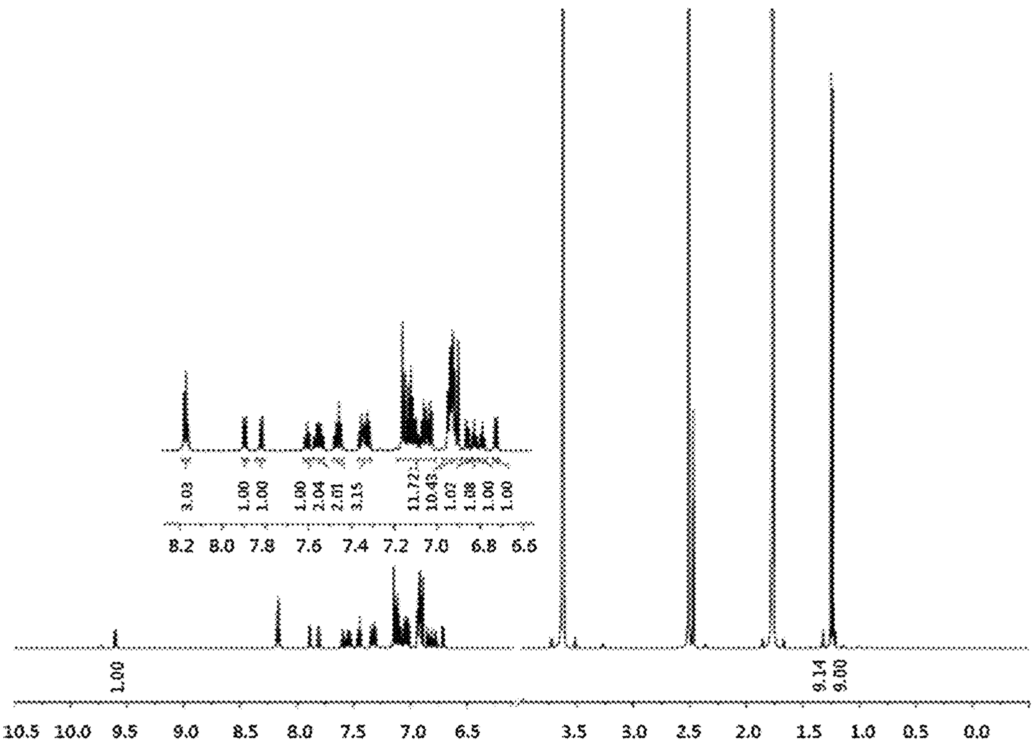

[Figure 4]
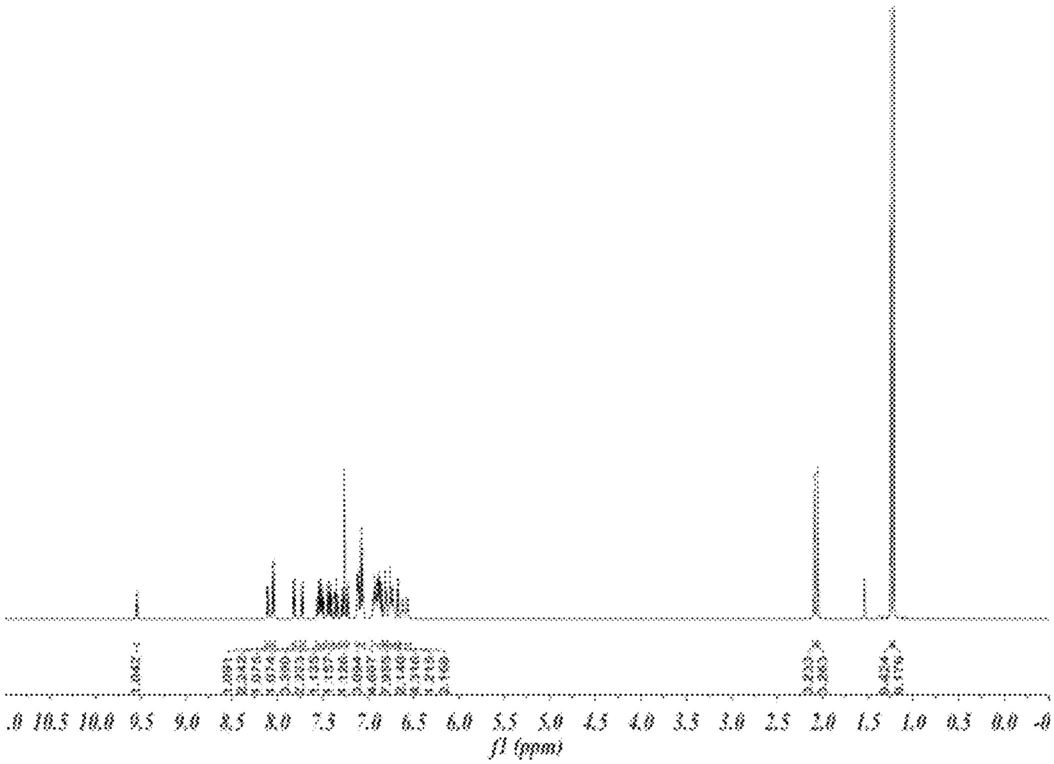
[Figure 5]
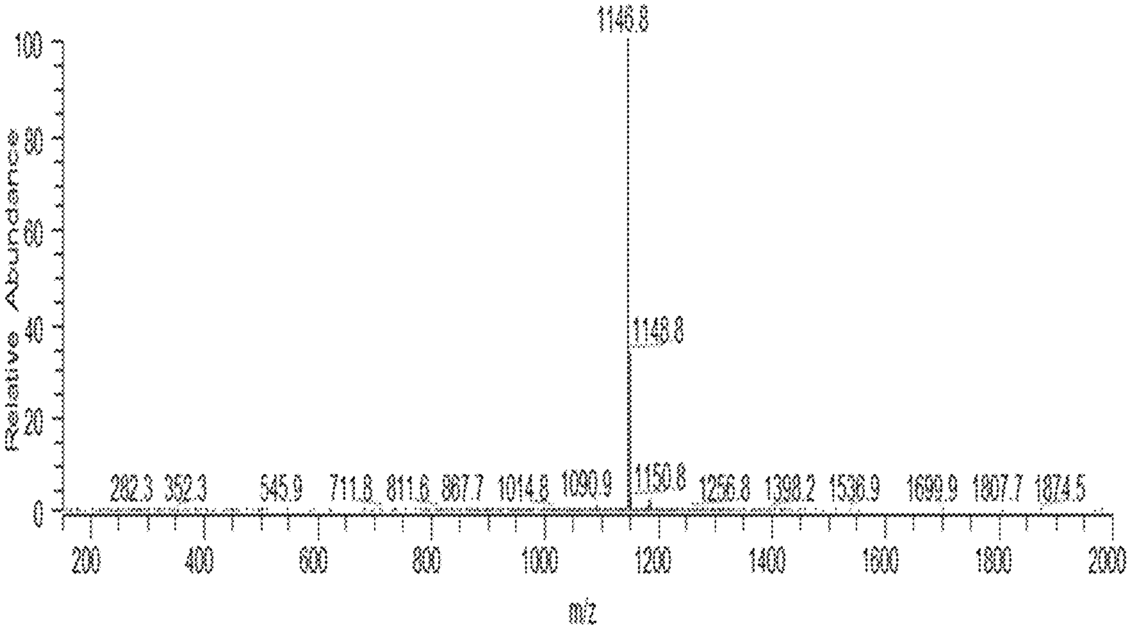

COMPOUND AND ORGANIC ELECTRONIC ELEMENT COMPRISING SAME

This application is a National Stage Application of International Application No. PCT/KR2017/007022 filed Jul. 3, 2017, and claims priority to and the benefit of Korean Patent Application No. 10-2016-0083592 filed in the Korean Intellectual Property Office on Jul. 1, 2016, the entire contents of which are incorporated herein by reference.

TECHNICAL FIELD

This application claims priority to and the benefit of Korean Patent Application No. 10-2016-0083592 filed in the Korean Intellectual Property Office on Jul. 1, 2016, the entire contents of which are incorporated herein by reference.

The present specification relates to a compound and an organic electronic device comprising the same.

BACKGROUND ART

Representative examples of an organic electronic device comprise an organic light emitting device. In general, an organic light emitting phenomenon refers to a phenomenon in which electric energy is converted into light energy by using an organic material. An organic light emitting device using the organic light emitting phenomenon usually has a structure comprising a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

REFERENCES OF THE RELATED ART

Patent Documents

International Publication No. 2003-012890

DISCLOSURE

Technical Problem

The present specification has been made in an effort to provide a compound and an organic electronic device comprising the same.

Technical Solution

The present specification provides a compound represented by the following Chemical Formula 1.

[Chemical Formula 1]

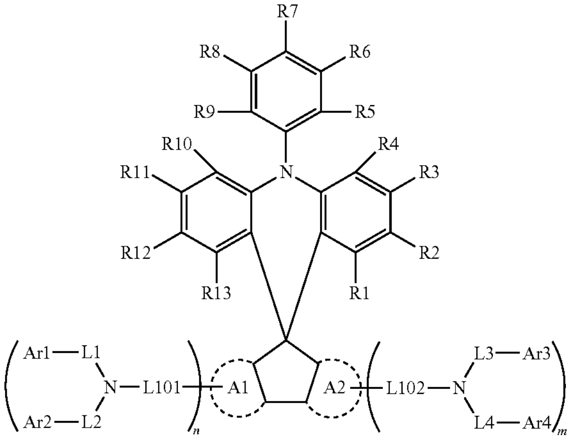

In Chemical Formula 1,

A1 and A2 are the same as or different from each other, and are each independently a substituted or unsubstituted aromatic hydrocarbon ring; or a substituted or unsubstituted hetero ring, L101, L102, and L1 to L4 are the same as or different from each other, and are each independently a direct bond; a substituted or unsubstituted arylene group; or a substituted or unsubstituted heteroarylene group, Ar1 to Ar4 are the same as or different from each other, and are each independently a substituted or unsubstituted alkyl group; a substituted or unsubstituted aryl group; or a substituted or unsubstituted heteroaryl group, or are optionally bonded to an adjacent group to form a ring, R1 to R13 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, R4 and R5 are optionally bonded to each other to form a pentagonal ring, m and n are an integer of 0 or 1, and at least one of m and n is an integer of 1.

Further, the present specification provides an organic electronic device comprising: a first electrode; a second electrode disposed to face the first electrode; and an organic material layer having one or more layers disposed between the first electrode and the second electrode, in which one or more layers of the organic material layer comprise the above-described compound.

Advantageous Effects

The compound according to an exemplary embodiment of the present specification is used for an organic electronic device comprising an organic light emitting device, and thus may lower the driving voltage of the organic electronic device and improve the light efficiency thereof, and enhance service life characteristics of the device due to thermal stability of the compound.

DESCRIPTION OF DRAWINGS

FIG. 1 illustrates an organic electronic device (10) according to an exemplary embodiment of the present specification.

FIG. 2 illustrates an organic electronic device (11) according to another exemplary embodiment of the present specification.

FIG. 3 is a view illustrating NMR data of Compound 5.

FIG. 4 is a view illustrating NMR data of Compound 47.

FIG. 5 is a view illustrating Mass data of Compound 60.

MODE FOR INVENTION

Hereinafter, the present specification will be described in more detail.

The present specification provides a compound represented by the following Chemical Formula 1.

[Chemical Formula 1]

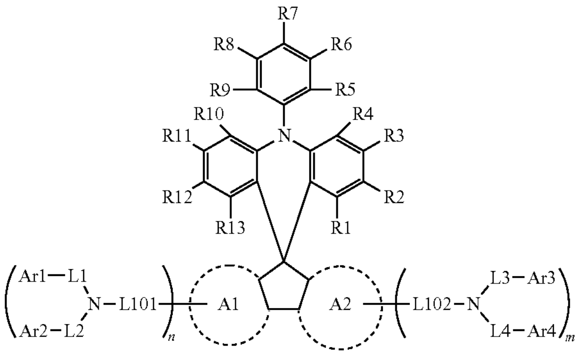

In Chemical Formula 1,

A1 and A2 are the same as or different from each other, and are each independently a substituted or unsubstituted aromatic hydrocarbon ring; or a substituted or unsubstituted hetero ring, L101, L102, and L1 to L4 are the same as or different from each other, and are each independently a direct bond; a substituted or unsubstituted arylene group; or a substituted or unsubstituted heteroarylene group, Ar1 to Ar4 are the same as or different from each other, and are each independently a substituted or unsubstituted alkyl group; a substituted or unsubstituted aryl group; or a substituted or unsubstituted heteroaryl group, or are optionally bonded to an adjacent group to form a ring, R1 to R13 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, R4 and R5 are optionally bonded to each other to form a pentagonal ring, m and n are an integer of 0 or 1, and at least one of m and n is an integer of 1.

Examples of the substituents in the present specification will be described below, but are not limited thereto.

In the present specification, “*”,

" 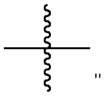 "

and “______” mean a moiety to be linked.

The term “substitution” means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term “substituted or unsubstituted” means being substituted with one or two or more substituents selected from the group consisting of deuterium; a halogen group; a nitrile group; a nitro group; an alkyl group; a cycloalkyl group; a silyl group; a phosphine oxide group; an aryl group; and a heteroaryl group including one or more of N, O, S, Se, and Si atoms, being substituted with a substituent to which two or more substituents among the substituents exemplified above are linked, or having no substituent.

In the present specification, examples of a halogen group comprise fluorine, chlorine, bromine or iodine.

In the present specification, an alkyl group may be straight or branched, and the number of carbon atoms thereof is not particularly limited, but is preferably 1 to 50. Specific examples thereof comprise methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, specific examples of a silyl group comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, when an aryl group is a monocyclic aryl group, the number of carbon atoms thereof is not particularly limited, but is preferably 6 to 60. Specific examples of the monocyclic aryl group comprise a phenyl group, a biphenyl group, a terphenyl group, a quarterphenyl group, and the like, but are not limited thereto.

When the aryl group is a polycyclic aryl group, the number of carbon atoms thereof is not particularly limited, but is preferably 10 to 60. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the group may be

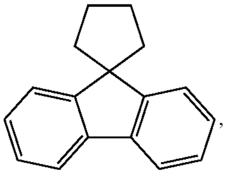
,
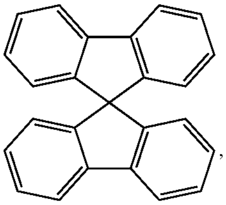
,
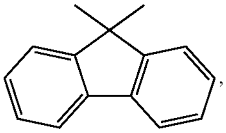
,
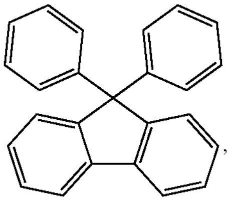
,
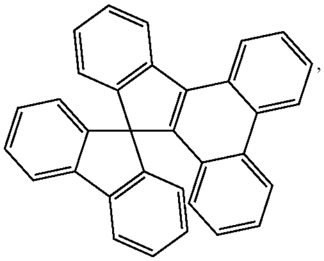
,
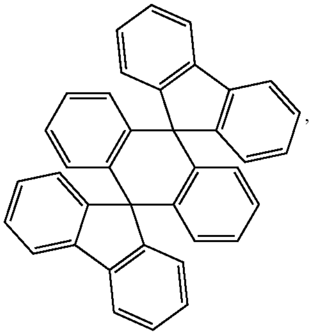
, and the like, but is not limited thereto.

In the present specification, a heteroaryl group is a heterocyclic group comprising one or more of N, O, S, Si, and Se as a heteroatom, and the number of carbon atoms thereof is not particularly limited, but is preferably 2 to 60. Examples of the heteroaryl group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a dibenzofuranyl group, and the like, but are not limited thereto.

In the present specification, a fused structure may be a structure in which an aromatic hydrocarbon ring is fused with the corresponding substituent.

Examples of a fused ring of benzimidazole comprise

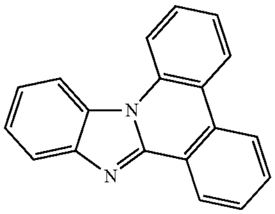
,
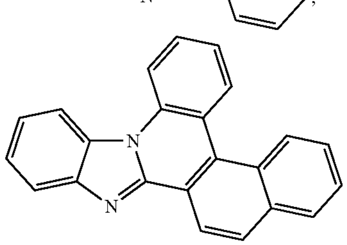
,
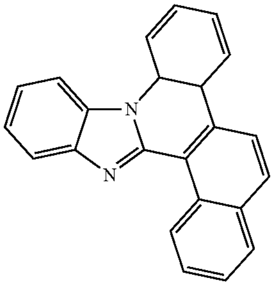
,
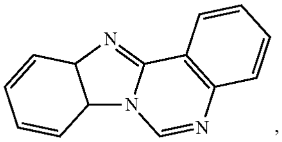
, and the like, but are not limited thereto.

Examples of a fused ring of acridine comprise

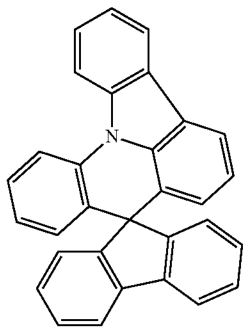 [SMILES: c1ccc2c(c1)-c1ccccc1C21c2ccccc2-n2c3ccccc3c3cccc1c32]

(spiro[fluorene-9,8'-indolo[3,2,1-de]acridine]), and the like, but are not limited thereto.

In the present specification, the "adjacent groups" may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as “adjacent groups” to each other.

In the present specification, the case where adjacent groups are bonded to each other to form a ring means that adjacent groups are bonded to each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

In the present specification, a hydrocarbon ring or a hetero ring may be selected among the above-described examples of the cycloalkyl group, the aryl group, or the heteroaryl group, except for being a monovalent group, and the hydrocarbon ring or the hetero ring may be monocyclic or polycyclic, an aliphatic ring or an aromatic ring or a fused form thereof, but is not limited thereto.

In the present specification, specific examples of a phosphine oxide group comprise a diphenylphosphine oxide group, dinaphthylphosphine oxide, and the like, but are not limited thereto.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

In an exemplary embodiment of the present specification, m and n are an integer of 0 or 1, and at least one of m and n is an integer of 1.

In another exemplary embodiment, m and n are 1.

In an exemplary embodiment of the present specification, A1 and A2 are the same as or different from each other, and are each independently a substituted or unsubstituted aromatic hydrocarbon ring; or a substituted or unsubstituted hetero ring.

According to another exemplary embodiment, A1 and A2 are the same as or different from each other, and are each independently a substituted or unsubstituted aromatic hydrocarbon ring having 6 to 60 carbon atoms; or a substituted or unsubstituted hetero ring having 2 to 60 carbon atoms.

According to still another exemplary embodiment, A1 and A2 are the same as or different from each other, and are each independently a substituted or unsubstituted aromatic hydrocarbon ring having 6 to 30 carbon atoms; or a substituted or unsubstituted hetero ring having 2 to 30 carbon atoms.

In an exemplary embodiment of the present specification, A1 and A2 are the same as or different from each other, and may be each independently any one selected from the following structural formulae, and the following structures may be additionally substituted.

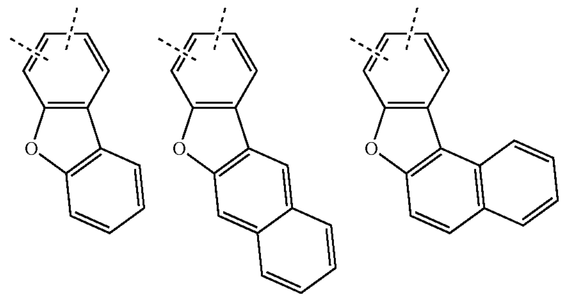

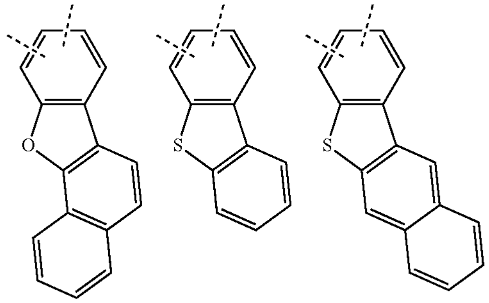

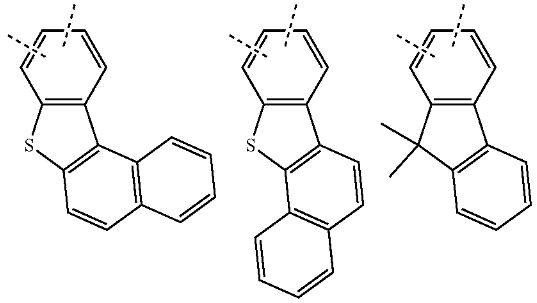

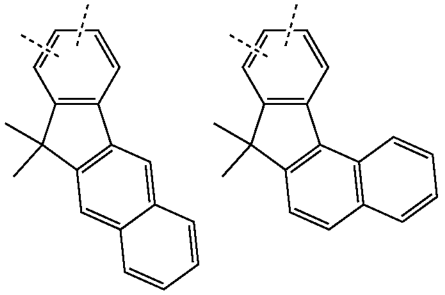

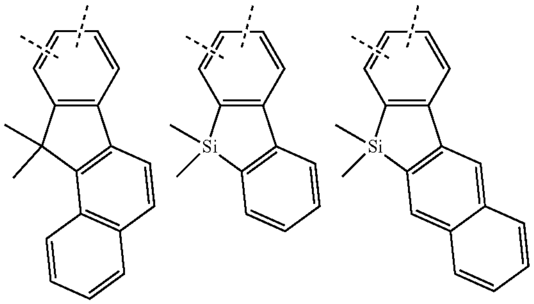

-continued
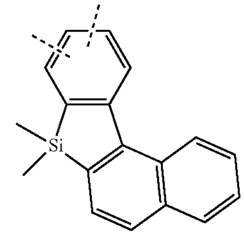
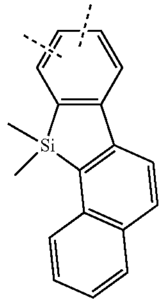
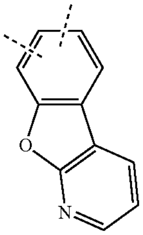
In an exemplary embodiment of the present specification, A1-L101-N(L1Ar1)(L2Ar2) and A2-L102-N(L3Ar3)(L4Ar4) are the same as or different from each other, and may be each independently any one selected from the following structural formulae.
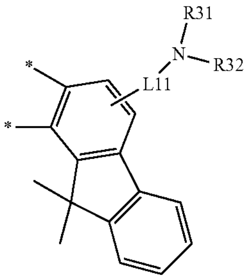
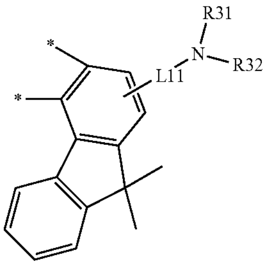
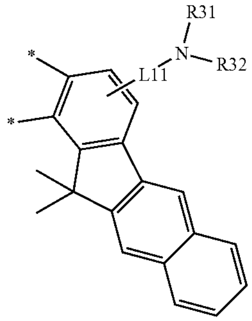
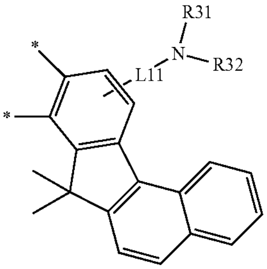
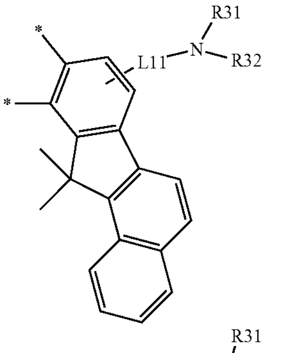
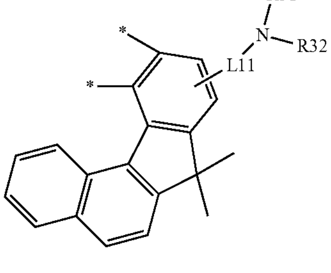
-continued
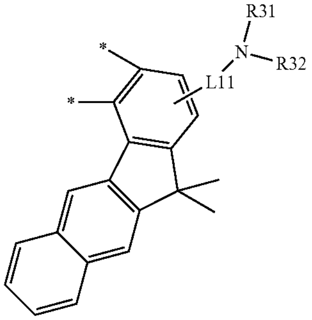
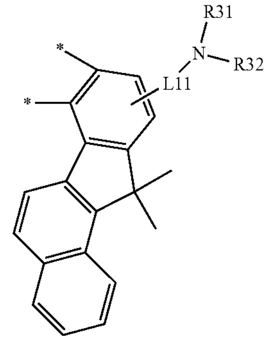
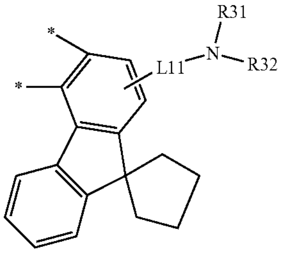
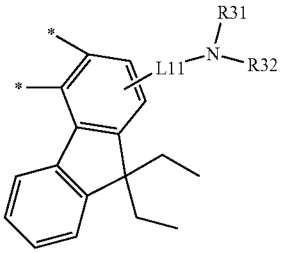
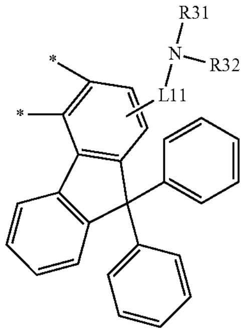
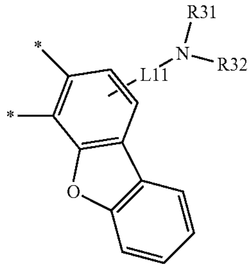
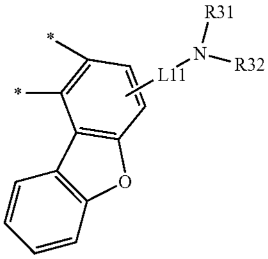
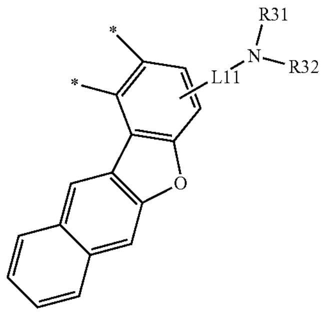

-continued
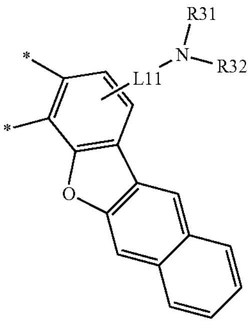
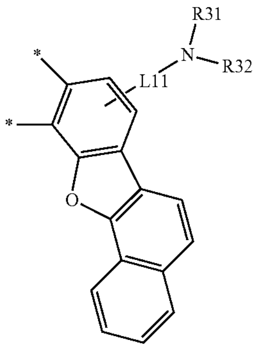
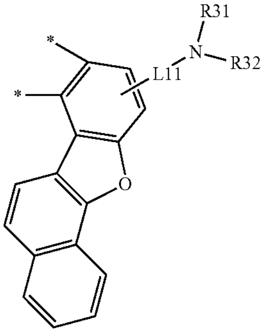
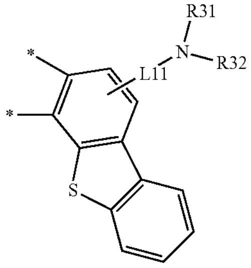
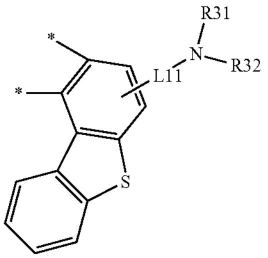
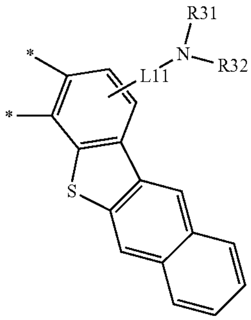
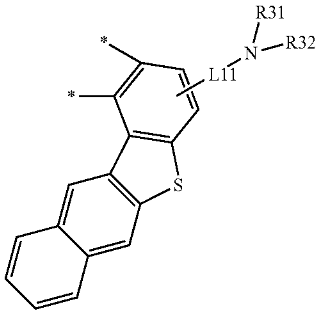
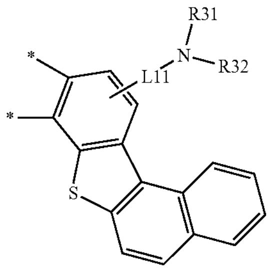
-continued
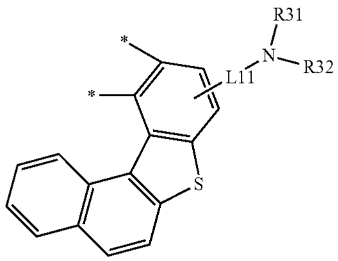
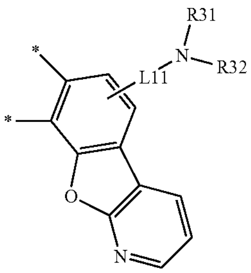
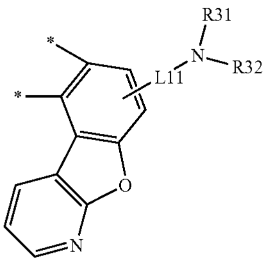
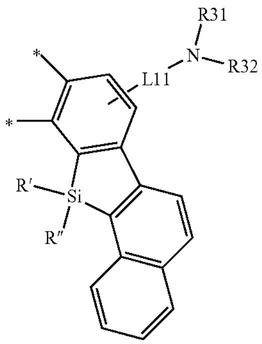
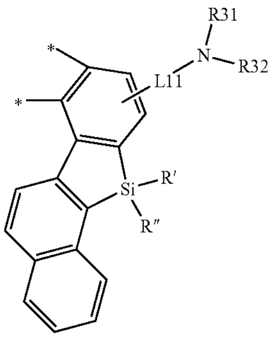
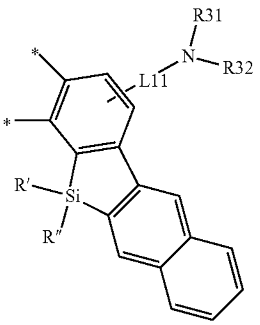
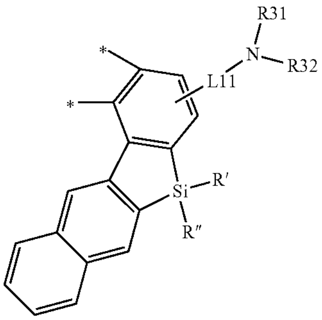

-continued

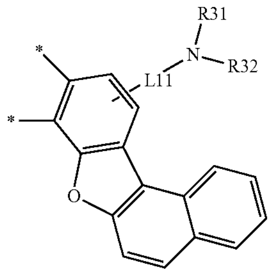

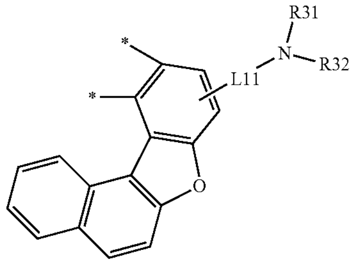

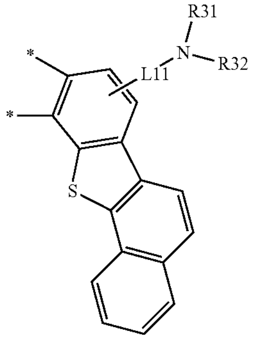

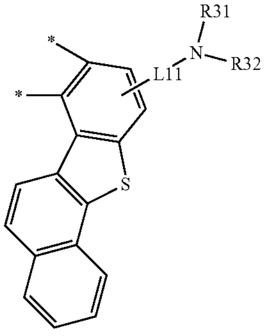

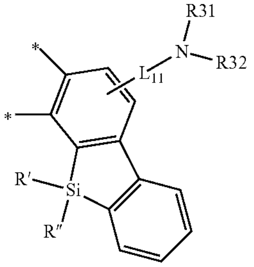

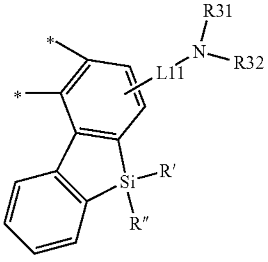

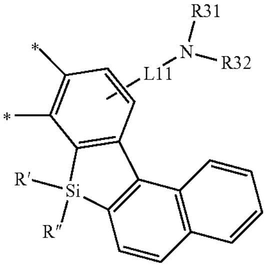

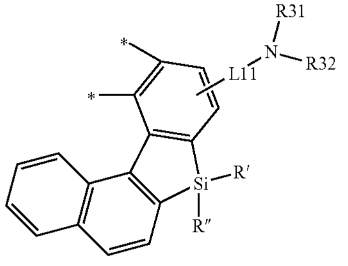

In the structures,

L11 is a direct bond; a substituted or unsubstituted arylene group; or a substituted or unsubstituted heteroarylene group, R' and R" are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, R31 and R32 are the same as or different from each other, and are each independently a substituted or unsubstituted alkyl group; a substituted or unsubstituted aryl group; or a substituted or unsubstituted heteroaryl group, or are optionally bonded to an adjacent group to form a ring, and the structures may be additionally substituted.

According to an exemplary embodiment of the present specification, R31 and R32 are the same as or different from each other, and are each independently the same as the definitions of the following Ar1 to Ar4.

According to an exemplary embodiment of the present specification, R' and R" are the same as or different from each other, and are each independently hydrogen; or a substituted or unsubstituted alkyl group.

According to another exemplary embodiment, R' and R" are the same as or different from each other, and are each independently hydrogen; or a substituted or unsubstituted alkyl group having 1 to 20 carbon atoms.

According to still another exemplary embodiment, R and R" are the same as or different from each other, and are each independently hydrogen; or a methyl group.

In an exemplary embodiment of the present specification, L11, L101, L102, and L1 to L4 are the same as or different from each other, and are each independently a direct bond; a substituted or unsubstituted arylene group; or a substituted or unsubstituted heteroarylene group.

In an exemplary embodiment of the present specification, L11, L101, L102, and L1 to L4 are the same as or different from each other, and are each independently a direct bond; or a substituted or unsubstituted arylene group having 6 to 50 carbon atoms.

In an exemplary embodiment of the present specification, L11, L101, L102, and L1 to L4 are the same as or different from each other, and are each independently a direct bond, a substituted or unsubstituted phenylene group, a substituted or unsubstituted biphenylylene group, a substituted or unsubstituted terphenylene group, a substituted or unsubstituted anthracene group, a substituted or unsubstituted phenanthrene group, a substituted or unsubstituted triphenylenyl group, a substituted or unsubstituted naphthylene group, or a substituted or unsubstituted fluorenylene group.

In an exemplary embodiment of the present specification, L11, L101, L102, and L1 to L4 are the same as or different from each other, and are each independently a direct bond, a phenylene group, a biphenylylene group, a terphenylene group, an anthracene group, a phenanthrene group, a triphenylenyl group, a naphthylene group, or a fluorenylene group substituted with a methyl group or a phenyl group.

In an exemplary embodiment of the present specification, L11, L101, L102, and L1 to L4 are the same as or different from each other, and are each independently a substituted or unsubstituted heteroarylene group having 3 to 50 carbon atoms.

In an exemplary embodiment of the present specification, L11, L101, L102, and L1 to L4 are the same as or different from each other, and are each independently a direct bond, a substituted or unsubstituted divalent pyrrole group, a substituted or unsubstituted divalent carbazole group, a substituted or unsubstituted divalent thiophene group, a substituted or unsubstituted divalent dibenzothiophene group, a substituted or unsubstituted divalent furan group, or a substituted or unsubstituted divalent dibenzofuran group.

In an exemplary embodiment of the present specification, L11, L101, L102, and L1 to L4 are the same as or different from each other, and are each independently a direct bond; a divalent pyrrole group unsubstituted or substituted with a methyl group or a phenyl group; a divalent carbazole group unsubstituted or substituted with an ethyl group or a phenyl group; a divalent thiophene group; a divalent dibenzofuran group; a divalent furan group; or a divalent dibenzofuran group.

In an exemplary embodiment of the present specification, L11, L101, L102, and L1 to L4 are the same as or different from each other, and may be each independently a direct bond; or any one selected from the substituents described below.

LA1

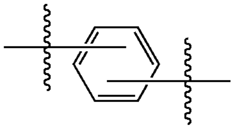

LA2

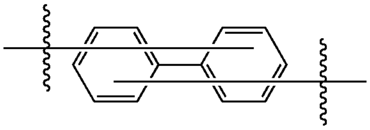

LA3

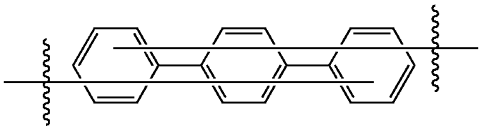

LA4

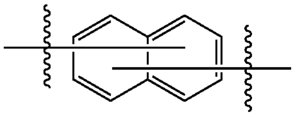

LA5

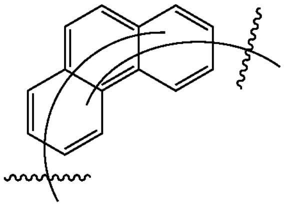

LA6

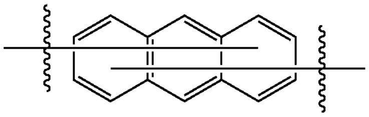

LA7

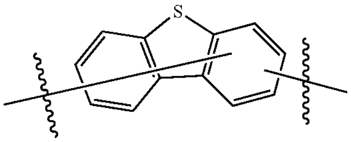

-continued

LA8

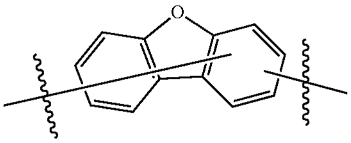

L9

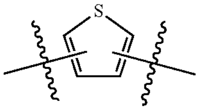

LA10

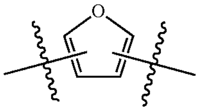

LA11

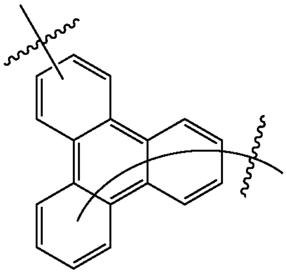

LA12

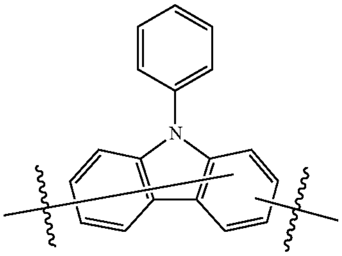

LA13

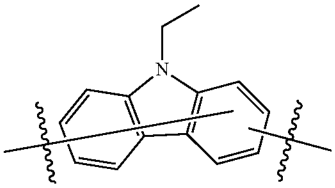

LA14

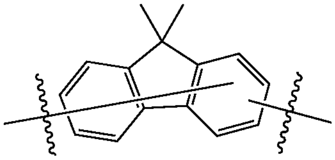

LA15

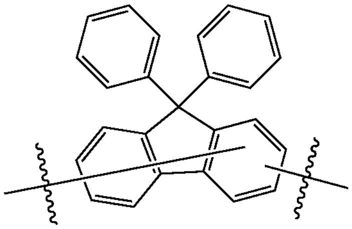

-continued

LA16

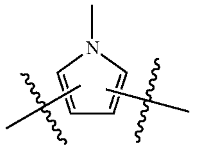

LA17

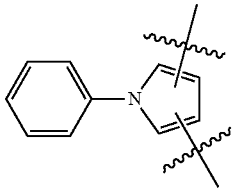

According to an exemplary embodiment of the present specification, L11, L101, L102, and L1 to L4 are a direct bond.

In an exemplary embodiment of the present specification, Ar1 to Ar4 are the same as or different from each other, and are each independently a substituted or unsubstituted alkyl group; a substituted or unsubstituted aryl group; or a substituted or unsubstituted heteroaryl group, or are optionally bonded to an adjacent group to form a ring.

According to an exemplary embodiment of the present specification, Ar1 to Ar4 are the same as or different from each other, and are each independently a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms, or are optionally bonded to an adjacent group to form a ring.

In another exemplary embodiment, Ar1 to Ar4 are the same as or different from each other, and are each independently a substituted or unsubstituted aryl group having 6 to 30 carbon atoms; or a substituted or unsubstituted heteroaryl group having 2 to 30 carbon atoms, or are optionally bonded to an adjacent group to form a ring.

According to another exemplary embodiment, Ar1 to Ar4 are the same as or different from each other, and are each independently a substituted or unsubstituted phenyl group; a substituted or unsubstituted naphthyl group; a substituted or unsubstituted biphenyl group; a substituted or unsubstituted terphenyl group; a substituted or unsubstituted anthracenyl group; a substituted or unsubstituted phenanthryl group; a substituted or unsubstituted triphenylenyl group; a substituted or unsubstituted fluoranthenyl group; a substituted or unsubstituted chrysenyl group; a substituted or unsubstituted pyrenyl group; a substituted or unsubstituted fluorenyl group; a substituted or unsubstituted indenofluorenyl group; a substituted or unsubstituted benzofluorenyl group; a substituted or unsubstituted pyridyl group; a substituted or unsubstituted pyrazinyl group; a substituted or unsubstituted pyridazinyl group; a substituted or unsubstituted pyrimidinyl group; a substituted or unsubstituted quinolinyl group; a substituted or unsubstituted quinoxalinyl group; a substituted or unsubstituted furan group; a substituted or unsubstituted thiophene group; a substituted or unsubstituted dibenzofuran group; a substituted or unsubstituted dibenzothiophene group; a substituted or unsubstituted naphthobenzofuran group; a substituted or unsubstituted naphthobenzothiophene group; a substituted or unsubstituted benzofuran group; a substituted or unsubstituted benzothiophene group; a substituted or unsubstituted benzoimidazole group; a substituted or unsubstituted benzoxazole group; a substituted or unsubstituted benzothiazole group; a substituted or unsubstituted fluorenobenzofuran group; or a substituted or unsubstituted benzofuranodibenzofuran group, or are optionally bonded to an adjacent group to form a ring.

According to another exemplary embodiment, Ar1 to Ar4 are bonded to an adjacent group to form an aromatic hetero ring.

According to still another exemplary embodiment, Ar1 to Ar4 are bonded to an adjacent group to form a substituted or unsubstituted carbazole.

According to yet another exemplary embodiment, Ar1 to Ar4 are bonded to an adjacent group to form a carbazole unsubstituted or substituted with a t-butyl group.

In an exemplary embodiment of the present specification, Ar1 to Ar4 may be any one selected from the structures described below.

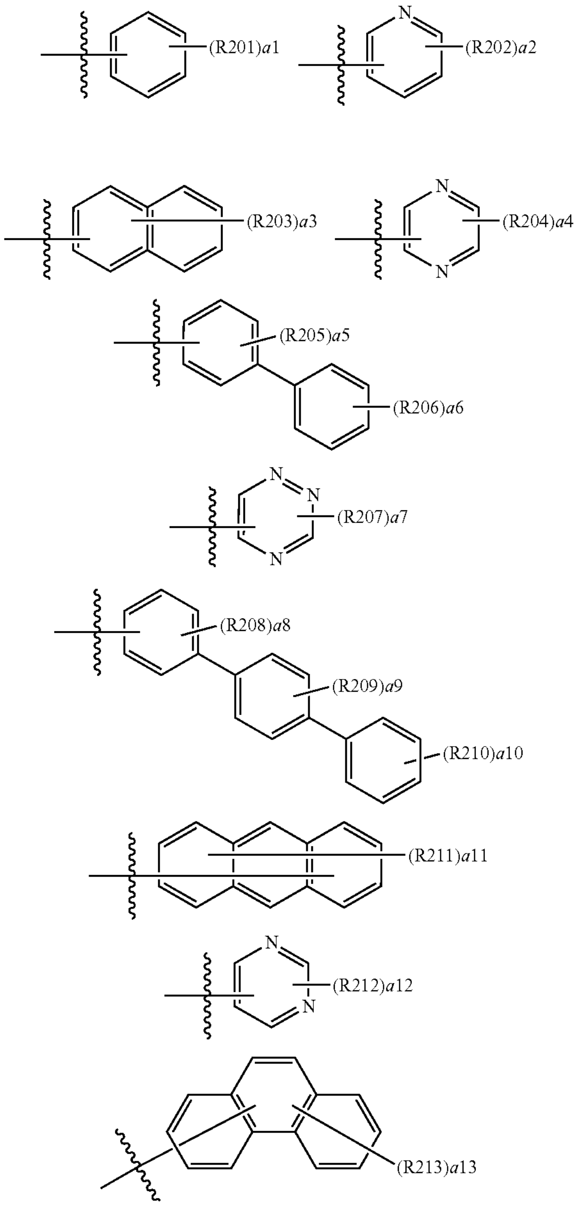

-continued
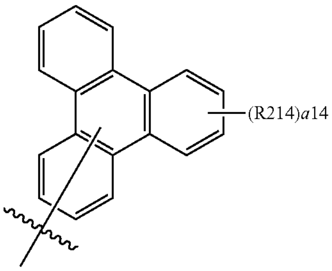
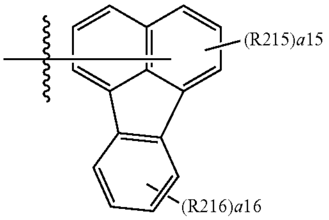
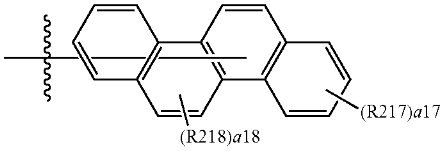
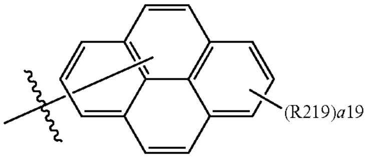
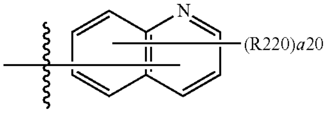
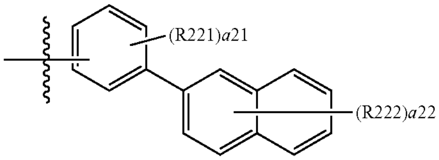
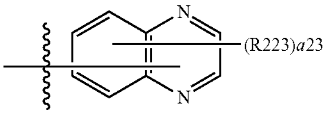
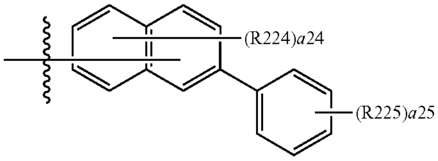
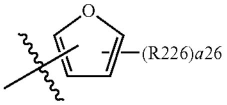
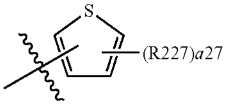
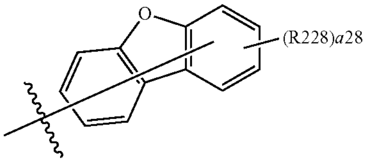
-continued
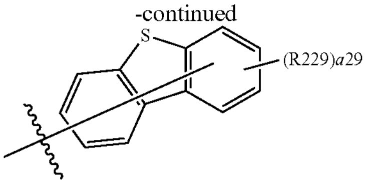
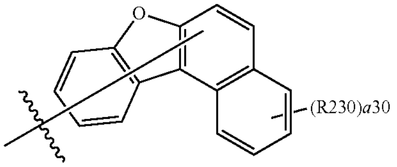
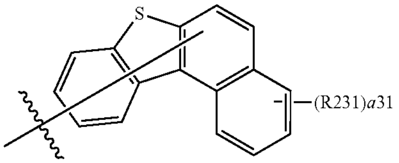
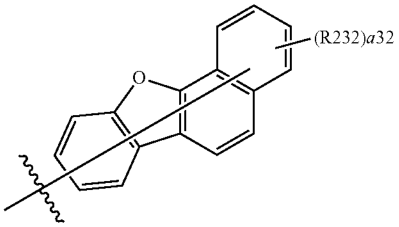
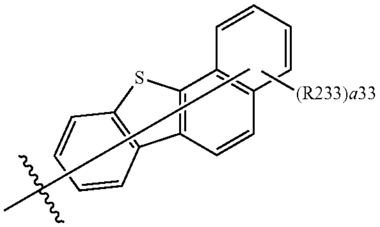
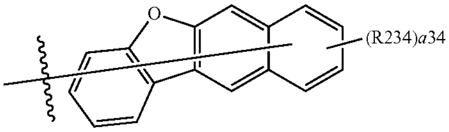
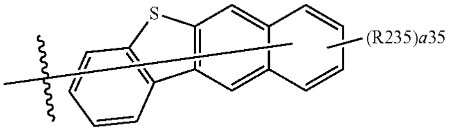
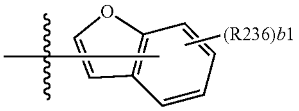
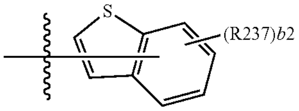
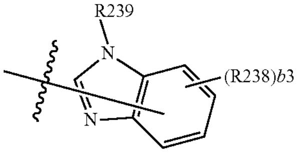
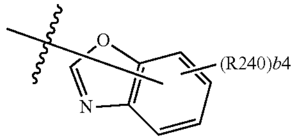

-continued
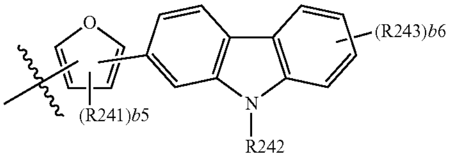
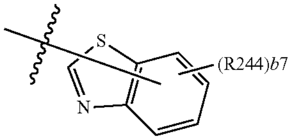
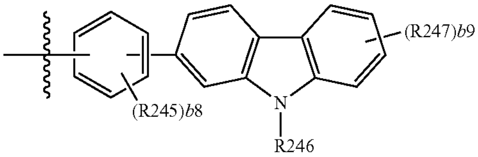
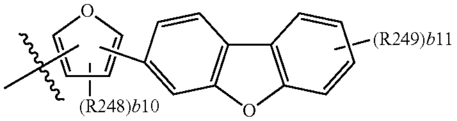
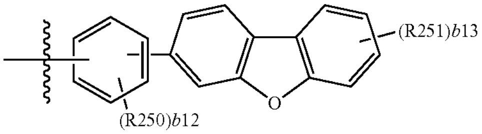
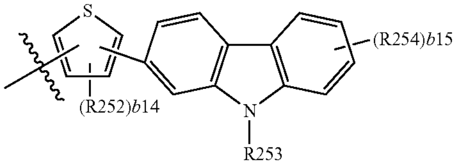
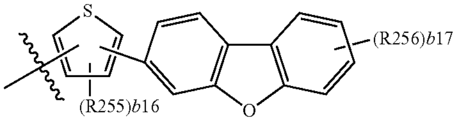
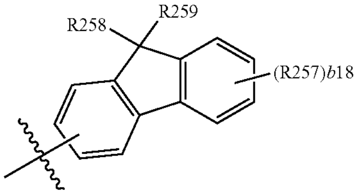
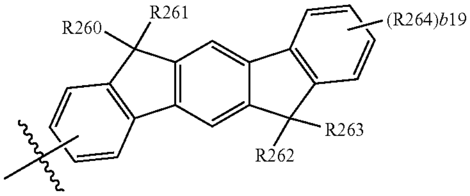
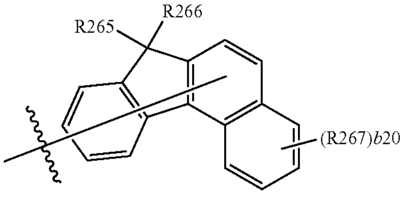
-continued
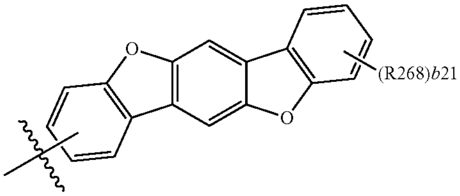
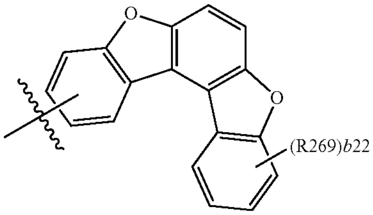
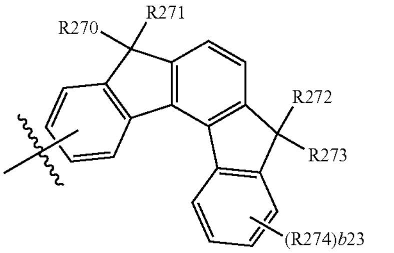
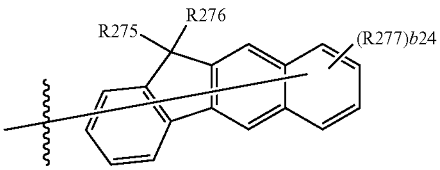
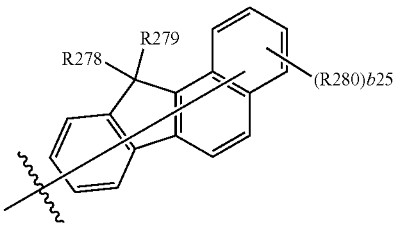
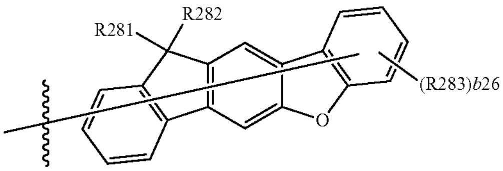
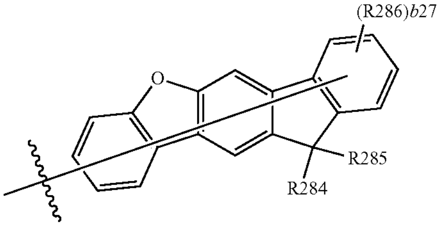
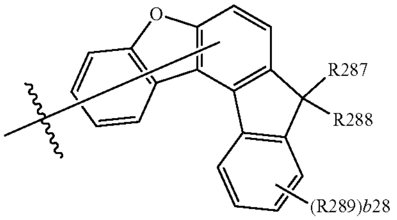

-continued

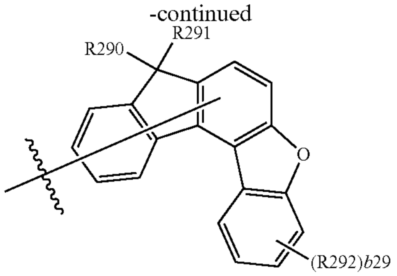

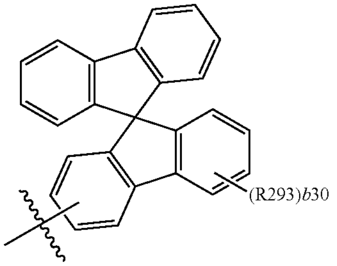

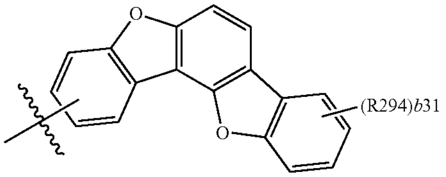

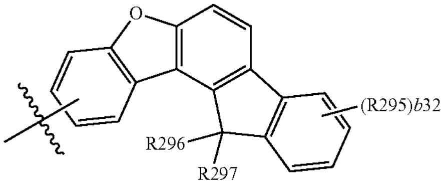

In the structures,

R201 to R297 are the same as or different from each other, and are each independently hydrogen; deuterium; a halogen group; a nitrile group; a nitro group; a silyl group; a boron group; a substituted or unsubstituted amine group; a substituted or unsubstituted alkyl group; a substituted or unsubstituted cycloalkyl group; a substituted or unsubstituted aryl group; or a substituted or unsubstituted heteroaryl group, or are optionally bonded to an adjacent group to form a ring, a1, a6, a10, a23, and a25 are each an integer from 0 to 5, a2, a5, a8, a9, a14, a16, a17, a21, a28 to a35, b1 to b4, b6 to b9, b11 to b13, b15, and b17 to b32 are each an integer from 0 to 4, a3 and a22 are each an integer from 0 to 7, a4, a7, a12, a15, a19, a26, and a27 are each an integer from 0 to 3, a11 is an integer from 0 to 9, a13, a20, and a24 are each an integer from 0 to 6, a18, b5, b10, b14, and b16 are each an integer from 0 to 2, when a18, b5, b10, b14, and b16 are 2, substituents in the parenthesis are different from each other, and when a1, a6, a10, a23, a25, a2, a5, a8, a9, a14, a16, a17, a21, a28 to a35, b1 to b4, b6 to b9, b11 to b13, b15, b17 to b32, a3, a22, a4, a7, a12, a15, a19, a26, a27, a11, a13, a20, and a24 are each 2 or more, substituents in the parenthesis are the same as or different from each other.

In an exemplary embodiment of the present specification, R201 to R297 are the same as or different from each other, and are each independently hydrogen; deuterium; a halogen group; a nitrile group; a silyl group; a substituted or unsubstituted alkyl group; a substituted or unsubstituted cycloalkyl group; or a substituted or unsubstituted aryl group, or are optionally bonded to an adjacent group to form a ring.

In another exemplary embodiment, R201 to R297 are the same as or different from each other, and are each independently hydrogen; deuterium; a halogen group; a nitrile group; a silyl group; a substituted or unsubstituted alkyl group having 1 to 30 carbon atoms; a substituted or unsubstituted cycloalkyl group having 3 to 30 carbon atoms; or a substituted or unsubstituted aryl group having 6 to 30 carbon atoms, or are optionally bonded to an adjacent group to form a ring.

In still another exemplary embodiment, R201 to R297 are the same as or different from each other, and are each independently hydrogen; deuterium; a halogen group; a nitrile group; a silyl group; a substituted or unsubstituted alkyl group having 1 to 20 carbon atoms; a substituted or unsubstituted cycloalkyl group having 3 to 20 carbon atoms; or a substituted or unsubstituted aryl group having 6 to 20 carbon atoms, or are optionally bonded to an adjacent group to form a ring.

In yet another exemplary embodiment, R201 to R297 are the same as or different from each other, and are each independently hydrogen; deuterium; a halogen group; a nitrile group; a silyl group unsubstituted or substituted with an alkyl group; a substituted or unsubstituted alkyl group having 1 to 20 carbon atoms; a substituted or unsubstituted cycloalkyl group having 3 to 20 carbon atoms; or a substituted or unsubstituted aryl group having 6 to 20 carbon atoms, or are optionally bonded to an adjacent group to form a ring.

According to still yet another exemplary embodiment, R201 to R297 are the same as or different from each other, and are each independently hydrogen; deuterium; a halogen group; a nitrile group; a silyl group substituted with a methyl group; a substituted or unsubstituted methyl group; a substituted or unsubstituted ethyl group; a substituted or unsubstituted isopropyl group; a substituted or unsubstituted t-butyl group; a substituted or unsubstituted phenyl group; a substituted or unsubstituted biphenyl group; a substituted or unsubstituted cyclopentyl group; or a substituted or unsubstituted cyclohexyl group, or are optionally bonded to an adjacent group to form a ring.

In a further exemplary embodiment, R201 to R297 are the same as or different from each other, and are each independently hydrogen; deuterium; fluorine (—F); a nitrile group; a trimethylsilyl group; a methyl group; an isopropyl group; a t-butyl group; a phenyl group; or a biphenyl group, or are optionally bonded to an adjacent group to form a ring.

In an exemplary embodiment of the present specification, a1 to a35 and b1 to b32 are each an integer from 0 to 2.

In an exemplary embodiment of the present specification, R1 to R13 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, or are optionally bonded to an adjacent group to form a ring.

According to an exemplary embodiment of the present specification, R1 to R13 are the same as or different from each other, and are each independently hydrogen; deuterium; or a substituted or unsubstituted alkyl group.

According to another exemplary embodiment, R1 to R13 are the same as or different from each other, and are each independently hydrogen; deuterium; or a substituted or unsubstituted alkyl group having 1 to 20 carbon atoms.

According to still another exemplary embodiment, R1 to R13 are the same as or different from each other, and are each independently hydrogen; deuterium; a substituted or unsubstituted methyl group; a substituted or unsubstituted ethyl group; or a substituted or unsubstituted t-butyl group.

In an exemplary embodiment of the present specification, R1 to R13 are the same as or different from each other, and are each independently hydrogen; deuterium; or a t-butyl group.

In an exemplary embodiment of the present specification, R4 and R5 may be bonded to each other to form a pentagonal ring.

In an exemplary embodiment of the present specification, Chemical Formula 1 may be represented by the following Chemical Formula 2 or 3.

[Chemical Formula 2]

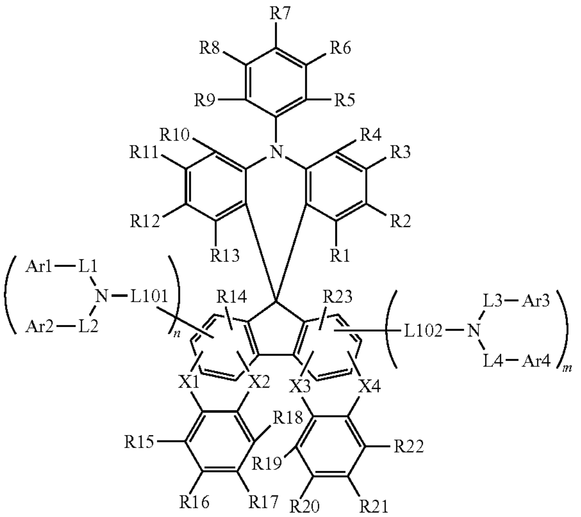

[Chemical Formula 3]

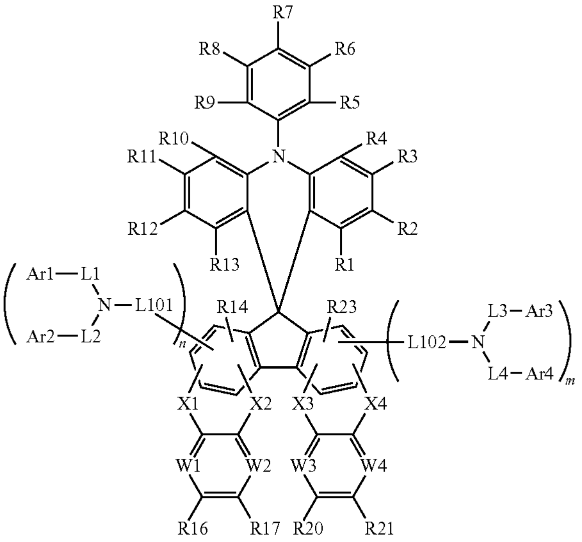

In Chemical Formulae 2 and 3, definitions of L101, L102, L1 to L4, Ar1 to Ar4, R1 to R13, m, and n are the same as those defined in Chemical Formula 1, any one of X1 and X2 is a direct bond, and the other is O, S, CY1Y2, or SiY5Y6, any one of X3 and X4 is a direct bond, and the other is O, S, CY3Y4, or SiY7Y8, W1 to W4 are the same as or different from each other, and are each independently N or CRa, and one or more of W1 to W4 are N, Y1 to Y8, Ra, and R14 to R23 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, or are optionally bonded to an adjacent group to form a ring.

In an exemplary embodiment of the present specification, any one of X1 and X2 is a direct bond, and the other is O, S, CY1Y2, or SiY5Y6.

In an exemplary embodiment of the present specification, X1 is O, and X2 is a direct bond.

In an exemplary embodiment of the present specification, X1 is S, and X2 is a direct bond.

In an exemplary embodiment of the present specification, X1 is CY1Y2, and X2 is a direct bond.

In an exemplary embodiment of the present specification, X1 is SiY5Y6, and X2 is a direct bond.

In an exemplary embodiment of the present specification, X1 is a direct bond, and X2 is O.

In an exemplary embodiment of the present specification, X1 is a direct bond, and X2 is S.

In an exemplary embodiment of the present specification, X1 is a direct bond, and X2 is CY1Y2.

In an exemplary embodiment of the present specification, X1 is a direct bond, and X2 is SiY5Y6.

In an exemplary embodiment of the present specification, any one of X3 and X4 is a direct bond, and the other is O, S, CY3Y4, or SiY7Y8.

In an exemplary embodiment of the present specification, X3 is O, and X4 is a direct bond.

In an exemplary embodiment of the present specification, X3 is S, and X4 is a direct bond.

In an exemplary embodiment of the present specification, X3 is CY3Y4, and X4 is a direct bond.

In an exemplary embodiment of the present specification, X3 is SiY7Y8, and X4 is a direct bond.

In an exemplary embodiment of the present specification, X3 is a direct bond, and X4 is O.

In an exemplary embodiment of the present specification, X3 is a direct bond, and X4 is S.

In an exemplary embodiment of the present specification, X3 is a direct bond, and X4 is CY3Y4.

In an exemplary embodiment of the present specification, X3 is a direct bond, and X4 is SiY7Y8.

In an exemplary embodiment of the present specification, Y1 to Y8, Ra, and R14 to R23 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, or are optionally bonded to an adjacent group to form a ring.

In an exemplary embodiment of the present specification, Ra is hydrogen.

In an exemplary embodiment of the present specification, Y1 and Y2 are the same as or different from each other, and are each independently a substituted or unsubstituted alkyl group.

In an exemplary embodiment of the present specification, Y1 and Y2 are the same as or different from each other, and are each independently a methyl group.

In an exemplary embodiment of the present specification, Y3 and Y4 are the same as or different from each other, and are each independently a substituted or unsubstituted alkyl group.

In an exemplary embodiment of the present specification, Y3 and Y4 are the same as or different from each other, and are each independently a methyl group.

In an exemplary embodiment of the present specification, Y5 and Y6 are the same as or different from each other, and are each independently a substituted or unsubstituted alkyl group.

In an exemplary embodiment of the present specification, Y5 and Y6 are the same as or different from each other, and are each independently a methyl group.

In an exemplary embodiment of the present specification, Y7 and Y8 are the same as or different from each other, and are each independently a substituted or unsubstituted alkyl group.

In an exemplary embodiment of the present specification, Y7 and Y8 are the same as or different from each other, and are each independently a methyl group.

In an exemplary embodiment of the present specification, R14 to R23 are the same as or different from each other, and are each independently hydrogen; a substituted or unsubstituted alkyl group; or a substituted or unsubstituted aryl group.

In another exemplary embodiment, R14 to R23 are the same as or different from each other, and are each independently hydrogen; a substituted or unsubstituted alkyl group having 1 to 40 carbon atoms; or a substituted or unsubstituted aryl group having 6 to 40 carbon atoms.

In an exemplary embodiment of the present specification, R14 to R23 are hydrogen.

In an exemplary embodiment of the present specification, Chemical Formula 1 may be represented by the following Chemical Formula 4 or 5.

[Chemical Formula 4]

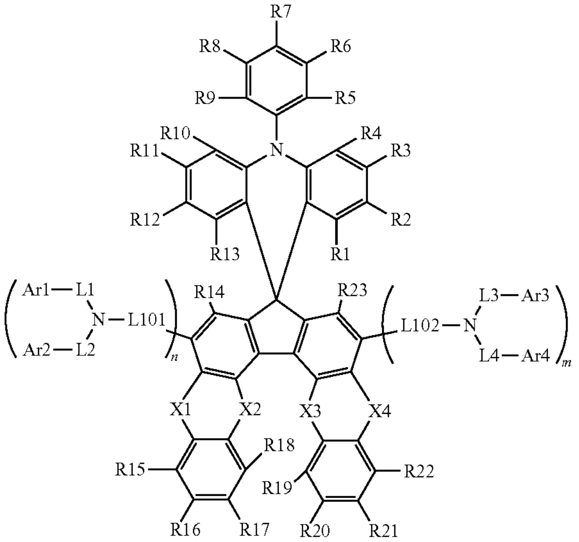

-continued

[Chemical Formula 5]

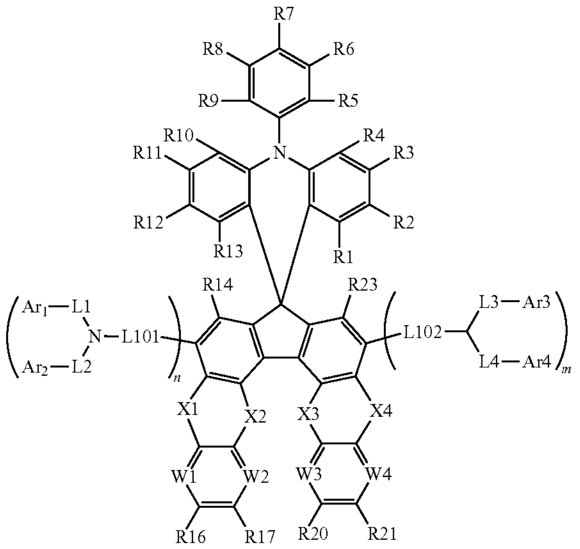

In Chemical Formulae 4 and 5, definitions of L101, L102, L1 to L4, Ar1 to Ar4, R1 to R13, m, and n are the same as those defined in Chemical Formula 1, any one of X1 and X2 is a direct bond, and the other is O, S, CY1Y2, or SiY5Y6, any one of X3 and X4 is a direct bond, and the other is O, S, CY3Y4, or SiY7Y8, W1 to W4 are the same as or different from each other, and are each independently N or CRa, and one or more of W1 to W4 are N, and Y1 to Y8, Ra, and R14 to R23 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, or are optionally bonded to an adjacent group to form a ring.

In an exemplary embodiment of the present specification, Chemical Formula 1 may be represented by the following Chemical Formula 6 to 21.

-continued
[Chemical Formula 6]
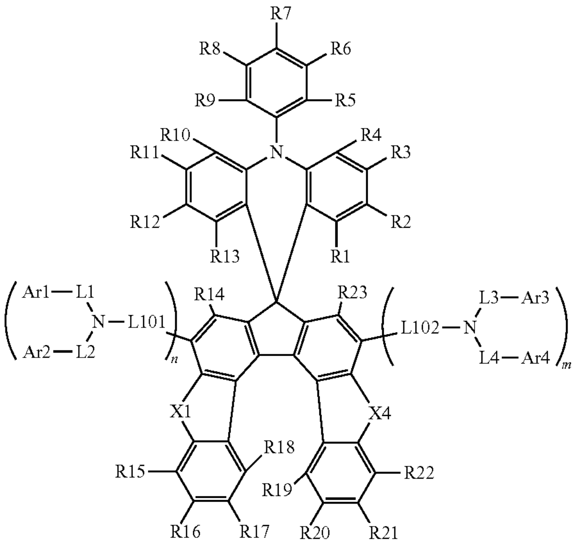
[Chemical Formula 7]
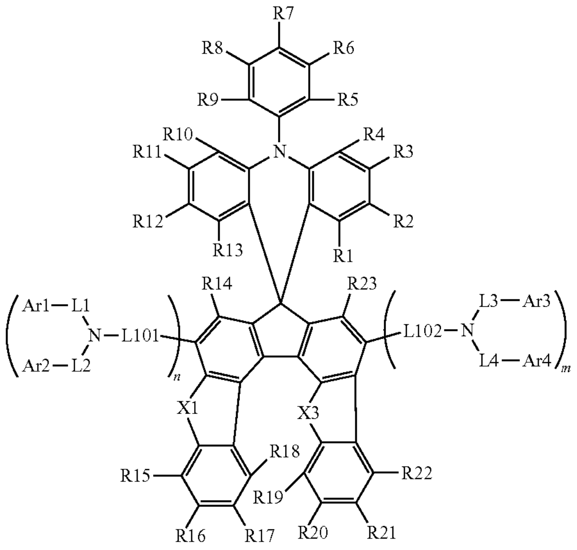
[Chemical Formula 8]
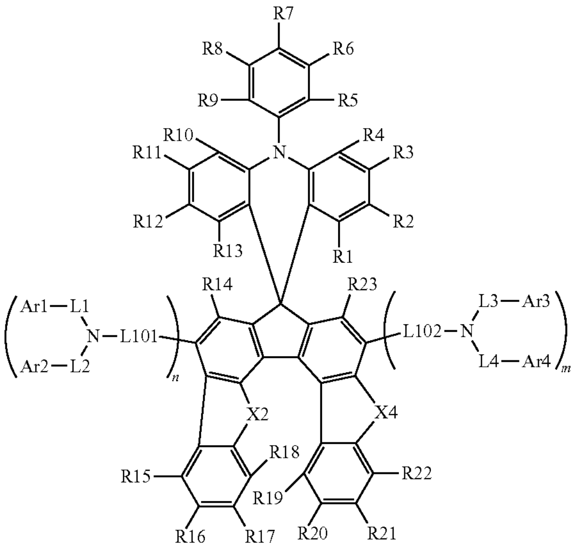
[Chemical Formula 9]
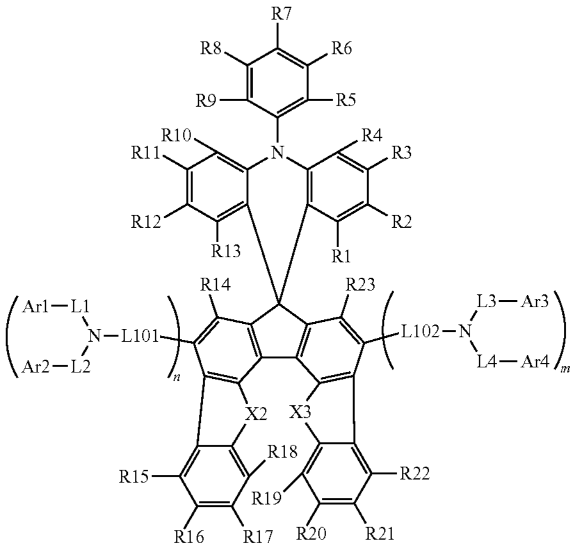

-continued
[Chemical Formula 10]
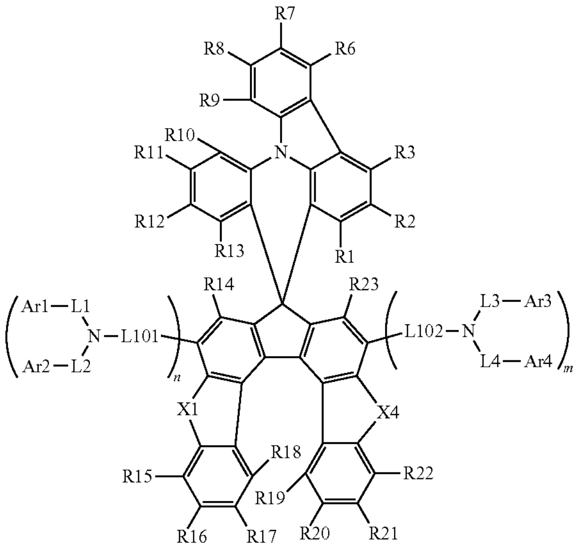
[Chemical Formula 11]
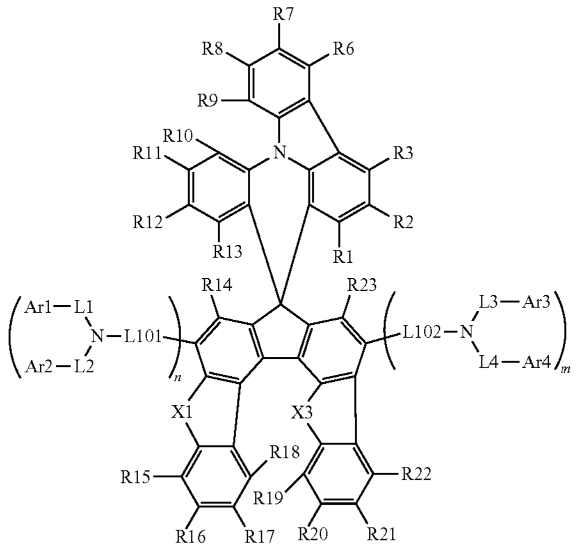
-continued
[Chemical Formula 12]
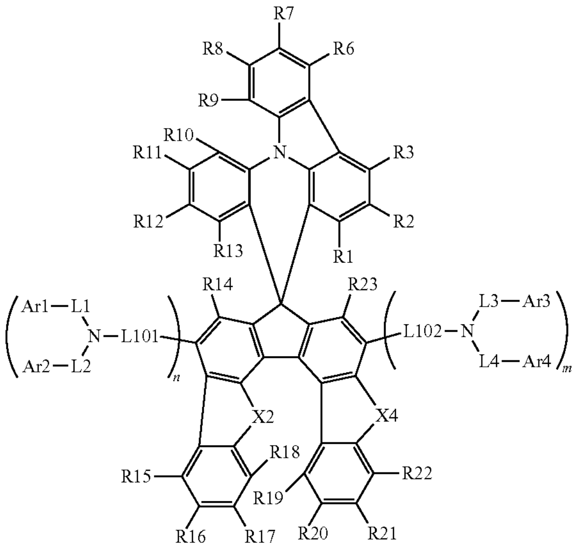
[Chemical Formula 13]
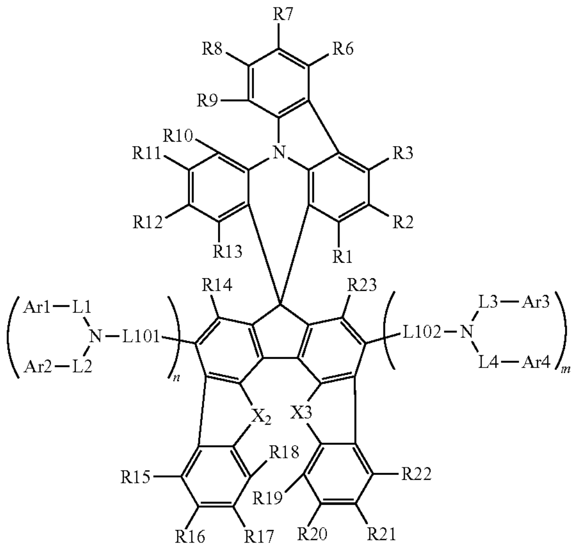

-continued
[Chemical Formula 14]
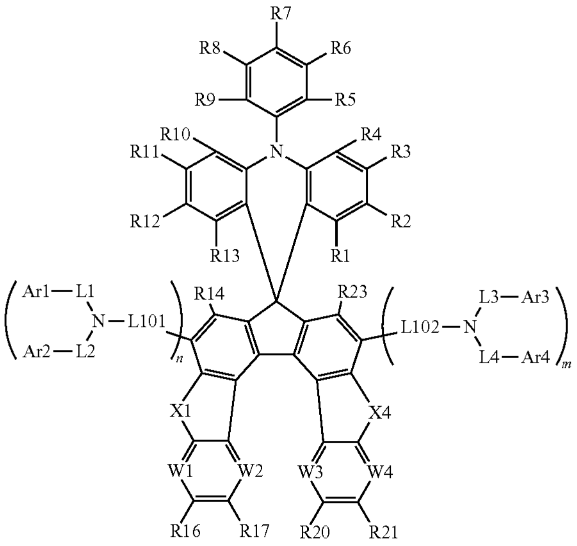
[Chemical Formula 15]
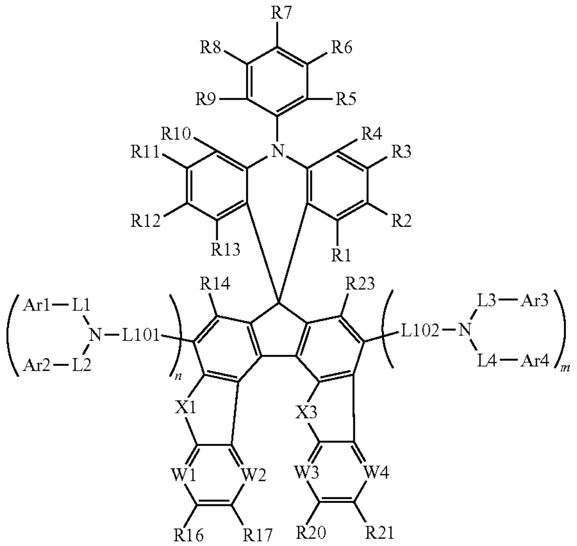
-continued
[Chemical Formula 16]
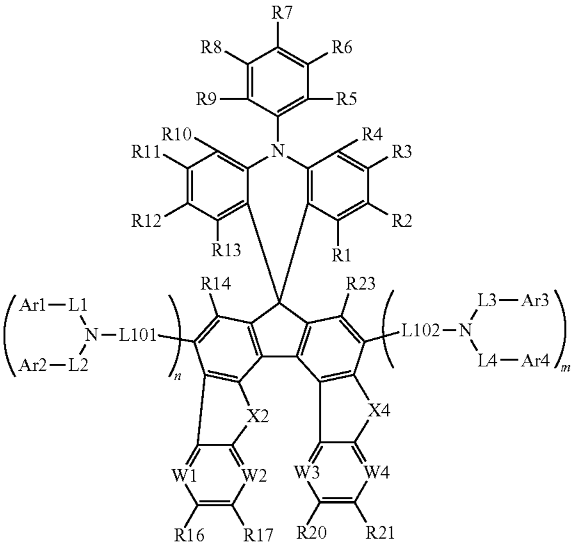
[Chemical Formula 17]
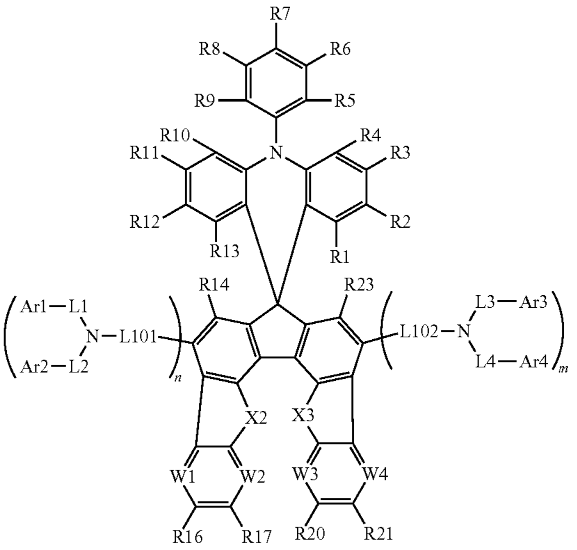

-continued

[Chemical Formula 18]

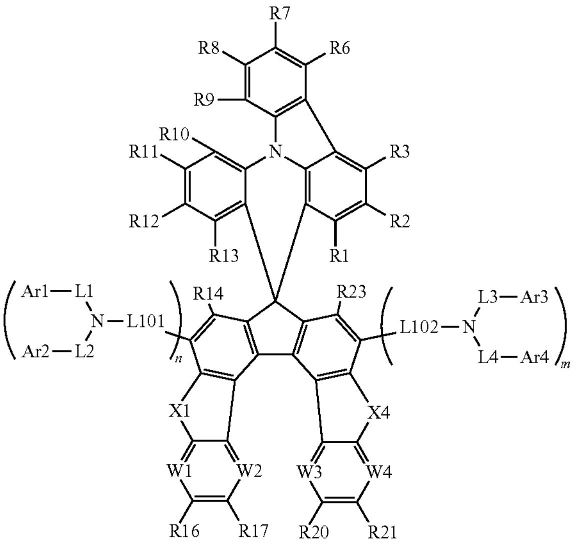

[Chemical Formula 19]

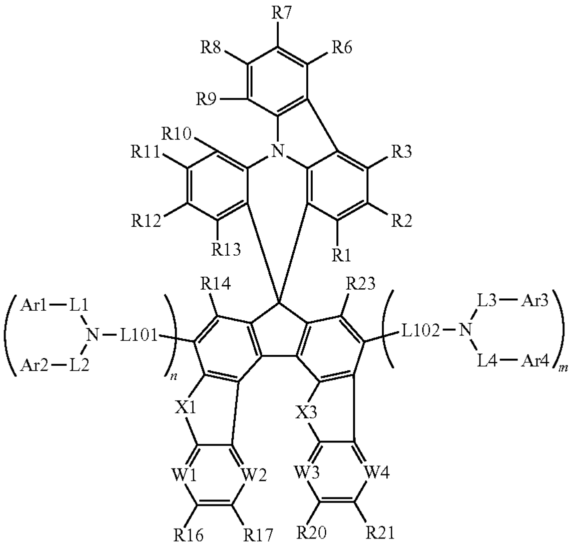

-continued

[Chemical Formula 20]

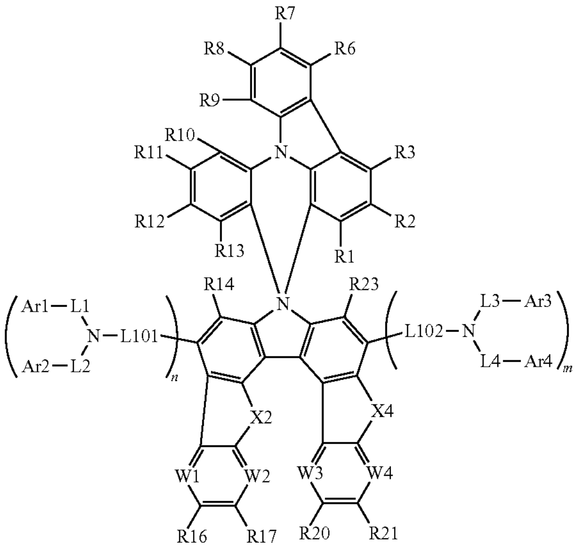

[Chemical Formula 21]

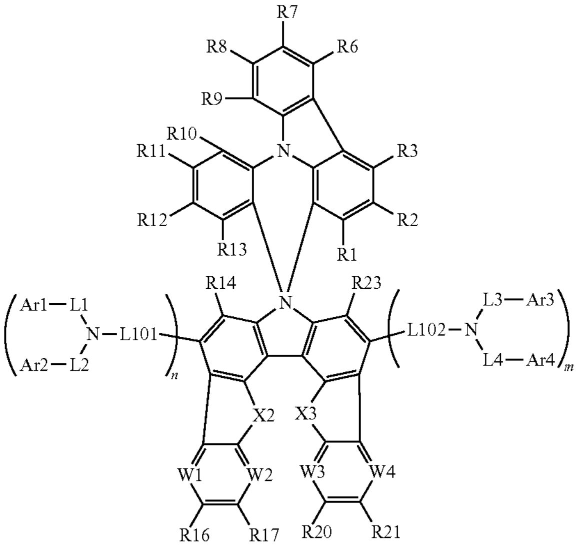

In Chemical Formulae 6 to 21, definitions of L101, L102, L1 to L4, A1 to Ar4, R1 to R13, m, and n are the same as those defined in Chemical Formula 1, any one of X1 and X2 is a direct bond, and the other is O, S, CY1Y2, or SiY5Y6, any one of X3 and X4 is a direct bond, and the other is O, S, CY3Y4, or SiY7Y8, W1 to W4 are the same as or different from each other, and are each independently N or CRa, and one or more of W1 to W4 are N, and Y1 to Y8, Ra, and R14 to R23 are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, or are optionally bonded to an adjacent group to form a ring.

In an exemplary embodiment of the present specification, Chemical Formula 1 may be any one selected from the following compounds.
Compound 1
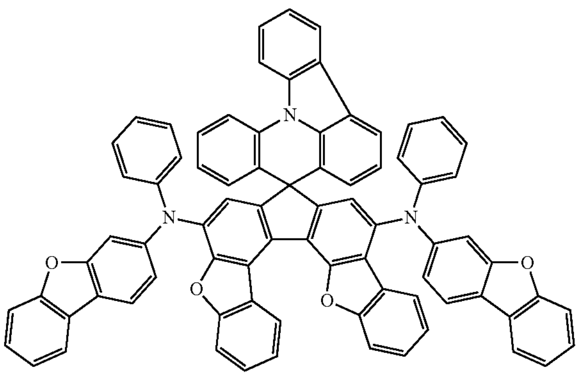
Compound 2
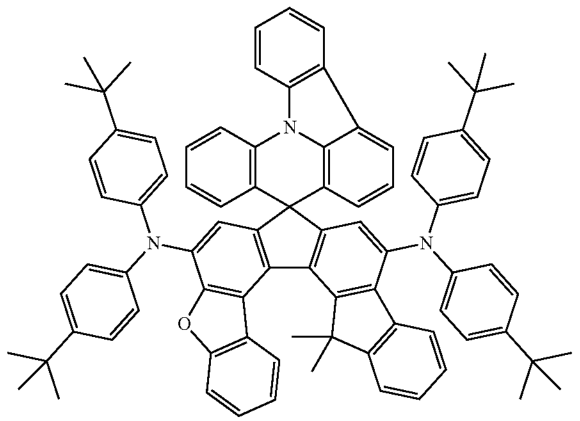
Compound 3
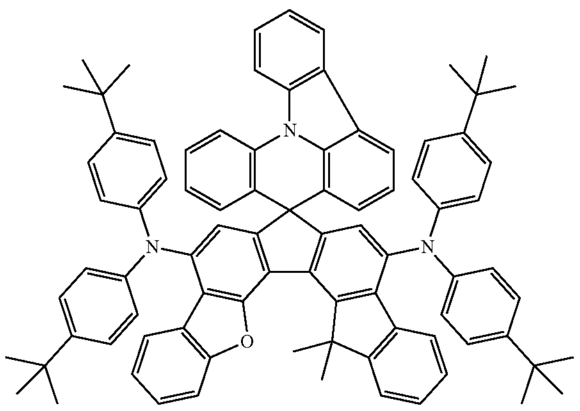
-continued
Compound 4
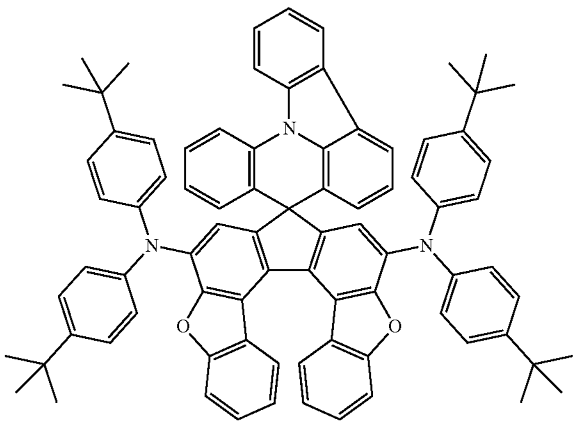
Compound 5
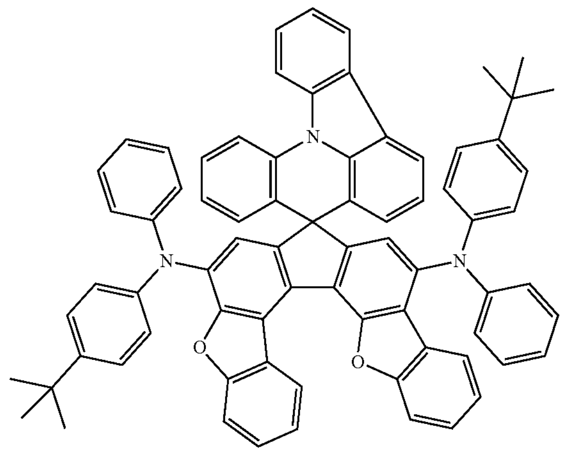
Compound 6
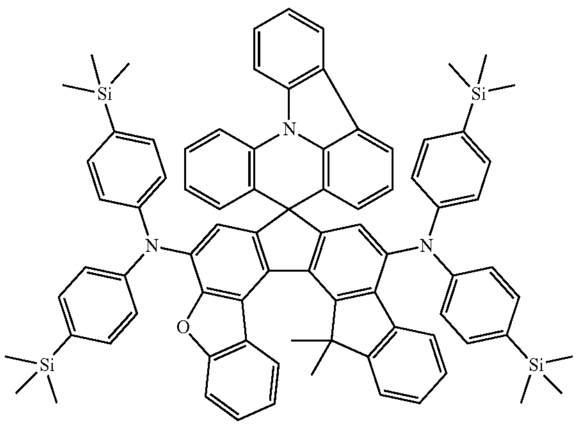

-continued
Compound 7
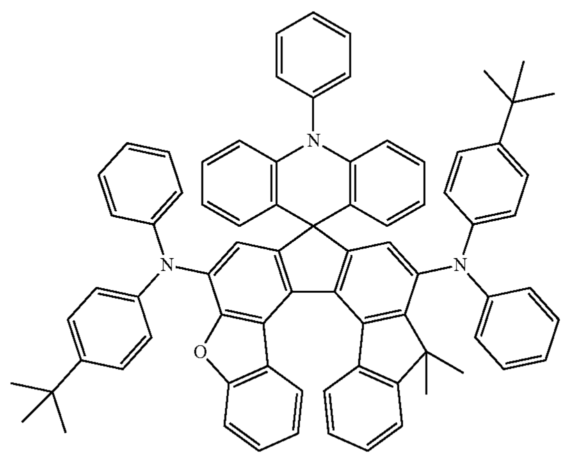
Compound 8
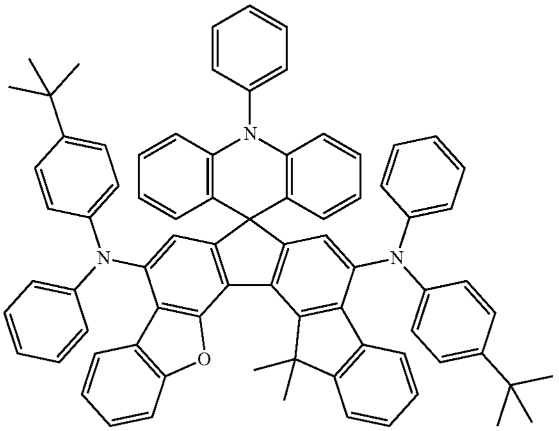
Compound 9
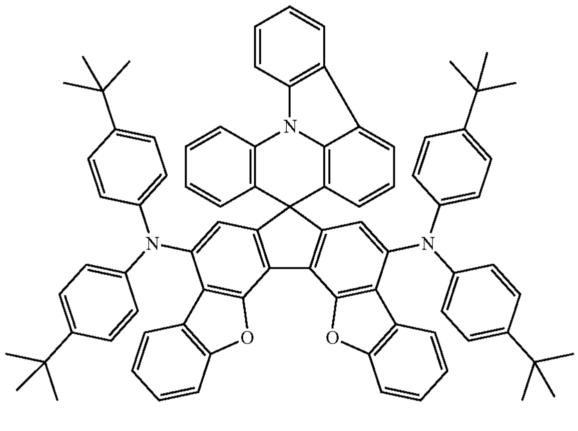
-continued
Compound 10
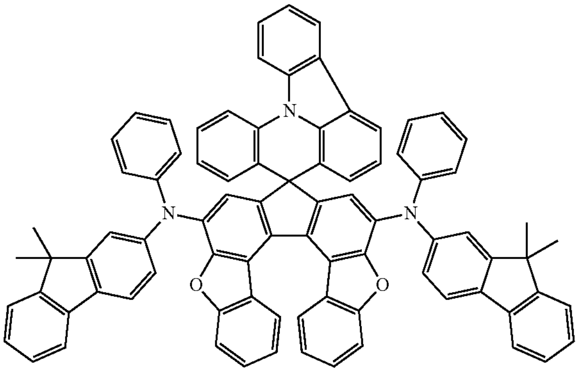
Compound 11
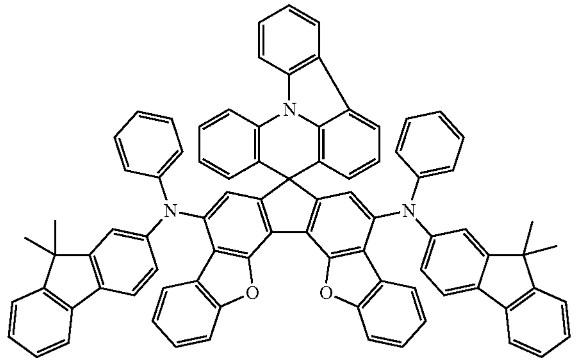
Compound 12
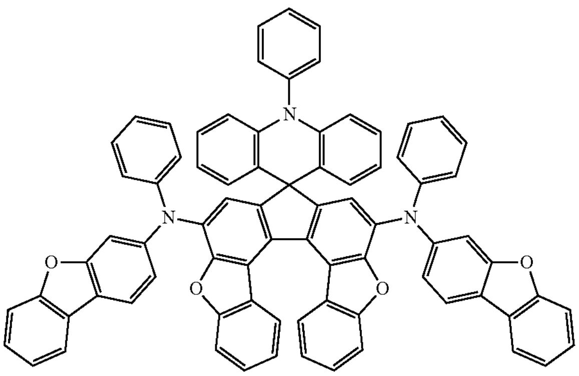
Compound 13
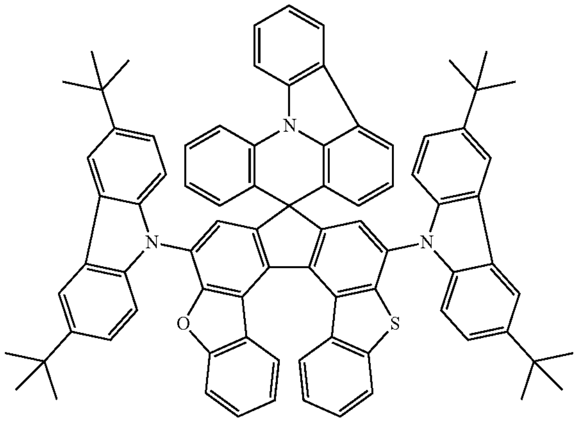

-continued
Compound 14
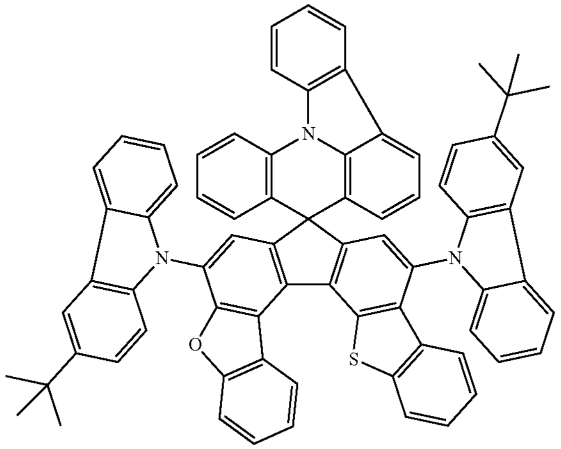
Compound 15
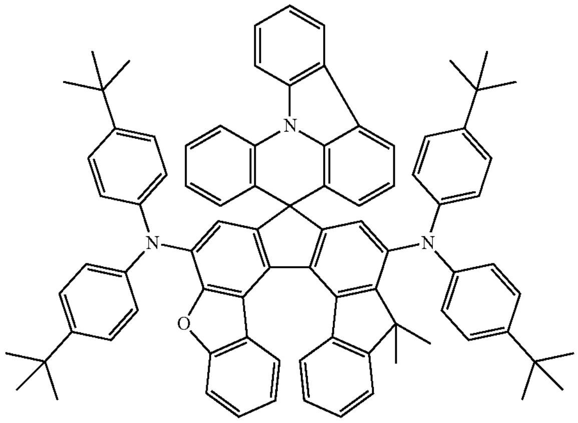
Compound 16
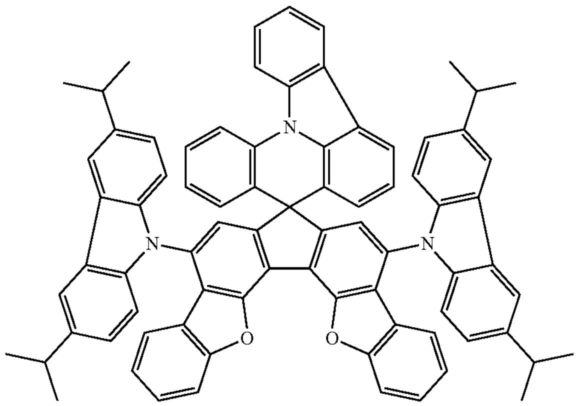
-continued
Compouns 17
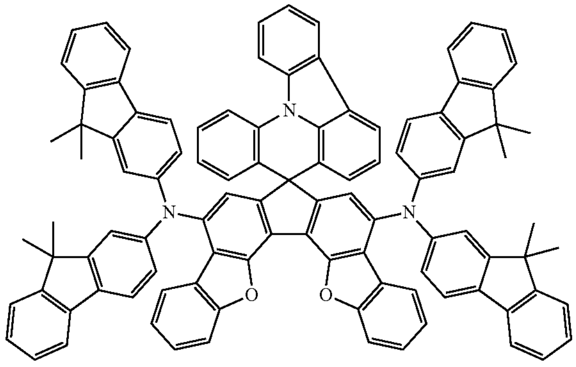
Compound 18
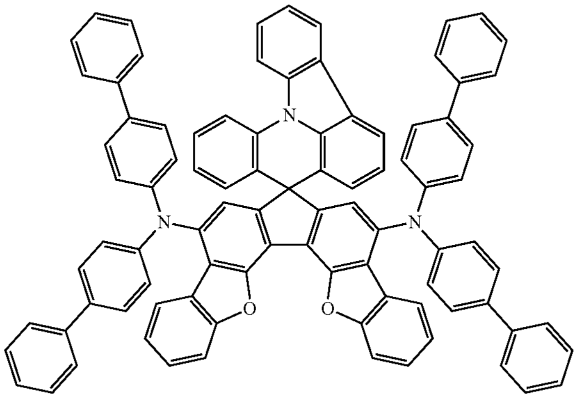
Compound 19
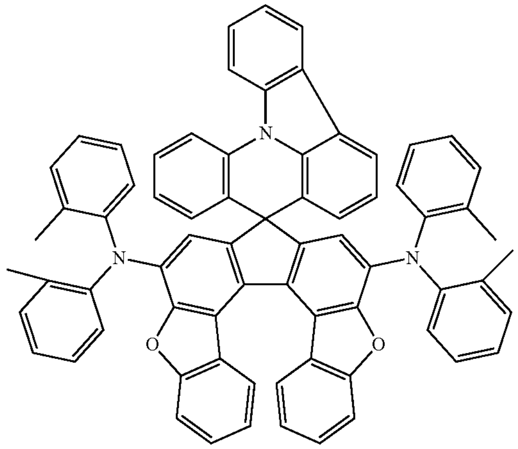

-continued
Compound 20
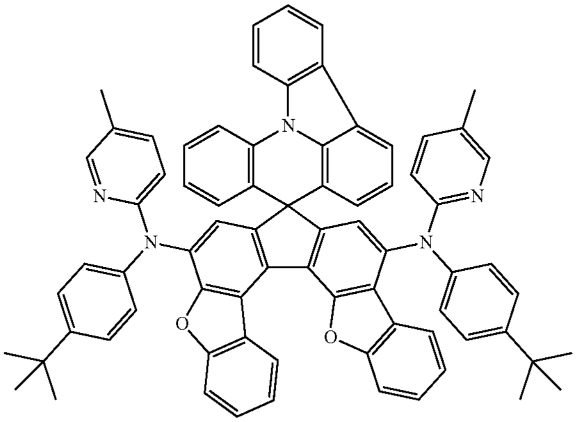
Compound 21
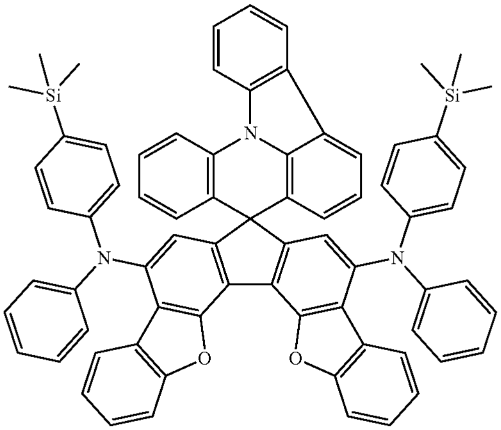
Compound 22
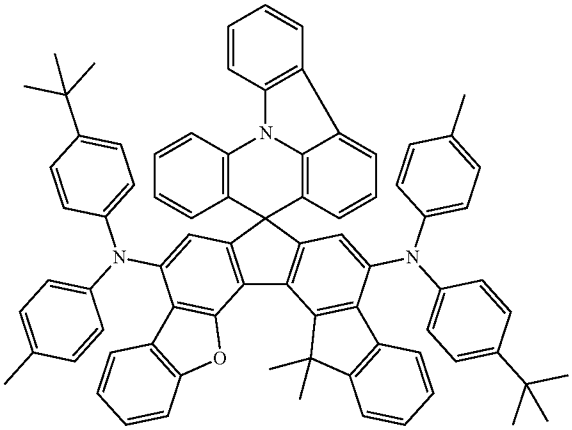
-continued
Compound 23
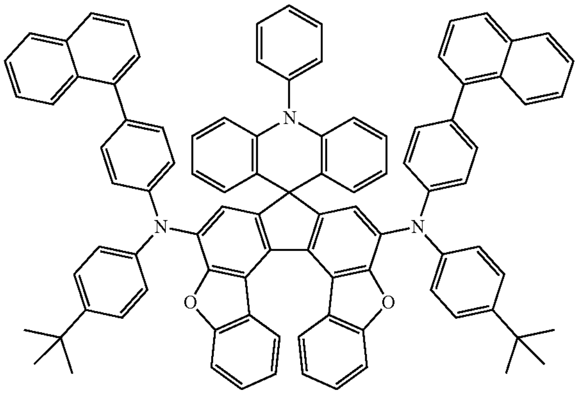
Compound 24
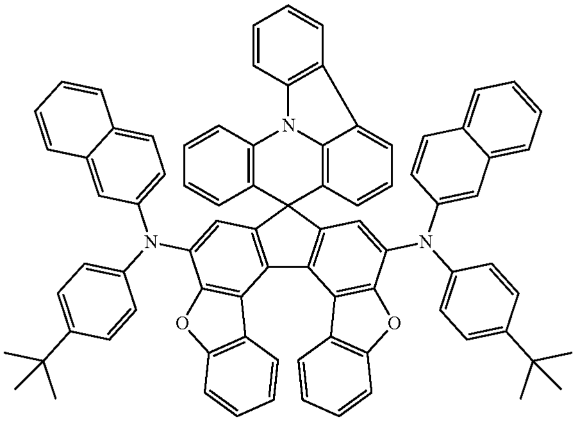
Compound 25
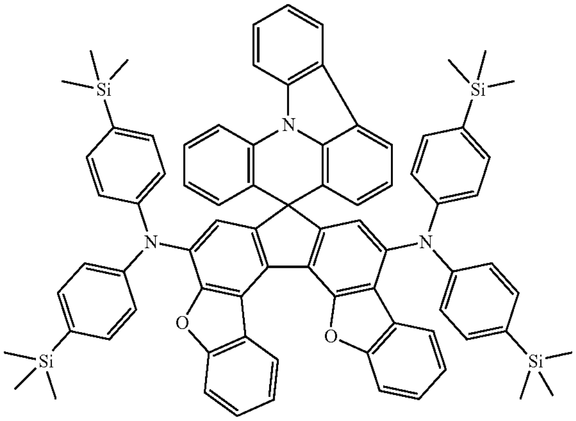

Compound 26
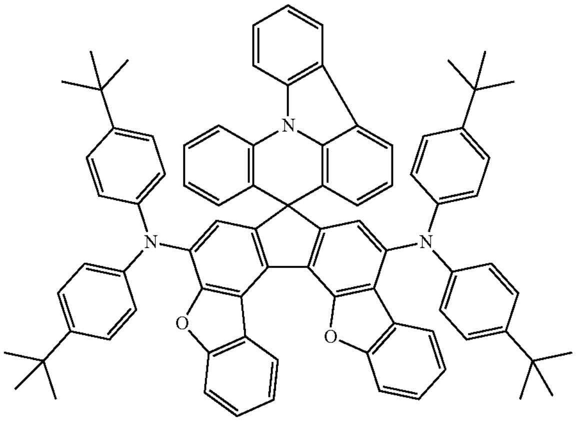
Compound 27
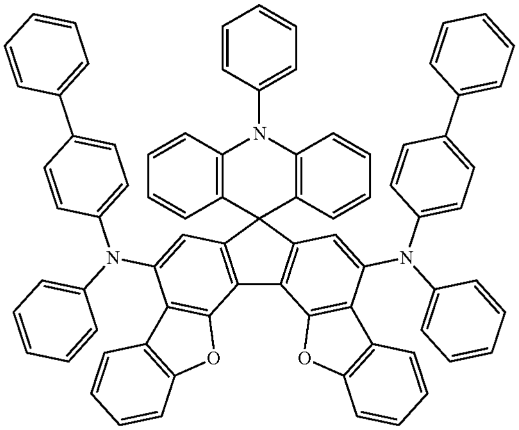
Compound 28
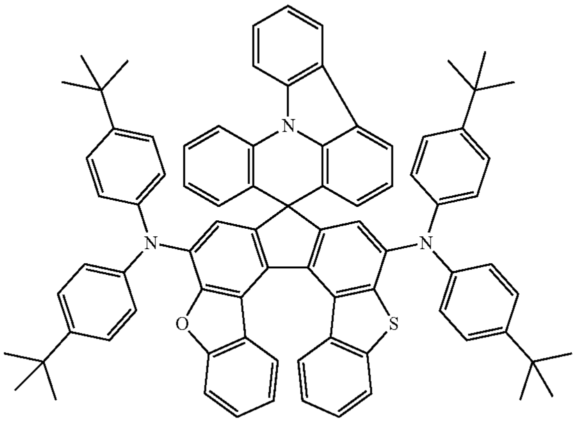
Compound 29
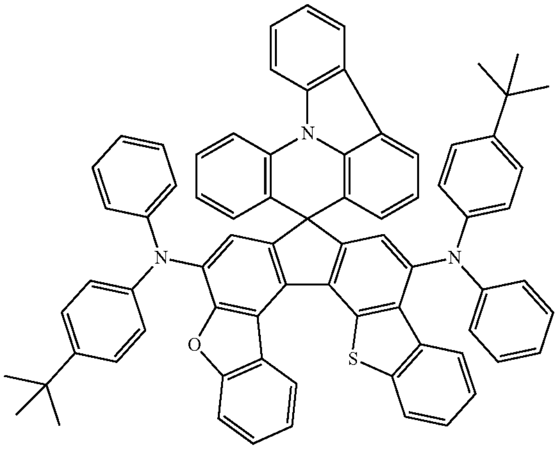
Compound 30
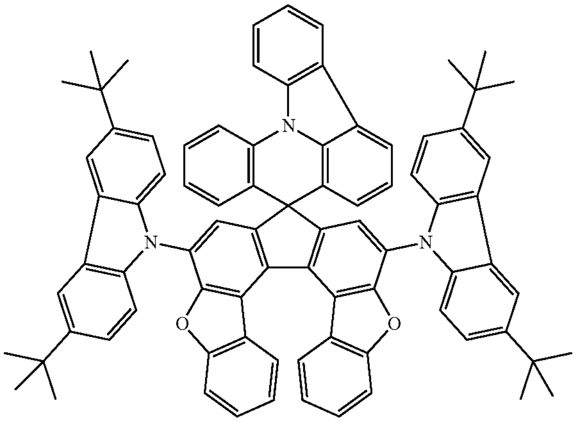
Compound 31
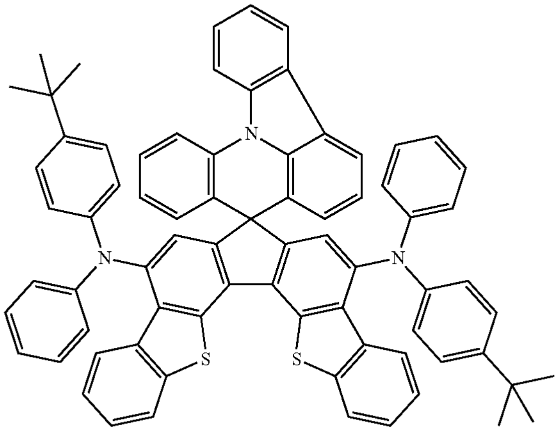

-continued
Compound 32
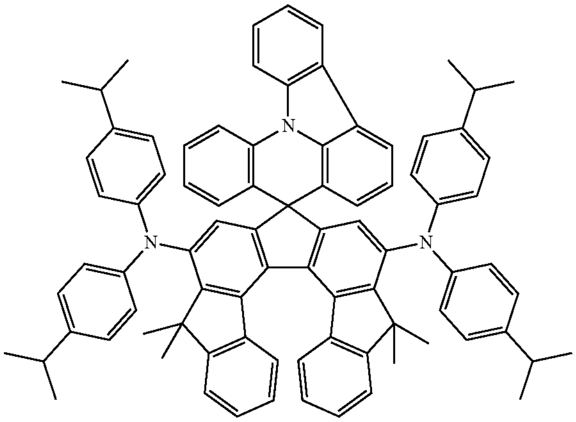
Compound 33
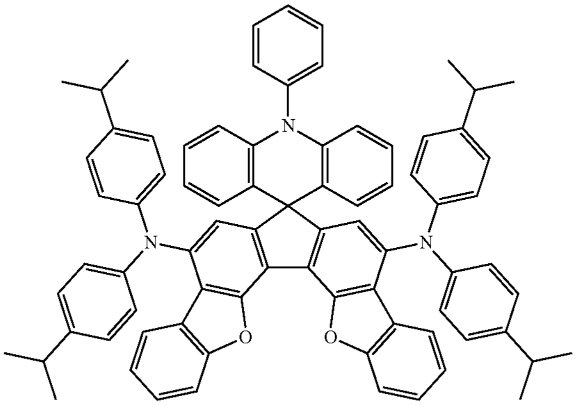
Compound 34
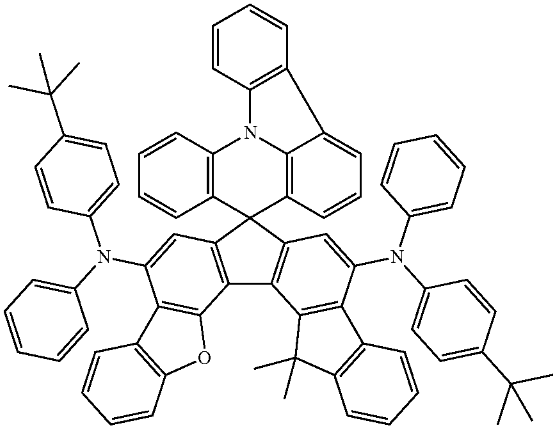
-continued
Compound 35
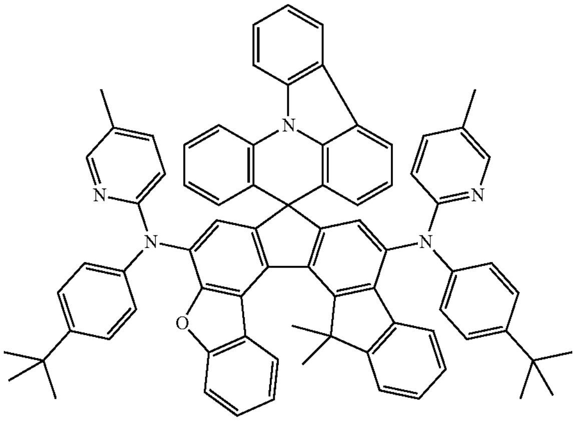
Compound 36
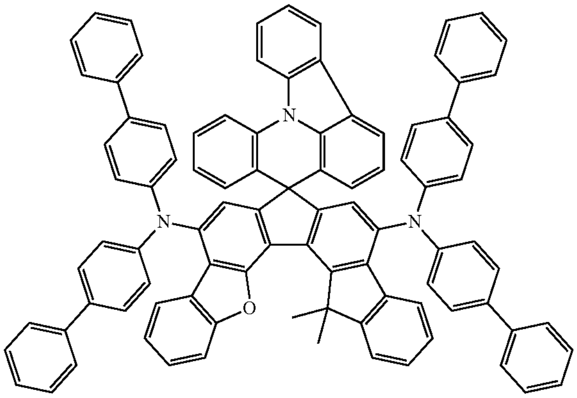
Compound 37
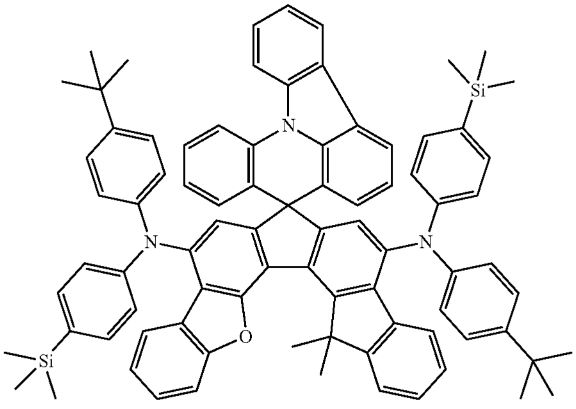

-continued
Compound 38
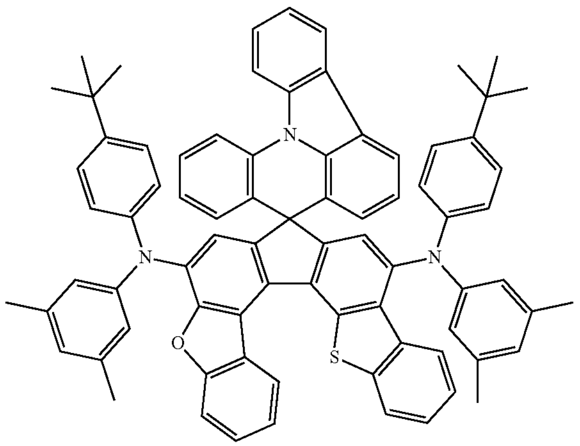
Compound 39
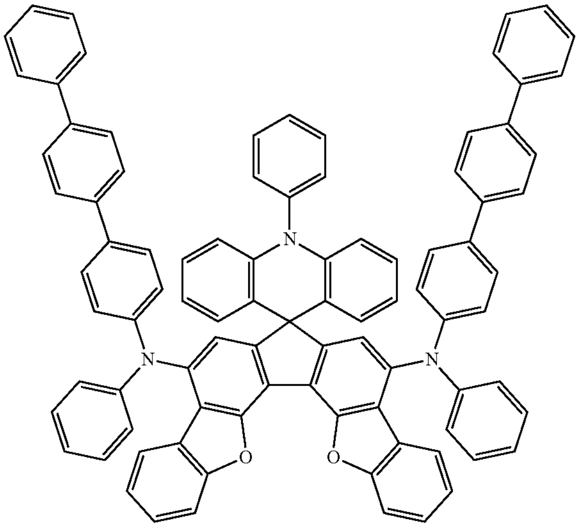
Compound 40
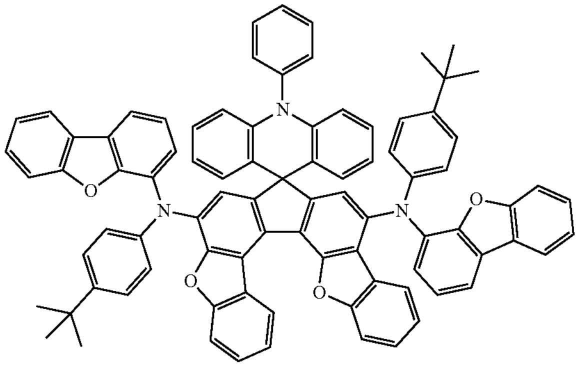
-continued
Compound 41
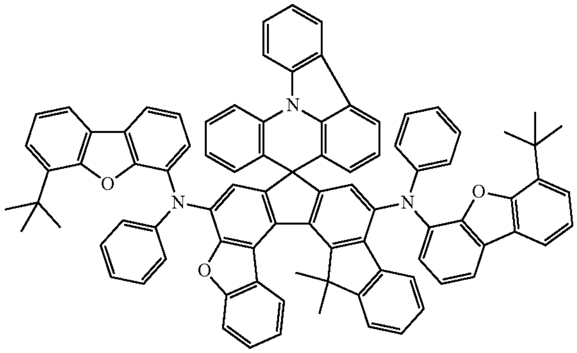
Compound 42
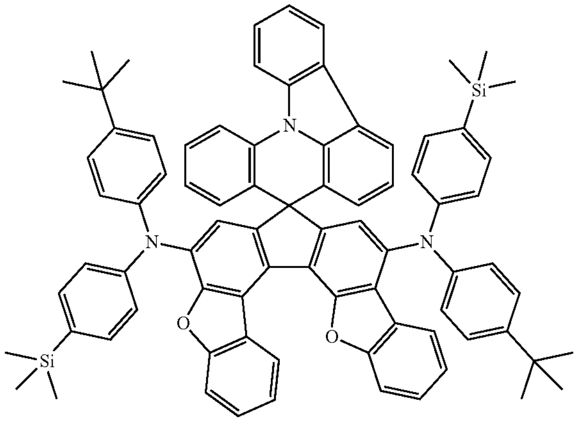
Coopound 43
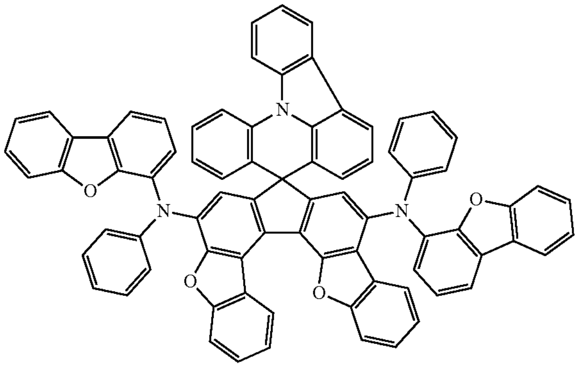
Compound 44
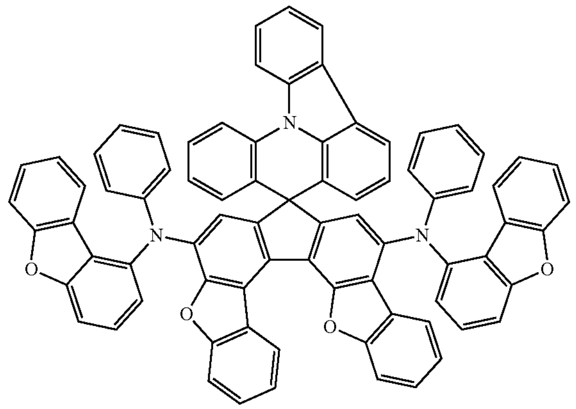

Compound 45
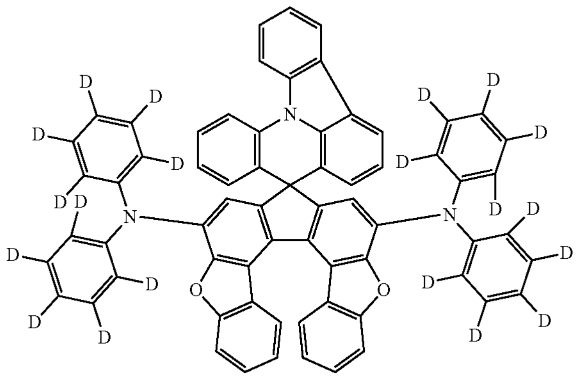
Compound 46
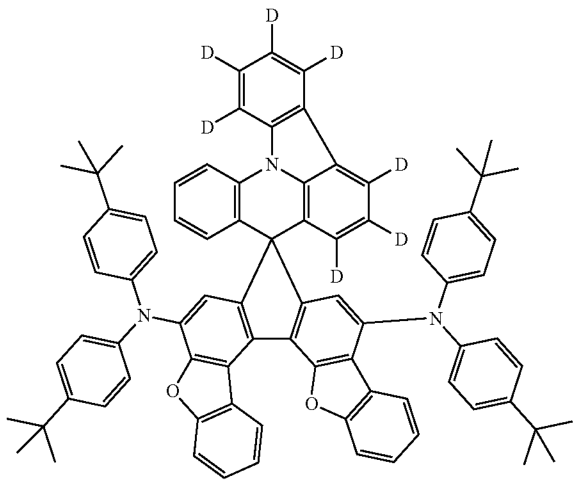
Compound 47
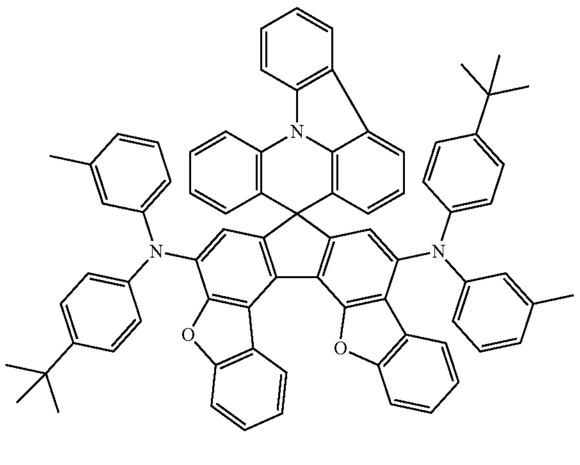
Compound 48
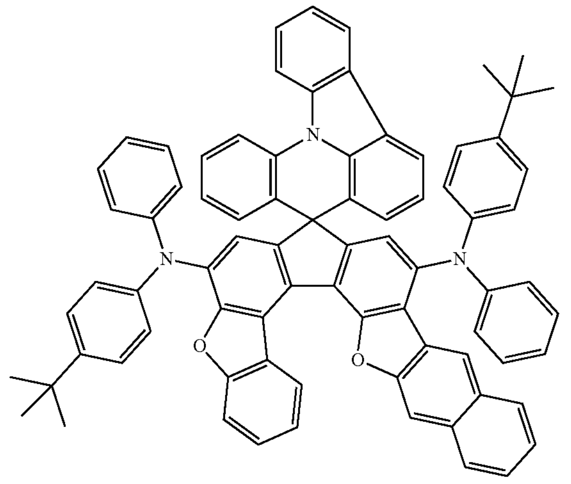
Compound 49
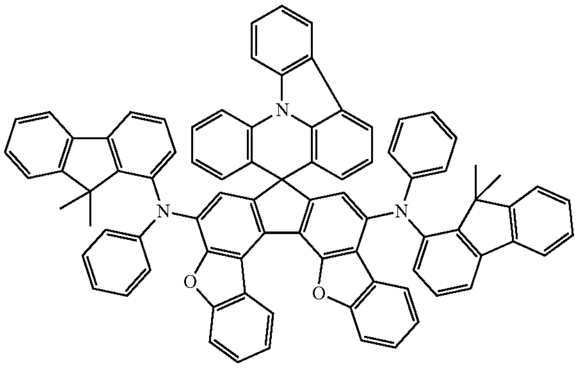
Compound 50
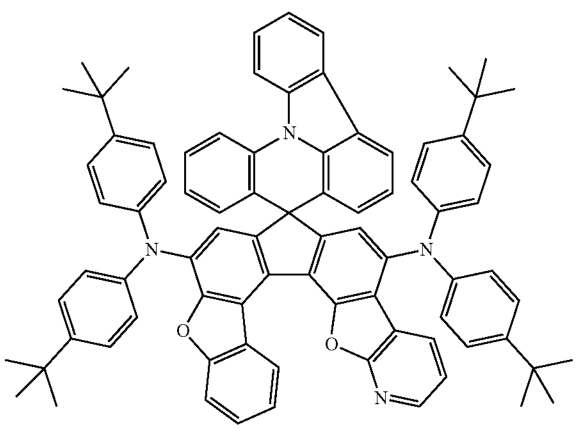

-continued
Compound 51
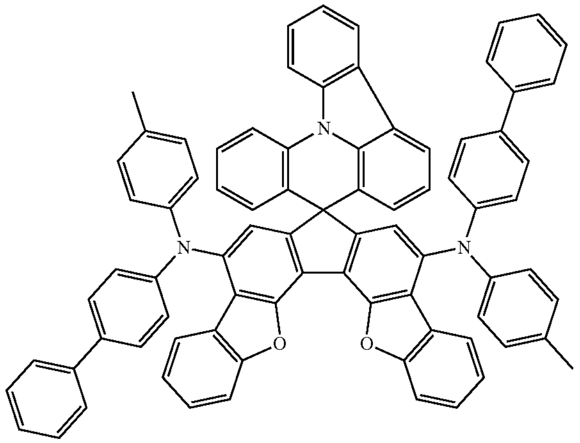
Compound 52
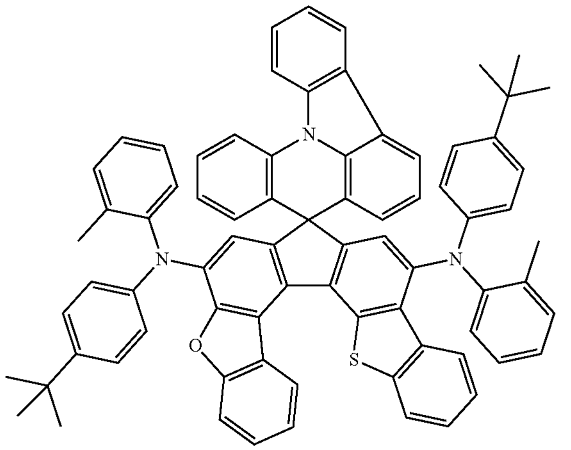
Compound 53
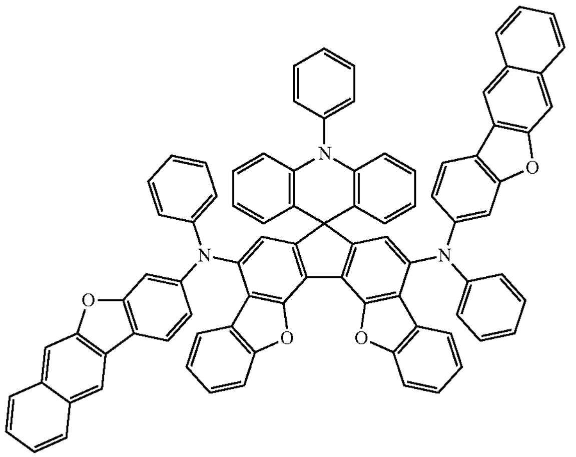
-continued
Compound 54
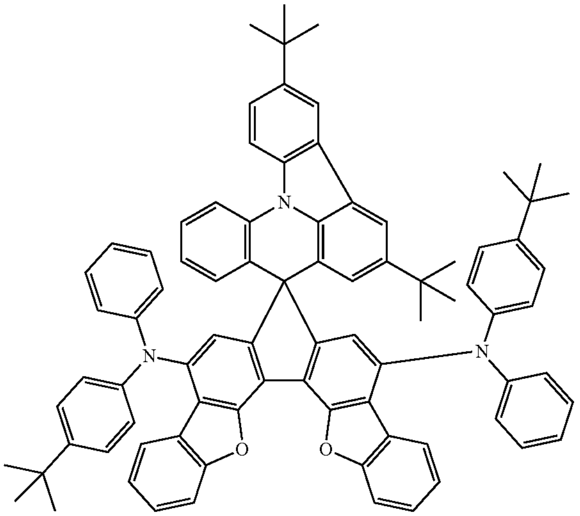
Compound 55
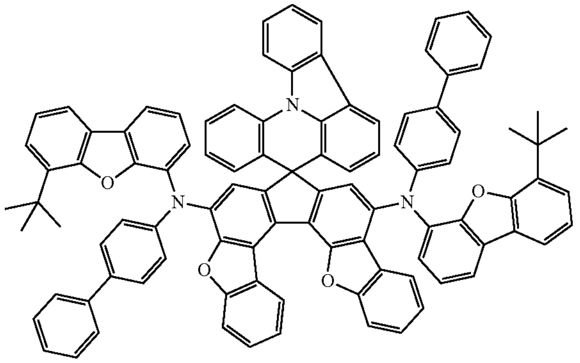
Compound 56
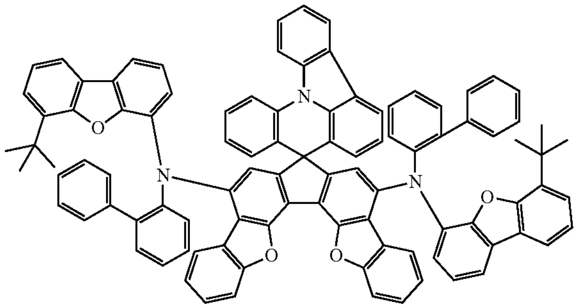

-continued
Compound 57
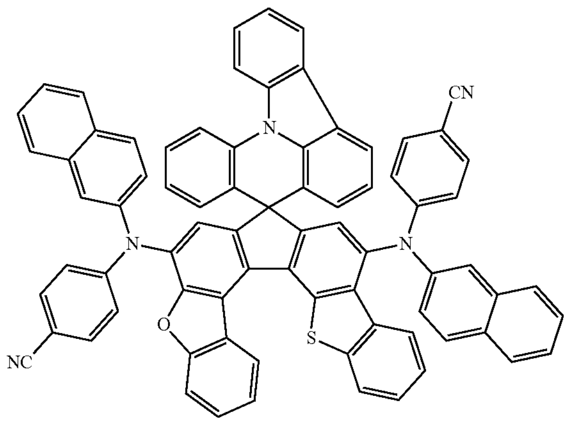
Compound 58
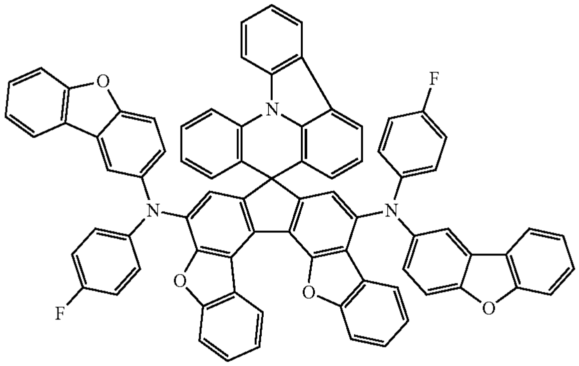
Compound 59
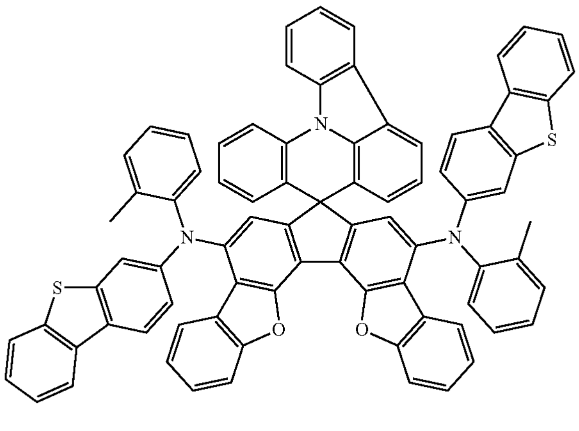
-continued
Compound 60
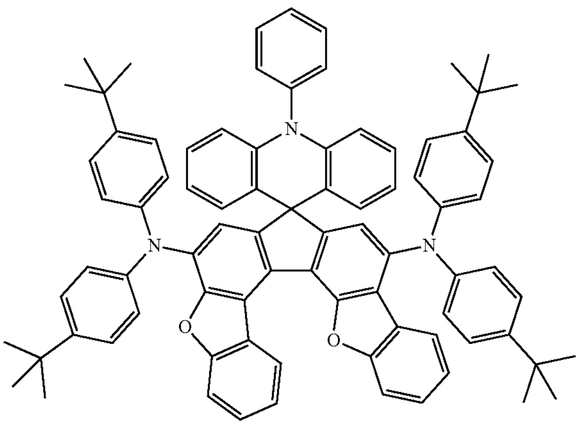
Compound 61
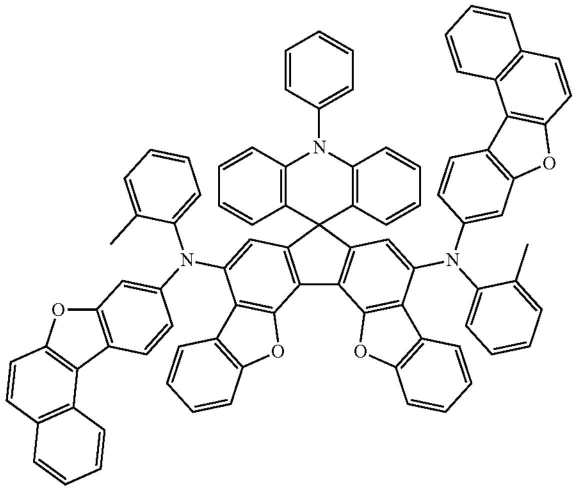
Compound 62
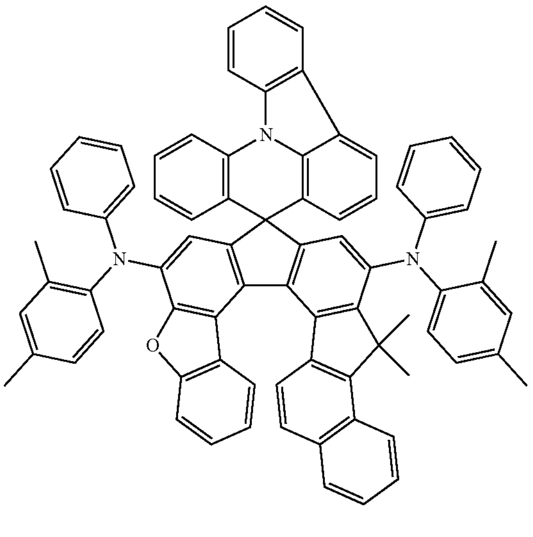

-continued

Compound 63

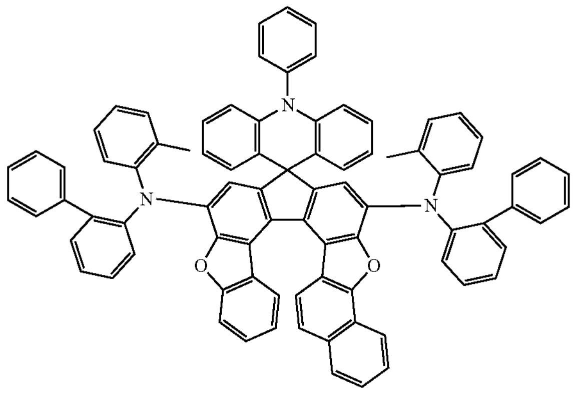

The compound according to an exemplary embodiment of the present specification may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

[General Preparation Method]

General Synthesis Method 1

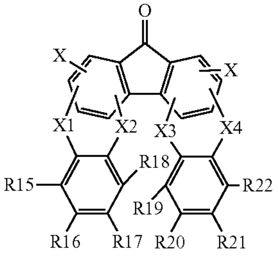

[Intermediate 1-1]

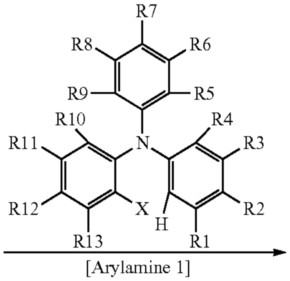

[Arylamine 1]

-continued

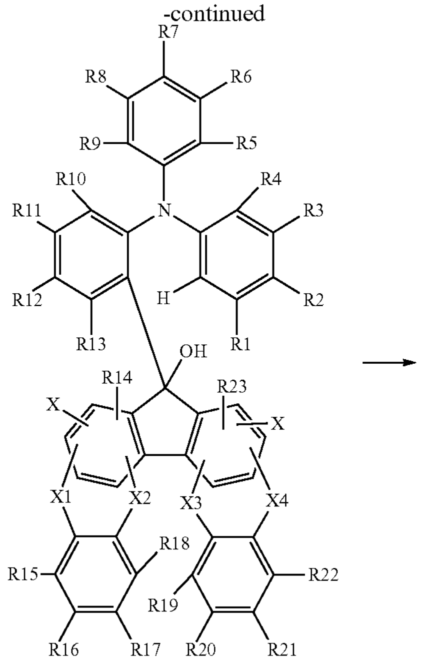

[Intermediate 1-2]

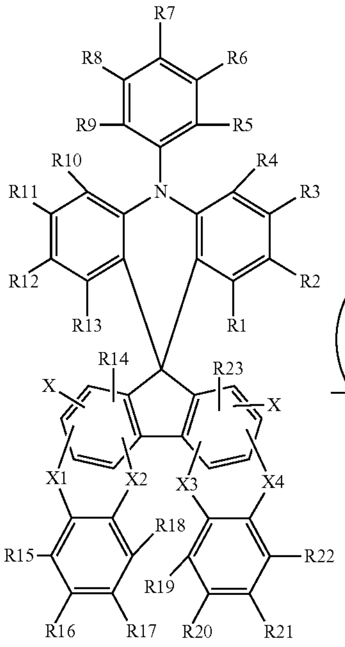

[Intermediate 1-3]

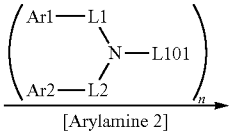

[Arylamine 2]

-continued

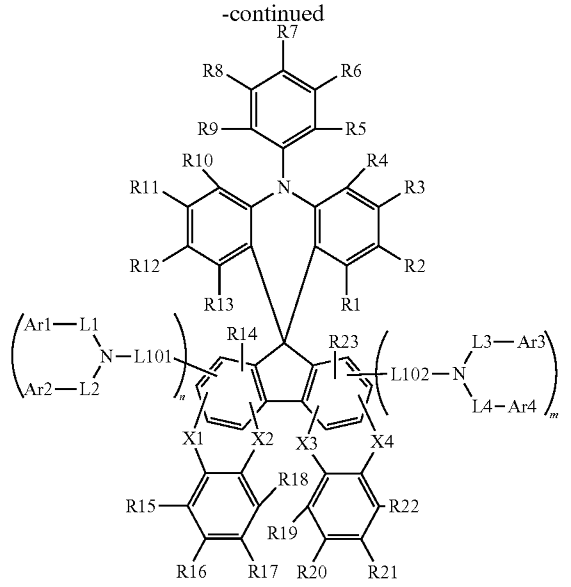

[Final Compound]

[Intermediate 1-2] is synthesized by using [Intermediate 1-1] and a base such as butyllithium to couple [Intermediate 1-1] to [Arylamine 1]. [Intermediate 1-3] may be obtained from the obtained [Intermediate 1-2] through a Spiro cyclization reaction under an acidic condition, and a final compound is synthesized by using an appropriate coupling reaction using [Arylamine 2] and a palladium catalyst from [Intermediate 1-3]. (In the formula, X is a halogen element such as Br, Cl, and I)

General Synthesis Method 2

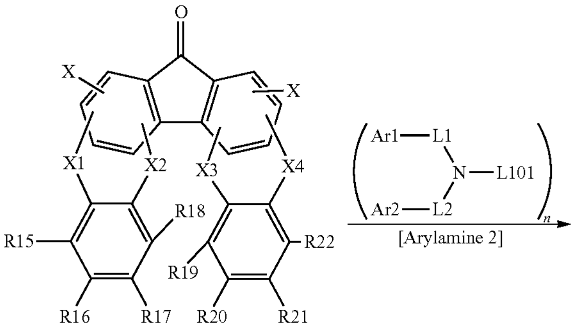

[Intermediate 1-1]

[Arylamine 2]

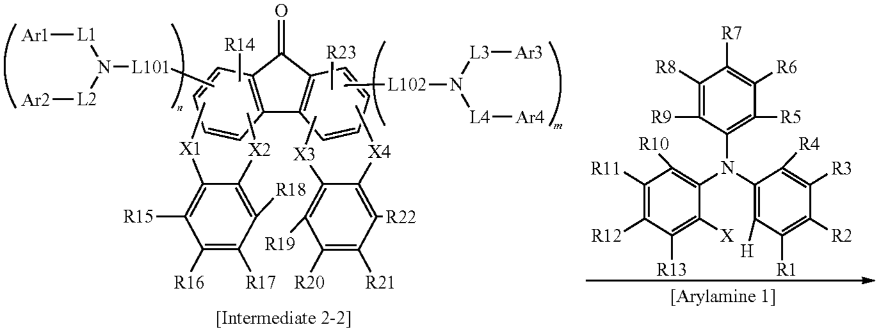

[Intermediate 2-2]

[Arylamine 1]

-continued

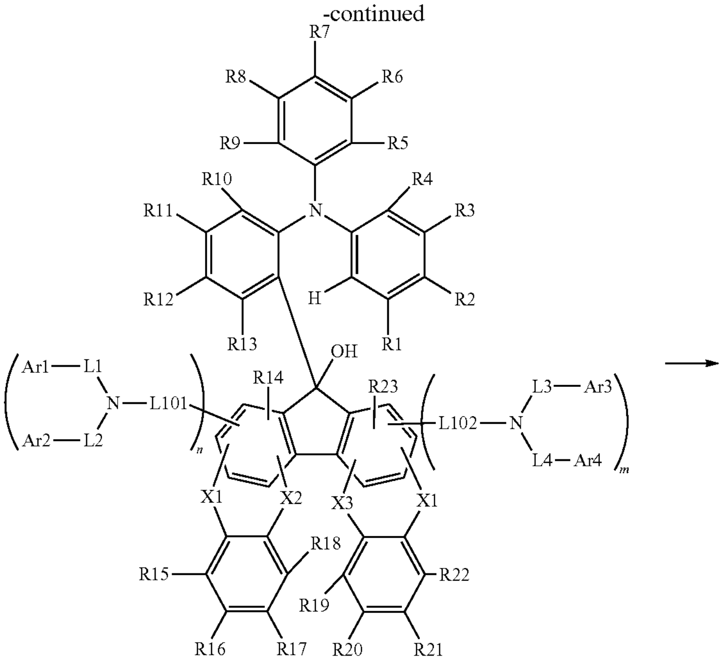

[Intermediate 2-3]

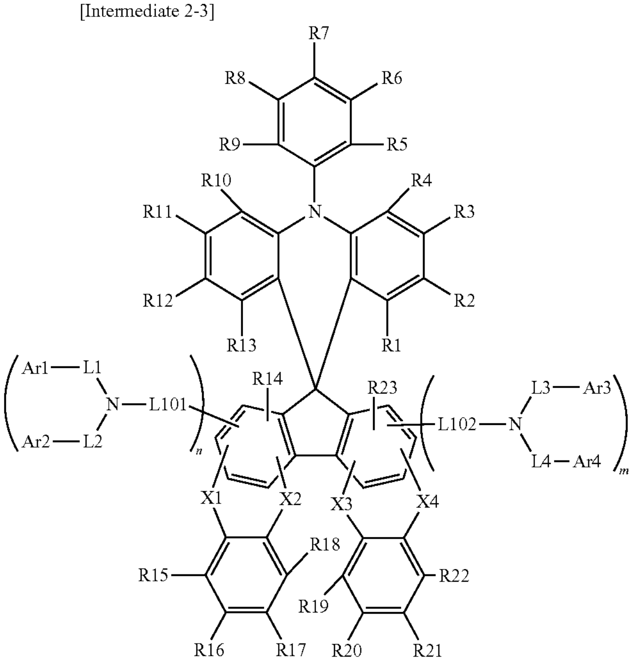

[Final Compound]

[Intermediate 1-1] is used and an appropriate coupling reaction using [Arylamine 2] and a palladium catalyst is used to synthesize [Intermediate 2-2], and [Intermediate 2-2] is coupled to [Arylamine 1] by using a base such as butyllithium, thereby synthesizing [Intermediate 2-3]. A final compound is synthesized from the obtained [Intermediate 2-3] through a spiro cyclization reaction under an acidic condition. (In the formula, X is a halogen element such as Br, Cl, and I)

Further, the present specification provides an organic light emitting device comprising the above-described compound.

An exemplary embodiment of the present specification provides an organic light emitting device comprising: a first electrode; a second electrode disposed to face the first electrode; and an organic material layer having one or more layers disposed between the first electrode and the second electrode, in which one or more layers of the organic material layer comprise the compound.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further included.

The organic material layer of the organic light emitting device of the present specification may also be composed of a single-layered structure, but may be composed of a multi-layered structure in which two or more organic material layers are stacked. For example, as a representative example of the organic electronic device of the present invention, an organic light emitting device may have a structure comprising a hole injection layer, a hole transporting layer, a light emitting layer, an electron transporting layer, an electron injection layer, an electron blocking layer, a hole blocking layer, and the like as organic material layers. However, the structure of the organic electronic device is not limited thereto, and may include a fewer number of organic layers.

According to an exemplary embodiment of the present specification, the organic light emitting device may be selected from the group consisting of an organic phosphorescent device, an organic solar cell, an organic photoconductor (OPC), and an organic transistor.

In an exemplary embodiment of the present specification, the organic material layer comprises a light emitting layer, and the light emitting layer comprises the compound.

In an exemplary embodiment of the present specification, the organic material layer comprises a hole injection layer or a hole transporting layer, and the hole injection layer or the hole transporting layer comprises the compound.

In an exemplary embodiment of the present specification, the organic material layer comprises an electron transporting layer or an electron injection layer, and the electron transporting layer or the electron injection layer comprises the compound.

In an exemplary embodiment of the present specification, the organic material layer comprises an electron blocking layer or a hole blocking layer, and the electron blocking layer or the hole blocking layer comprises the compound.

In an exemplary embodiment of the present specification, the organic light emitting device further comprises one or two or more layers selected from the group consisting of a hole injection layer, a hole transporting layer, a light emitting layer, an electron transporting layer, an electron injection layer, a hole blocking layer, and an electron blocking layer.

In an exemplary embodiment of the present specification, the organic light emitting device comprises a first electrode; a second electrode disposed to face the first electrode; a light emitting layer disposed between the first electrode and the second electrode; and an organic material layer having two or more layers disposed between the light emitting layer and the first electrode, or between the light emitting layer and the second electrode, in which at least one of two or more layers of the organic material layer comprises the compound.

In an exemplary embodiment of the present specification, as the organic material layer having two or more layers, two or more may be selected from the group consisting of a hole injection layer, a hole transporting layer, a layer which transports and injects holes simultaneously, an electron transporting layer, an electron injection layer, a layer which transports and injects electrons simultaneously, and a hole blocking layer.

In an exemplary embodiment of the present specification, the organic material layer comprises an electron transporting layer having two or more layers, and at least one of two or more layers of the electron transporting layer comprises the compound. Specifically, in an exemplary embodiment of the present specification, the compound may also be included in one layer of two or more layers of the electron transporting layer, and may be included in each layer of two or more layers of the electron transporting layer.

In addition, in an exemplary embodiment of the present specification, when the compound is comprised in each layer of two or more layers of the electron transporting layer, the other materials except for the compound may be the same as or different from each other.

In an exemplary embodiment of the present specification, the organic material layer further comprises a hole injection layer or a hole transporting layer, which comprises a compound comprising an arylamino group, a carbazolyl group, or a benzocarbazolyl group, in addition to the organic material layer comprising the compound.

In another exemplary embodiment, the organic light emitting device may be an organic light emitting device having a normal type structure in which a positive electrode, an organic material layer having one or more layers, and a negative electrode are sequentially stacked on a substrate.

When the organic material layer including the compound of Chemical Formula 1 is an electron transporting layer, the electron transporting layer may further comprise an n-type dopant. As the n-type dopant, those known in the art may be used, and for example, a metal or a metal complex may be used. According to an example, the electron transporting layer comprising the compound of Chemical Formula 1 may further comprise LiQ.

In still another exemplary embodiment, the organic light emitting device may be an organic light emitting device having an inverted type structure in which a negative electrode, an organic material layer having one or more layers, and a positive electrode are sequentially stacked on a substrate.

For example, the structure of the organic light emitting device of the present specification may have a structure as illustrated in FIGS. 1 and 2, but is not limited thereto.

FIG. 1 exemplifies the structure of an organic light emitting device (10) in which a first electrode (30), a light emitting layer (40), and a second electrode (50) are sequentially stacked on a substrate (20). FIG. 1 is an exemplified structure of the organic light emitting device according to an exemplary embodiment of the present specification, and may further comprise other organic material layers.

FIG. 2 exemplifies the structure of an organic light emitting device in which a first electrode (30), a hole injection layer (60), a hole transporting layer (70), an electron blocking layer (80), a light emitting layer (40), an electron transporting layer (90), an electron injection layer (100), and a second electrode (50) are sequentially stacked on a substrate (20). FIG. 2 is an exemplified structure according to another exemplary embodiment of the present specification, and may further comprise other organic material layers.

The organic light emitting device of the present specification may be manufactured by the materials and methods known in the art, except that one or more layers of the organic material layer comprise the compound of the present specification, that is, the compound.

When the organic light emitting device comprises a plurality of organic material layers, the organic material layers may be formed of the same material or different materials.

The organic light emitting device of the present specification may be manufactured by the materials and methods known in the art, except that one or more layers of the organic material layer comprise the compound, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a high work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The electron blocking layer is a layer which may improve the service life and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

A light emitting material for the light emitting layer is a material which may emit light in a visible light region by accepting and combining holes and electrons from a hole transporting layer and an electron transporting layer, respectively, and is preferably a material having good quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; polyp-phenylenevinylene) (PPV)-based polymers; spiro compounds; polyfluorene, lubrene, and the like, but are not limited thereto.

The light emitting layer may comprise a host material and a dopant material. Examples of the host material comprise a fused aromatic ring derivative, or a hetero ring-containing compound, and the like. Specific examples of the fused aromatic ring derivative comprise an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

It is possible to comprise a structure of the following Chemical Formula 1A as a material for a host of the light emitting layer of the organic material layers of the organic light emitting device of the present specification.

[Chemical Formula 1A]

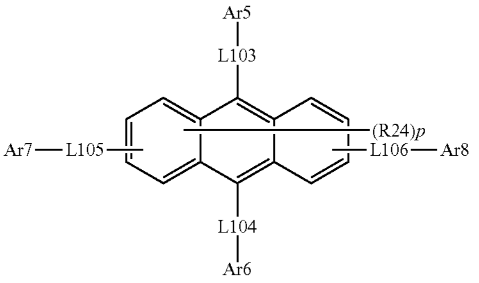

In Chemical Formula 1A,

L103 to L106 are the same as or different from each other, and are each independently a direct bond; a substituted or unsubstituted arylene group; or a substituted or unsubstituted heteroarylene group, Ar5 to Ar8 are the same as or different from each other, and are each independently a substituted or unsubstituted aryl group; or a substituted or unsubstituted heteroaryl group, R24s are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, p is an integer from 0 to 6, and when p is 2 or more, substituents in the parenthesis are the same as or different from each other.

In an exemplary embodiment of the present specification, L103 to L106 are the same as or different from each other, and are each independently a direct bond; a substituted or unsubstituted arylene group having 6 to 60 carbon atoms; or a substituted or unsubstituted heteroarylene group having 2 to 60 carbon atoms.

In an exemplary embodiment of the present specification, L103 to L106 are the same as or different from each other, and are each independently a direct bond; a substituted or unsubstituted arylene group having 6 to 40 carbon atoms; or a substituted or unsubstituted heteroarylene group having 2 to 40 carbon atoms.

According to another exemplary embodiment, L103 to L106 are the same as or different from each other, and are each independently a direct bond; a substituted or unsubstituted phenylene group; a substituted or unsubstituted biphenylylene group; a substituted or unsubstituted terphenylene group; a substituted or unsubstituted naphthylene group; a substituted or unsubstituted anthracenylene group; a substituted or unsubstituted phenanthrenylene group; a substituted or unsubstituted triphenylene group; a substituted or unsubstituted fluorenyl group; a substituted or unsubstituted thiophenylene group; a substituted or unsubstituted furanylene group; a substituted or unsubstituted dibenzothiophenylene group; a substituted or unsubstituted dibenzofuranylene group; or a substituted or unsubstituted carbazolylene group.

In another exemplary embodiment, L103 to L106 are the same as or different from each other, and are each independently a direct bond; a phenylene group; a biphenylylene group; a terphenylene group; a naphthylene group; an anthracenylene group; a phenanthrenylene group; a triphenylene group; a fluorenyl group unsubstituted or substituted with a methyl group or a phenyl group; a thiophenylene group; a furanylene group; a dibenzothiophenylene group; a dibenzofuranylene group; or a carbazolylene group unsubstituted or substituted with an ethyl group or a phenyl group.

According to still another exemplary embodiment, L103 to L106 are the same as or different from each other, and may be each independently a direct bond or selected from the following structures.

LB1

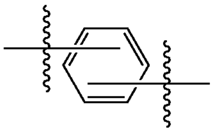

LB2

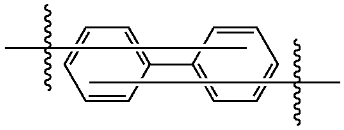

LB3

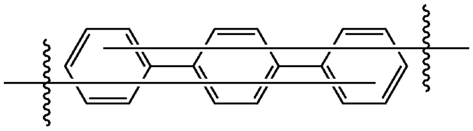

LB4

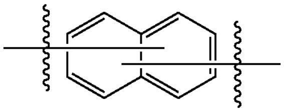

LB5

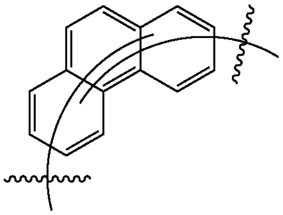

LB6

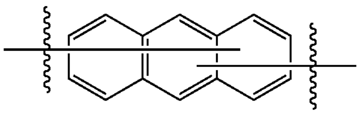

LB7

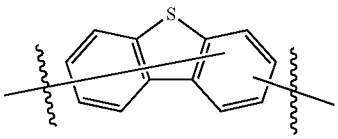

LB8

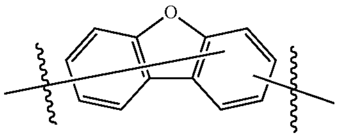

LB9

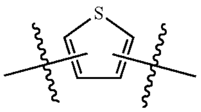

-continued

LB10

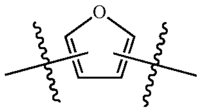

LB11

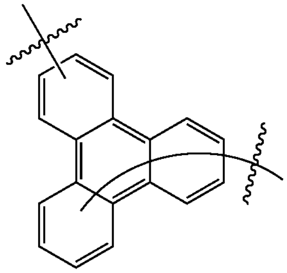

LB12

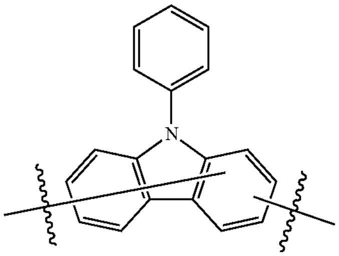

LB13

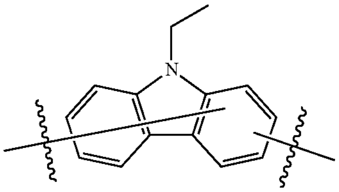

LB14

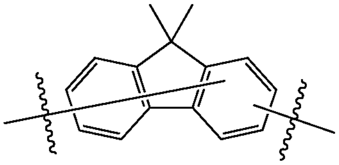

LB15

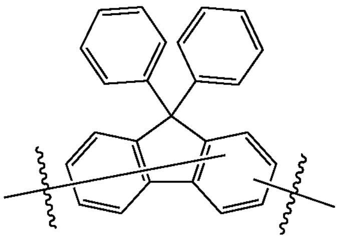

According to an exemplary embodiment of the present specification, L103 is a direct bond.

According to an exemplary embodiment of the present specification, L104 is a phenylene group.

According to an exemplary embodiment of the present specification, L105 and L106 are a direct bond.

In an exemplary embodiment of the present specification, R24's are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heterocyclic group.

In an exemplary embodiment of the present specification, R24's are the same as or different from each other, and are each independently hydrogen; deuterium; a substituted or unsubstituted alkyl group having 1 to 50 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 40 carbon atoms.

In an exemplary embodiment of the present specification, R24's are the same as or different from each other, and are each independently hydrogen; deuterium; a substituted or unsubstituted alkyl group having 1 to 30 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 25 carbon atoms.

In another exemplary embodiment, R24 is hydrogen. According to an exemplary embodiment of the present specification, p is 0 or 1.

In an exemplary embodiment of the present specification, Ar5 to Ar8 are the same as or different from each other, and are each independently hydrogen; a substituted or unsubstituted aryl group having 6 to 60 carbon atoms; or a substituted or unsubstituted heteroaryl group having 2 to 60 carbon atoms.

According to another exemplary embodiment, Ar5 to Ar8 are the same as or different from each other, and are each independently hydrogen; an aryl group having 6 to 60 carbon atoms, which is unsubstituted or substituted with an aryl group having 6 to 60 carbon atoms or a heteroaryl group having 2 to 60 carbon atoms; or a heteroaryl group having 2 to 60 carbon atoms, which is unsubstituted or substituted with an aryl group having to 60 carbon atoms or a heteroaryl group having 2 to 60 carbon atoms.

In another exemplary embodiment, Ar5 to Ar8 are the same as or different from each other, and are each independently hydrogen; a substituted or unsubstituted phenyl group; a substituted or unsubstituted biphenyl group; a substituted or unsubstituted naphthyl group; a substituted or unsubstituted phenanthrene group; a substituted or unsubstituted anthracene group; a substituted or unsubstituted triphenylene group; a substituted or unsubstituted dibenzofuran group; a substituted or unsubstituted naphthobenzofuran group; a substituted or unsubstituted dibenzothiophene group; a substituted or unsubstituted carbazole group; a substituted or unsubstituted fluorene group; a substituted or unsubstituted thiophene group; a substituted or unsubstituted furan group; a substituted or unsubstituted benzothiophene group; a substituted or unsubstituted benzofuran group; a substituted or unsubstituted benzocarbazole group; a substituted or unsubstituted benzofluorene group; a substituted or unsubstituted indole carbazole group; a substituted or unsubstituted pyridyl group; a substituted or unsubstituted isoquinolyl group; a substituted or unsubstituted quinolyl group; a substituted or unsubstituted quinazolyl group; a substituted or unsubstituted triazine group; a substituted or unsubstituted benzimidazole group; a substituted or unsubstituted benzoxazole group; a substituted or unsubstituted benzothiazole group; a substituted or unsubstituted dihydroacridine group; a substituted or unsubstituted xanthene group; or a substituted or unsubstituted dibenzosilole group.

In still another exemplary embodiment, Ar5 to Ar8 are the same as or different from each other, and are each independently hydrogen; a phenyl group; a biphenyl group; a naphthyl group unsubstituted or substituted with an aryl group; a phenanthrene group; an anthracene group; a triphenylene group; a dibenzofuran group unsubstituted or substituted with an aryl group; a naphthobenzofuran group; a dibenzothiophene group unsubstituted or substituted with an aryl group; a carbazole group unsubstituted or substituted with an alkyl group or an aryl group; a fluorene group unsubstituted or substituted with an alkyl group or an aryl group; a thiophene group unsubstituted or substituted with an aryl group; a furan group unsubstituted or substituted with an aryl group; a benzothiophene group; a benzofuran group; a benzocarbazole group unsubstituted or substituted with an alkyl group or an aryl group; a benzofluorene group unsubstituted or substituted with an alkyl group or an aryl group; an indole carbazole group; a pyridyl group; an isoquinolyl group unsubstituted or substituted with an aryl group; a quinolyl group; a quinazolyl group unsubstituted or substituted with an aryl group; a triazine group unsubstituted or substituted with an aryl group; a benzimidazole group unsubstituted or substituted with an aryl group; a benzoxazole group unsubstituted or substituted with an aryl group; a benzothiazole group unsubstituted or substituted with an aryl group; a dihydroacridine group unsubstituted or substituted with an alkyl group or an aryl group; a xanthene group unsubstituted or substituted with an alkyl group or an aryl group; or a dibenzosilole group unsubstituted or substituted with an alkyl group or an aryl group.

In yet another exemplary embodiment, Ar5 to Ar8 are the same as or different from each other, and are each independently hydrogen; a phenyl group; a biphenyl group; a naphthyl group unsubstituted or substituted with a phenyl group; a phenanthrene group; an anthracene group; a triphenylene group; a dibenzofuran group unsubstituted or substituted with a phenyl group; a naphthobenzofuran group; a dibenzothiophene group unsubstituted or substituted with a phenyl group; a carbazole group unsubstituted or substituted with a methyl group, an ethyl group, or a phenyl group; a fluorene group unsubstituted or substituted with a methyl group or a phenyl group; a thiophene group unsubstituted or substituted with a phenyl group; a furan group unsubstituted or substituted with a phenyl group; a benzothiophene group; a benzofuran group; a benzocarbazole group unsubstituted or substituted with a methyl group or a phenyl group; a benzofluorene group unsubstituted or substituted with a methyl group or a phenyl group; an indole carbazole group; a pyridyl group unsubstituted or substituted with a phenyl group or a naphthyl group; an isoquinolyl group unsubstituted or substituted with a phenyl group; a quinolyl group; a quinazolyl group unsubstituted or substituted with a phenyl group; a triazine group unsubstituted or substituted with a phenyl group; a benzimidazole group unsubstituted or substituted with a phenyl group; a benzoxazole group unsubstituted or substituted with a phenyl group; a benzothiazole group unsubstituted or substituted with a phenyl group; a dihydroacridine group unsubstituted or substituted with a methyl group or a phenyl group; a xanthene group unsubstituted or substituted with a methyl group or a phenyl group; or a dibenzosilole group unsubstituted or substituted with a methyl group or a phenyl group.

In an exemplary embodiment of the present specification, Ar5 to Ar8 are the same as or different from each other, and may be each independently hydrogen or selected from the following structures.

RA1

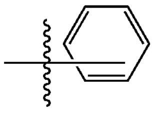

-continued

RA2

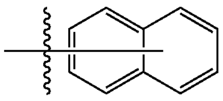

RA3

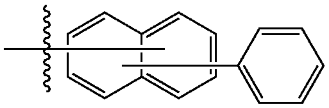

RA4

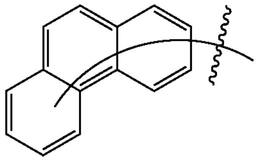

RA5

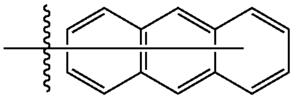

RA6

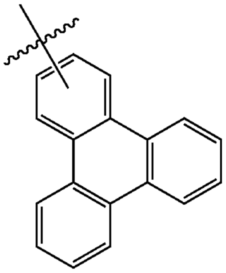

RA7

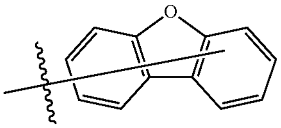

RA8

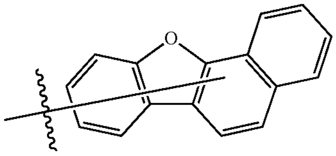

RA9

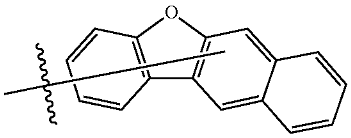

RA10

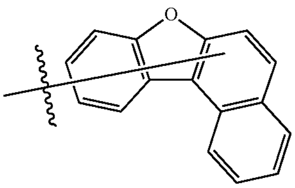

RA11

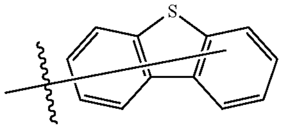

-continued
RA12
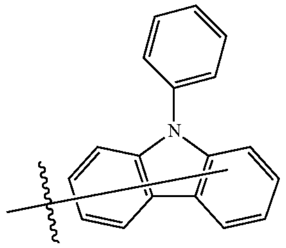
RA13
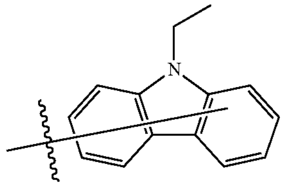
RA14
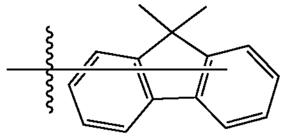
RA15
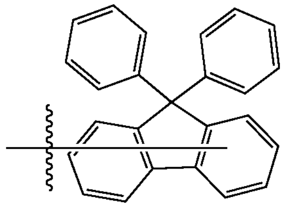
RA16
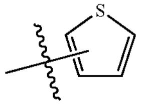
RA17
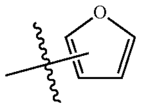
RA18
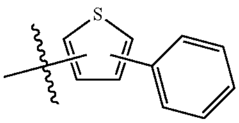
RA19
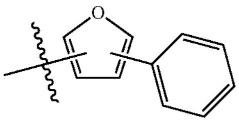
RA20
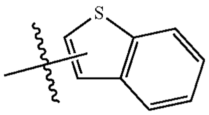
RA21
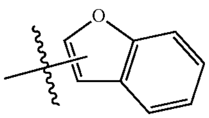
-continued
RA22
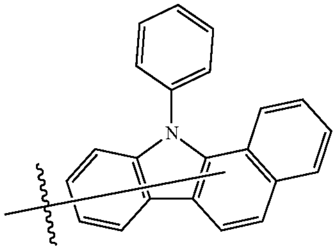
RA23
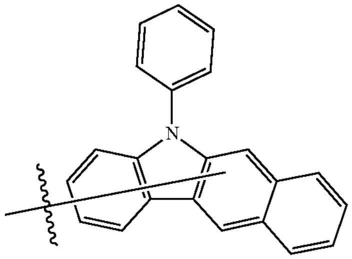
RA24
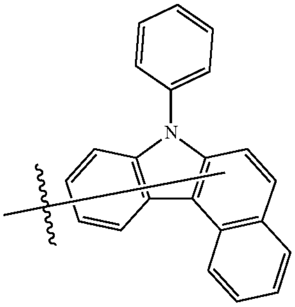
RA25
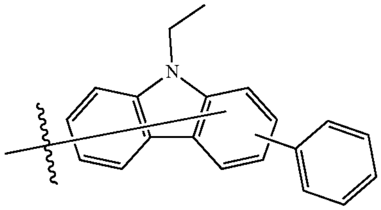
RA26
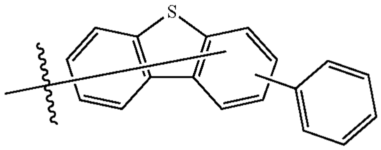
RA27
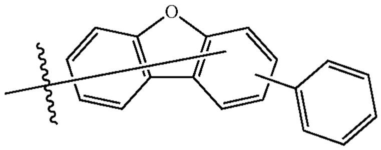
RA28
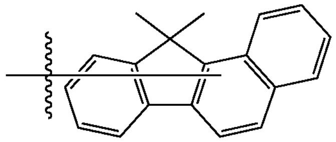

-continued
RA29
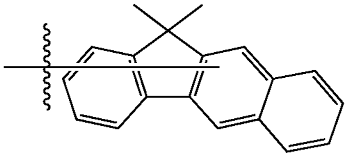
RA30
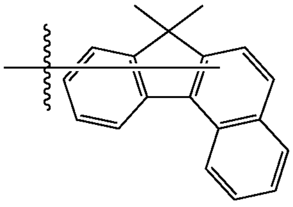
RA31
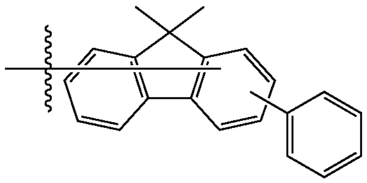
RA32
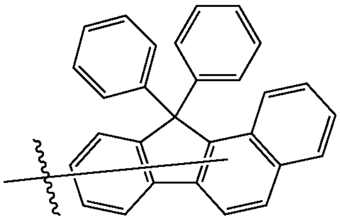
RA33
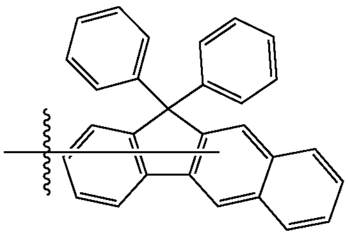
RA34
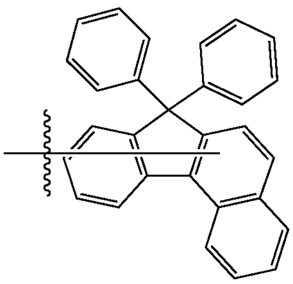
RA35
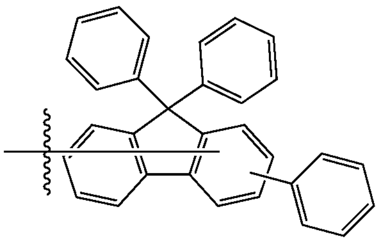
-continued
RA36
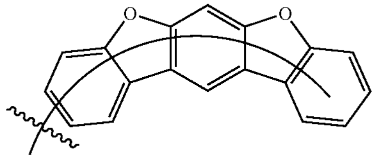
RA37
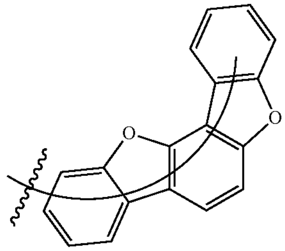
RA38
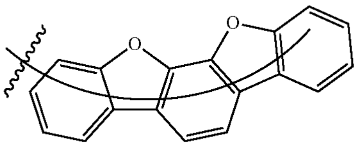
RA39
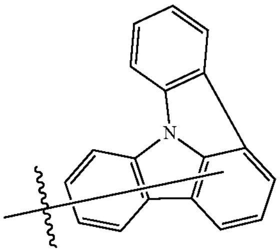
RA40
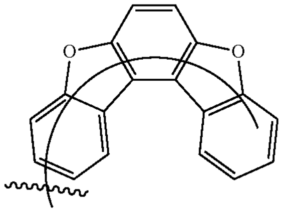
RA41
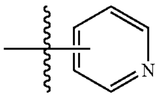
RA42
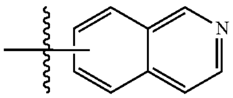
RA43
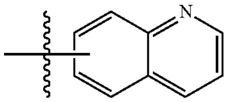
RA44
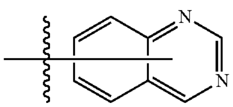

-continued
RA45
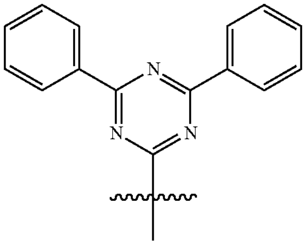
RA46
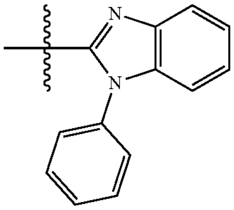
RA47
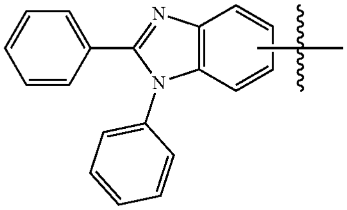
RA48
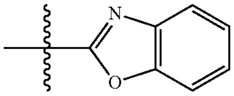
RA49
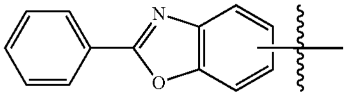
RA50
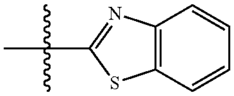
RA51
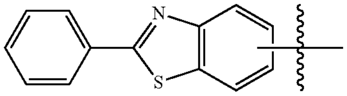
RA52
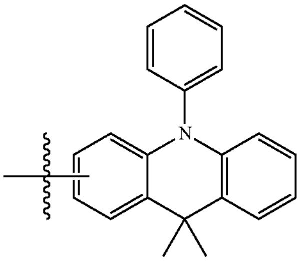
RA53
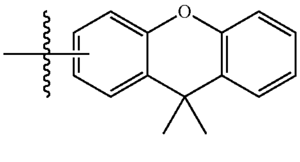
-continued
RA54
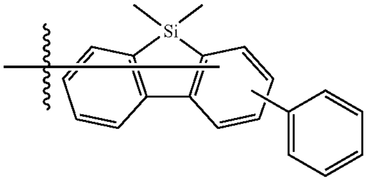
RA55
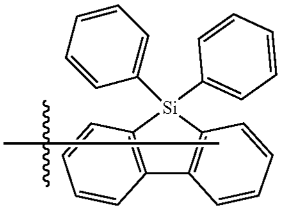
RA56
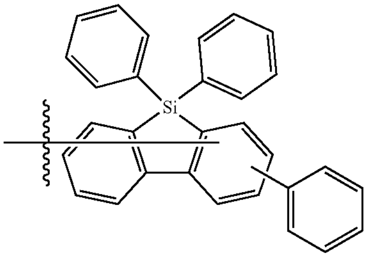
RA57
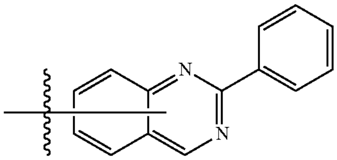
RA58
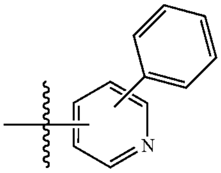
RA59
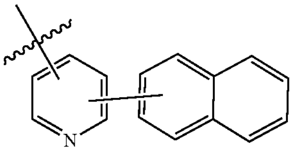
RA60
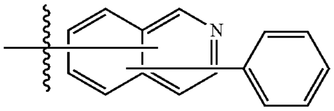
It is possible to include a structure of the following Chemical Formula 1B as a material for a host of the light emitting layer of the organic material layers of the organic light emitting device of the present specification.

[Chemical Formula 1B]

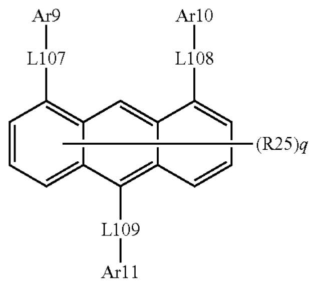

In Chemical Formula 1B,

L107 to L109 are the same as or different from each other, and are each independently a direct bond; a substituted or unsubstituted arylene group; or a substituted or unsubstituted heteroarylene group, Ar9 and Ar10 are the same as or different from each other, and are each independently a substituted or unsubstituted aryl group; or a substituted or unsubstituted heteroaryl group, R25s are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, q is an integer from 0 to 7, and when q is 2 or more, substituents in the parenthesis are the same as or different from each other.

In an exemplary embodiment of the present specification, R25's are the same as or different from each other, and are each independently hydrogen; deuterium; a substituted or unsubstituted alkyl group; a substituted or unsubstituted cycloalkyl group; a substituted or unsubstituted aryl group; or a substituted or unsubstituted heterocyclic group.

In an exemplary embodiment of the present specification, R25's are the same as or different from each other, and are each independently hydrogen; deuterium; a substituted or unsubstituted alkyl group having 1 to 50 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 40 carbon atoms.

In an exemplary embodiment of the present specification, R25's are the same as or different from each other, and are each independently hydrogen; deuterium; a substituted or unsubstituted alkyl group having 1 to 30 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 25 carbon atoms.

In another exemplary embodiment, R25 is hydrogen.

According to an exemplary embodiment of the present specification, q is 0 or 1.

In an exemplary embodiment of the present specification, L107 to L109 are the same as or different from each other, and are each independently a direct bond; a substituted or unsubstituted arylene group having 6 to 60 carbon atoms; or a substituted or unsubstituted heteroarylene group having 2 to 60 carbon atoms.

In an exemplary embodiment of the present specification, L107 to L109 are the same as or different from each other, and are each independently a direct bond; a substituted or unsubstituted arylene group having 6 to 40 carbon atoms; or a substituted or unsubstituted heteroarylene group having 2 to 40 carbon atoms.

According to another exemplary embodiment, L107 to L109 are the same as or different from each other, and are each independently a direct bond; a substituted or unsubstituted phenylene group; a substituted or unsubstituted biphenylylene group; a substituted or unsubstituted terphenylene group; a substituted or unsubstituted naphthylene group; a substituted or unsubstituted anthracenylene group; a substituted or unsubstituted phenanthrenylene group; a substituted or unsubstituted triphenylene group; a substituted or unsubstituted fluorenyl group; a substituted or unsubstituted thiophenylene group; a substituted or unsubstituted furanylene group; a substituted or unsubstituted dibenzothiophenylene group; a substituted or unsubstituted dibenzofuranylene group; or a substituted or unsubstituted carbazolylene group.

In still another exemplary embodiment, L107 to L109 are the same as or different from each other, and are each independently a direct bond; a phenylene group; a biphenylylene group; a terphenylene group; a naphthylene group; an anthracenylene group; a phenanthrenylene group; a triphenylene group; a fluorenyl group unsubstituted or substituted with a methyl group or a phenyl group; a thiophenylene group; a furanylene group; a dibenzothiophenylene group; a dibenzofuranylene group; or a carbazolylene group unsubstituted or substituted with an ethyl group or a phenyl group.

According to yet another exemplary embodiment, L107 to L109 are the same as or different from each other, and may be each independently a direct bond or selected from the following structures.

LC1

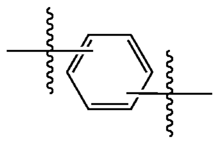

LC2

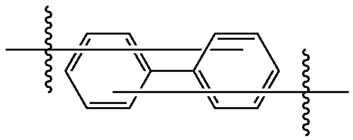

LC3

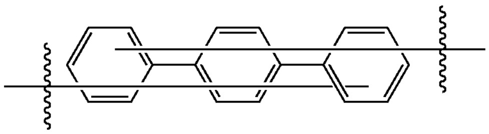

LC4

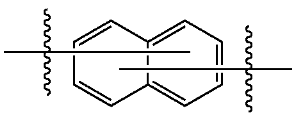

LC5

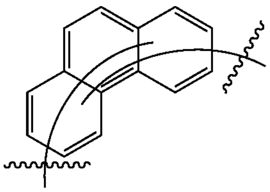

-continued

LC6

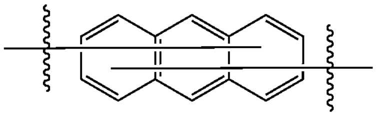

LC7

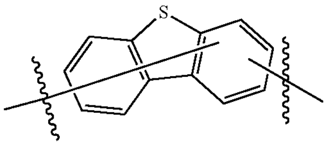

LC8

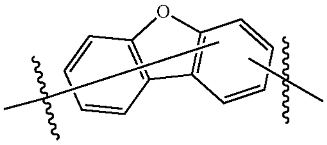

LC9

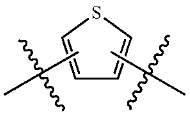

LC10

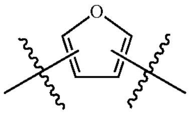

LC11

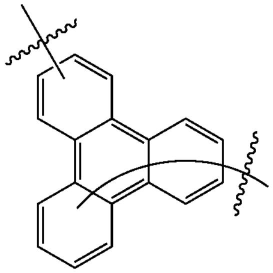

LC12

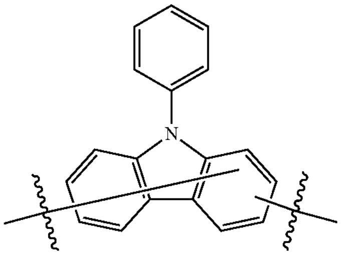

LC13

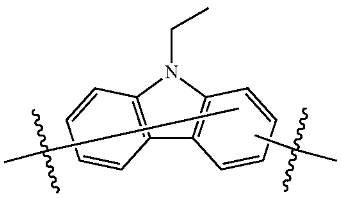

LC14

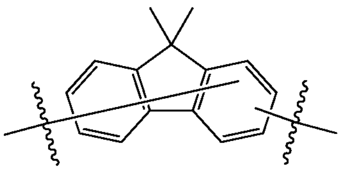

-continued

LC15

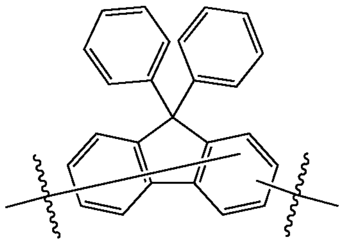

In an exemplary embodiment of the present specification, L107 to L109 are a direct bond.

In an exemplary embodiment of the present specification, Ar9 to Ar11 are the same as or different from each other, and are each independently a substituted or unsubstituted aryl group having 6 to 60 carbon atoms; or a substituted or unsubstituted heteroaryl group having 2 to 60 carbon atoms.

According to another exemplary embodiment, Ar9 to Ar11 are the same as or different from each other, and are each independently an aryl group having 6 to 60 carbon atoms, which is unsubstituted or substituted with an aryl group having 6 to 60 carbon atoms or a heteroaryl group having 2 to 60 carbon atoms; or a heteroaryl group having 2 to 60 carbon atoms, which is unsubstituted or substituted with an aryl group having to 60 carbon atoms or a heteroaryl group having 2 to 60 carbon atoms.

In another exemplary embodiment, Ar9 to Ar11 are the same as or different from each other, and are each independently a substituted or unsubstituted phenyl group; a substituted or unsubstituted biphenyl group; a substituted or unsubstituted naphthyl group; a substituted or unsubstituted phenanthrene group; a substituted or unsubstituted anthracene group; a substituted or unsubstituted triphenylene group; a substituted or unsubstituted dibenzofuran group; a substituted or unsubstituted naphthobenzofuran group; a substituted or unsubstituted dibenzothiophene group; a substituted or unsubstituted carbazole group; a substituted or unsubstituted fluorene group; a substituted or unsubstituted thiophene group; a substituted or unsubstituted furan group; a substituted or unsubstituted benzothiophene group; a substituted or unsubstituted benzofuran group; a substituted or unsubstituted benzocarbazole group; a substituted or unsubstituted benzofluorene group; a substituted or unsubstituted indole carbazole group; a substituted or unsubstituted pyridyl group; a substituted or unsubstituted isoquinolyl group; a substituted or unsubstituted quinolyl group; a substituted or unsubstituted quinazolyl group; a substituted or unsubstituted triazine group; a substituted or unsubstituted benzimidazole group; a substituted or unsubstituted benzoxazole group; a substituted or unsubstituted benzothiazole group; a substituted or unsubstituted dihydroacridine group; a substituted or unsubstituted xanthene group; or a substituted or unsubstituted dibenzosilole group.

In still another exemplary embodiment, Ar9 to Ar11 are the same as or different from each other, and are each independently a phenyl group; a biphenyl group; a naphthyl group unsubstituted or substituted with an aryl group; a phenanthrene group; an anthracene group; a triphenylene group; a dibenzofuran group unsubstituted or substituted with an aryl group; a naphthobenzofuran group; a dibenzothiophene group unsubstituted or substituted with an aryl group; a carbazole group unsubstituted or substituted with alkyl group or an aryl group; a fluorene group unsubstituted or substituted with an alkyl group or an aryl group; a thiophene group unsubstituted or substituted with an aryl group; a furan group unsubstituted or substituted with an aryl group; a benzothiophene group; a benzofuran group; a benzocarbazole group unsubstituted or substituted with an alkyl group or an aryl group; a benzofluorene group unsubstituted or substituted with an alkyl group or an aryl group; an indole carbazole group; a pyridyl group; an isoquinolyl group unsubstituted or substituted with an aryl group; a quinolyl group; a quinazolyl group unsubstituted or substituted with an aryl group; a triazine group unsubstituted or substituted with an aryl group; a benzimidazole group unsubstituted or substituted with an aryl group; a benzoxazole group unsubstituted or substituted with an aryl group; a benzothiazole group unsubstituted or substituted with an aryl group; a dihydroacridine group unsubstituted or substituted with an alkyl group or an aryl group; a xanthene group unsubstituted or substituted with an alkyl group or an aryl group; or a dibenzosilole group unsubstituted or substituted with an alkyl group or an aryl group.

In yet another exemplary embodiment, Ar9 to Ar11 are the same as or different from each other, and are each independently a phenyl group; a biphenyl group; a naphthyl group unsubstituted or substituted with a phenyl group; a phenanthrene group; an anthracene group; a triphenylene group; a dibenzofuran group unsubstituted or substituted with a phenyl group; a naphthobenzofuran group; a dibenzothiophene group unsubstituted or substituted with a phenyl group; a carbazole group unsubstituted or substituted with a methyl group, an ethyl group, or a phenyl group; a fluorene group unsubstituted or substituted with a methyl group or a phenyl group; a thiophene group unsubstituted or substituted with a phenyl group; a furan group unsubstituted or substituted with a phenyl group; a benzothiophene group; a benzofuran group; a benzocarbazole group unsubstituted or substituted with a methyl group or a phenyl group; a benzofluorene group unsubstituted or substituted with a methyl group or a phenyl group; an indole carbazole group; a pyridyl group unsubstituted or substituted with a phenyl group or a naphthyl group; an isoquinolyl group unsubstituted or substituted with a phenyl group; a quinolyl group; a quinazolyl group unsubstituted or substituted with a phenyl group; a triazine group unsubstituted or substituted with a phenyl group; a benzimidazole group unsubstituted or substituted with a phenyl group; a benzoxazole group unsubstituted or substituted with a phenyl group; a benzothiazole group unsubstituted or substituted with a phenyl group; a dihydroacridine group unsubstituted or substituted with a methyl group or a phenyl group; a xanthene group unsubstituted or substituted with a methyl group or a phenyl group; or a dibenzosilole group unsubstituted or substituted with a methyl group or a phenyl group.

In an exemplary embodiment of the present specification, Ar9 to Ar11 are the same as or different from each other, and may be each independently selected from the following structures.

RB1

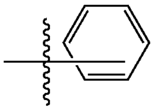

RB2

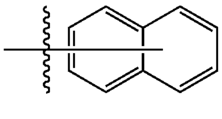

-continued

RB3

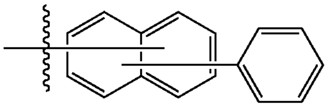

RB4

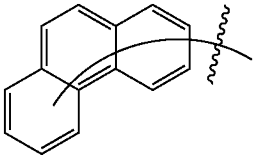

RB5

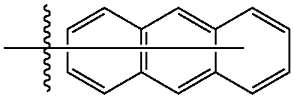

RB6

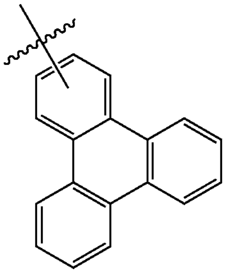

RB7

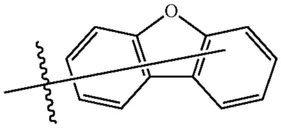

RB8

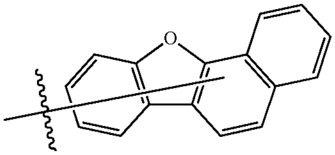

RB9

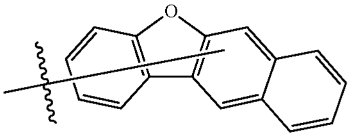

RB10

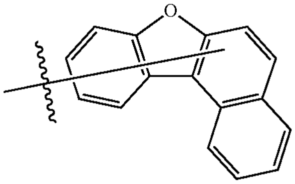

RB11

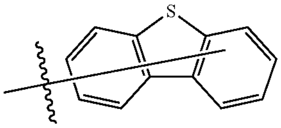

-continued
RB12
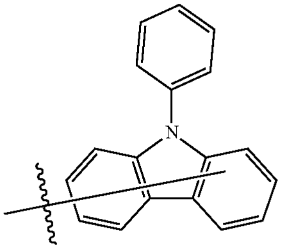
RB13
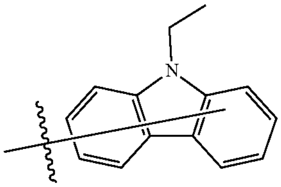
RB14
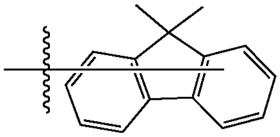
RB15
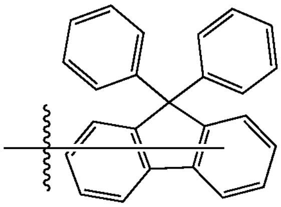
RB16
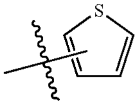
RB17
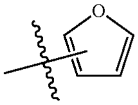
RB18
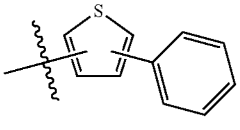
RB19
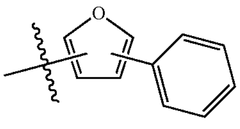
RB20
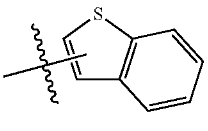
RB21
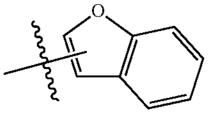
-continued
RB22
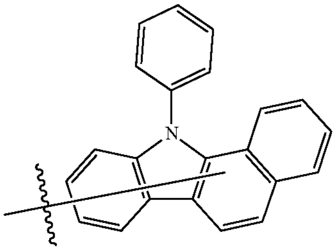
RB23
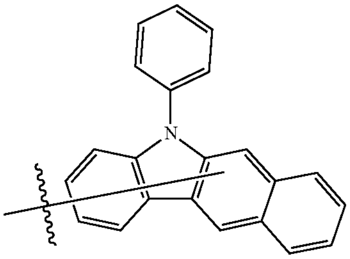
RB24
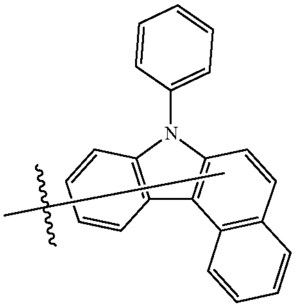
RB25
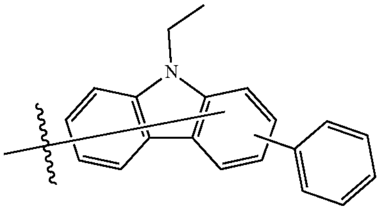
RB26
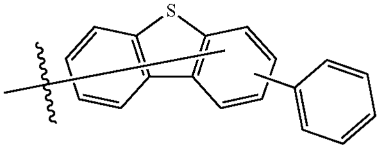
RB27
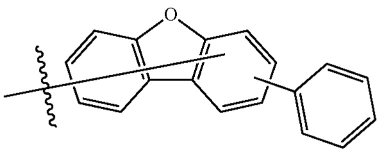
RB28
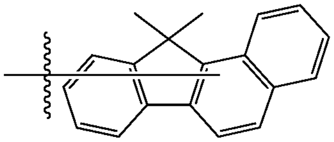

-continued
RB29
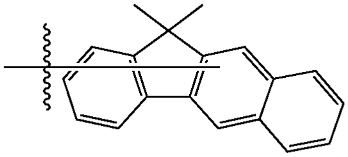
RB30
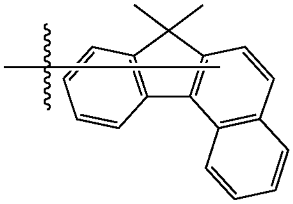
RB31
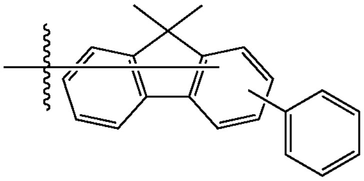
RB32
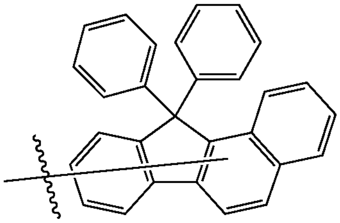
RB33
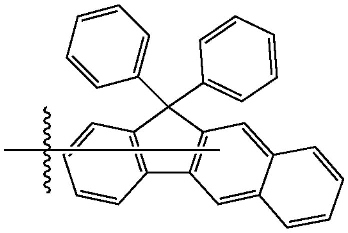
RB34
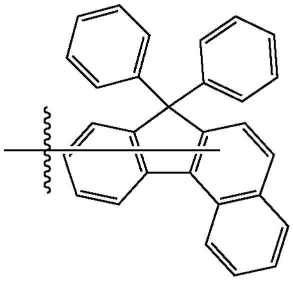
RB35
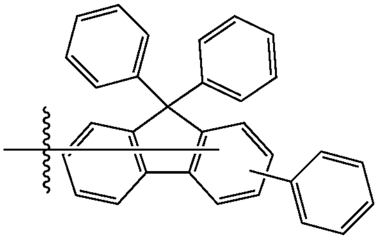
-continued
RB36
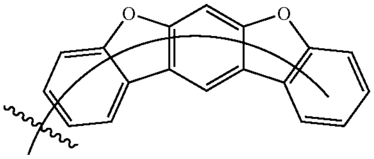
RB37
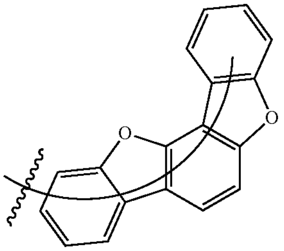
RB38
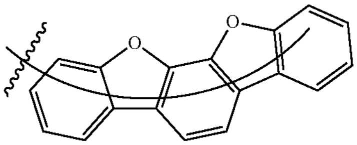
RB39
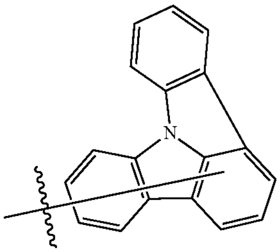
RB40
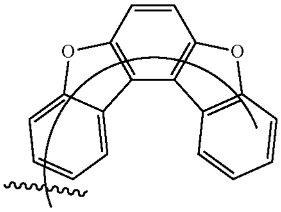
RB41
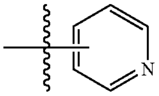
RB42
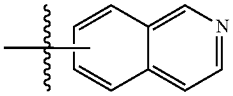
RB43
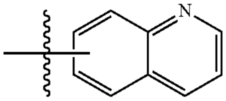
RB44
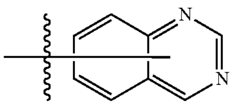

-continued

RB45

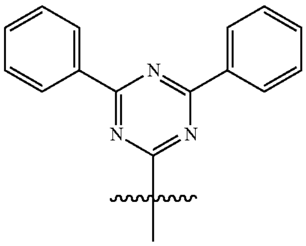

RB46

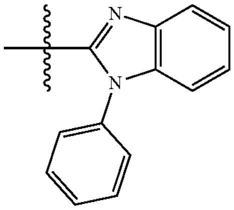

RB47

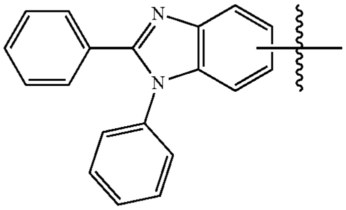

RB48

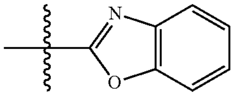

RB49

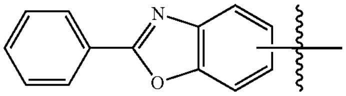

RB50

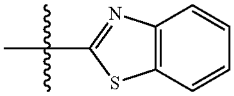

RB51

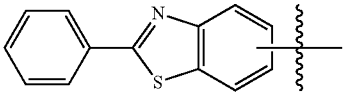

RB52

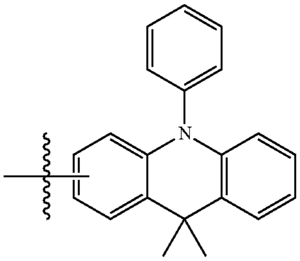

RB53

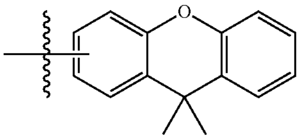

-continued

RB54

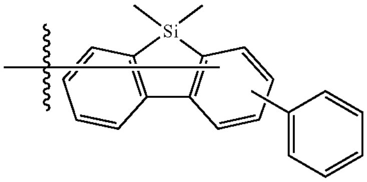

RB55

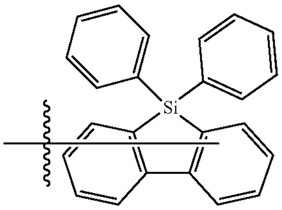

RB56

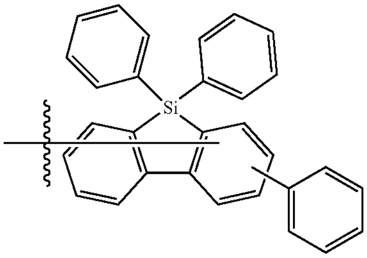

RB57

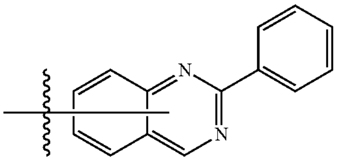

RB58

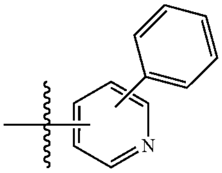

RB59

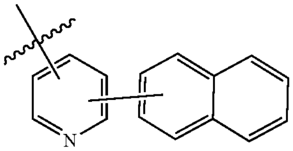

RB60

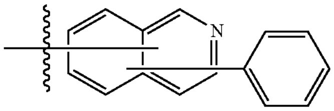

According to an exemplary embodiment of the present specification, the organic material layer comprises a light emitting layer, the light emitting layer comprises the heterocyclic compound represented by Chemical Formula 1 as a dopant of the light emitting layer and includes the compound represented by Chemical Formula 2 or Chemical Formula 3 as a host of the light emitting layer, and the heterocyclic compound represented by Chemical Formula 1 may be doped in an amount of 1 to 30 wt %. According to another exemplary embodiment, the heterocyclic compound represented by Chemical Formula 1 may be doped in an amount of 2 to 20 wt %.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq3; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

In an exemplary embodiment of the present specification, the compound represented by Chemical Formula 1 may be included in an organic solar cell or an organic transistor in addition to the organic light emitting device.

The compound according to the present specification may act even in organic electronic devices including organic phosphorescent devices, organic solar cells, organic photoconductors, organic transistors, and the like, based on the principle similar to those applied to organic light emitting devices.

Hereinafter, the present specification will be described in detail with reference to Examples in order to specifically explain the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

SYNTHESIS EXAMPLES

Synthesis Example 1

Synthesis of Intermediate 1-1

Intermediate 1-1 was synthesized according to the following reaction formula.

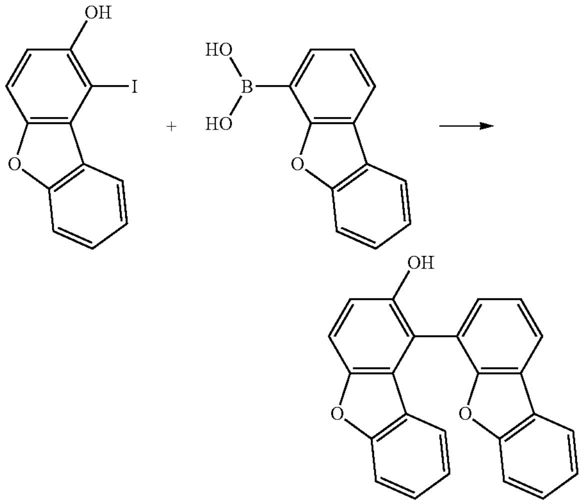

<Intermediate 1-1>

1-iododibenzo[b,d]furan-2-ol (80.0 g, 0.258 mol) and dibenzo[b,d]furan-4-ylboronic acid (60.2 g, 0.284 mol) were put into a 1 L flask, and tetrahydrofuran (500 mL) and potassium carbonate (107.0 g, 0.774 mol) dissolved in water (340 mL) were put thereinto. The temperature of the reactor was increased until the mixture was refluxed, and simultaneously, a tetrakis triphenylphosphine palladium catalyst (1.34 g, 1.16 mmol) was diluted with a small amount of tetrahydrofuran, and then the resulting product was introduced thereinto. After the reflux, it was confirmed that the reaction was terminated, and then the reactor was cooled again. After the product was extracted by using water and an ethyl acetate solvent to remove the aqueous layer, the remaining product was treated with anhydrous magnesium sulfate, and then filtered and concentrated to obtain a target product. <Intermediate 1-1> (65 g, yield 72%) was obtained through recrystallization purification with ethyl acetate and hexane.

Mass [M+1]=351

Synthesis Example 2

Synthesis of Intermediate 1-2

Intermediate 1-2 was synthesized according to the following reaction formula.

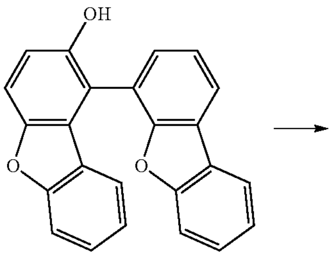

<Intermediate 1-1>

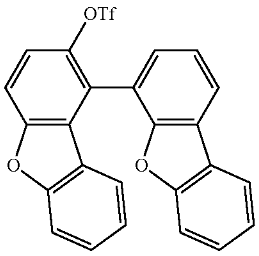

<Intermediate 1-2>

<Intermediate 1-1> (65.0 g, 0.186 mol) was put into a 1 L flask under a nitrogen atmosphere, and was diluted with dichloromethane (600 mL). The flask was transferred to an ice bath, then pyridine (22.0 g, 0.214 mol) was added thereto, and subsequently, trifluoromethanesulfonic anhydride (68.1 g, 0.1867 mmol) was added dropwise thereto. After the dropwise addition, the ice bath was removed, and the mixture was warmed to room temperature, and stirred for 2 hours. After the completion of the reaction, extraction with ethyl acetate and water was performed, and the organic layer was treated with anhydrous magnesium sulfate, and then filtered and concentrated to obtain <Intermediate 1-2> (58.0 g, yield 65%) by using a column chromatography method.

The reaction was confirmed with TLC and HPLC.

Synthesis Example 3

Synthesis of Intermediate 1-3

Intermediate 1-3 was synthesized according to the following reaction formula.

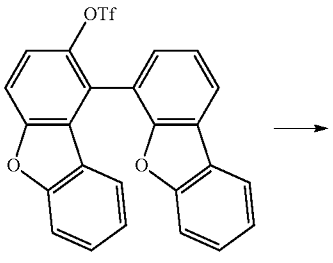

<Intermediate 1-2>

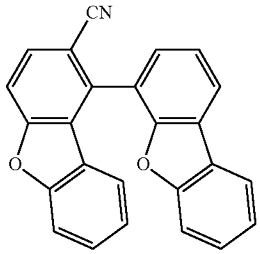

<Intermediate 1-3>

<Intermediate 1-2> (55.0 g, 0.114 mol), potassium cyanide (14.8 g, 0.228 mol), and tetrakistriphenylphosphine palladium (0.59 g, 0.51 mmol) were put into a 0.5 L flask, and N,N-dimethylformamide (300 mL) was introduced thereinto. The internal temperature was increased to 130° C., the flask was stirred for 18 hours, and then the reaction was terminated. After the reaction solvent was distilled and removed under reduced pressure, extraction with ethyl acetate and water was performed, and the organic layer was treated with anhydrous magnesium sulfate, and then filtered and concentrated to obtain <Intermediate 1-3> (29.0 g, yield 71%) by using a column chromatography method.

Mass [M+1]=360

Synthesis Example 4

Synthesis of Intermediate 1-4

Intermediate 1-4 was synthesized according to the following reaction formula.

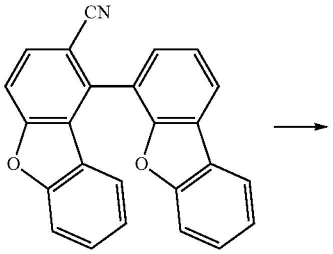

<Intermediate 1-3>

-continued

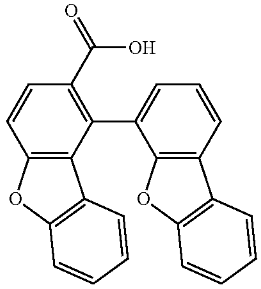

<Intermediate 1-4>

<Intermediate 1-3> (29.0 g, 0.081 mol) and potassium hydroxide (9.1 g, 0.161 mol) were put into a 0.5 L flask, and ethanol (300 mL) and water (100 mL) were introduced thereinto. The mixture was reacted by refluxing and stirring the flask for about 30 hours, the resulting product was cooled to room temperature, and then acidified by using diluted hydrochloric acid, the precipitated solid was filtered and washed with n-hexane, and then dried under nitrogen to obtain <Intermediate 1-4> (25.0 g, yield 82%).

The reaction was confirmed with TLC and HPLC.

Synthesis Example 5

Synthesis of Intermediate 1-5

Intermediate 1-5 was synthesized according to the following reaction formula.

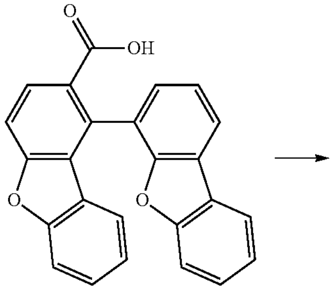

<Intermediate 1-4>

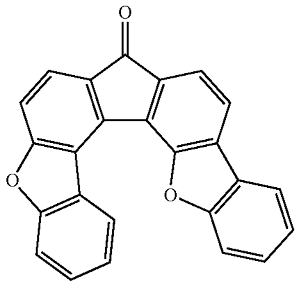

<Intermediate 1-5>

<Intermediate 1-4> (25.0 g, 0.066 mol) and methanesulfonic acid (200 mL) were put into a 0.5 L flask, and the resulting mixture was warmed to 120° C. and stirred for 4 hours. After cooling, the mixture was solidified by adding dropwise the reaction solution to an excessive amount of water, and the obtained solid was purified again with toluene to obtain <Intermediate 1-5> (15.0 g, yield 63%).

Mass [M+1]=361

Synthesis Example 6

Synthesis of Intermediate 1-6

Intermediate 1-6 was synthesized according to the following reaction formula.

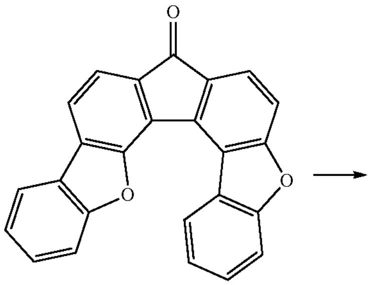

<Intermediate 1-5>

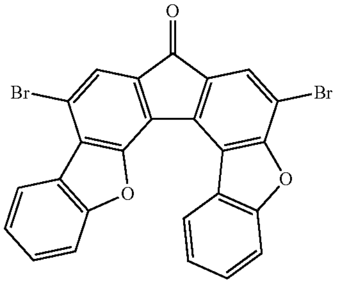

<Intermediate 1-6>

After <Intermediate 1-5> (10.0 g, 27.7 mmol) was added to 300 ml of dichloromethane in a 0.5 L flask and the resulting mixture was stirred, bromine (13.3 g, 83.2 mmol) diluted in 50 mL of dichloromethane was slowly added dropwise thereto, and then the resulting mixture was stirred at room temperature for 60 hours. Thereafter, the produced solid was filtered, and then washed with dichloromethane and hexane. The solid was recrystallized with toluene and N-methylpyrrolidone to obtain <Intermediate 1-6> (3.5 g, yield 24%).

Synthesis Example 7

Synthesis of Intermediate 1-7

Intermediate 1-7 was synthesized according to the following reaction formula.

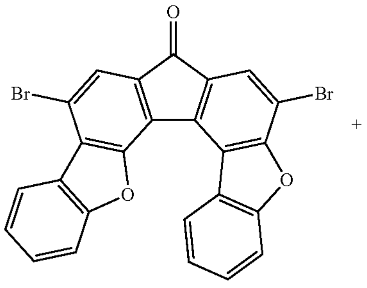

<Intermediate 1-6>

-continued

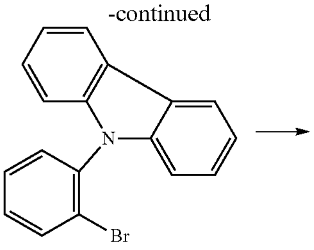

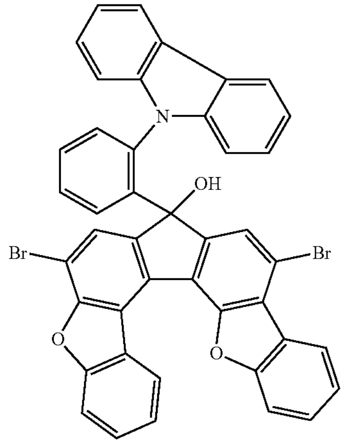

<Intermediate 1-7>

9-(2-bromophenyl)-9H-carbazole (2.7 g, 8.38 mmol) and 100 mL of tetrahydrofuran were put into a 0.25 L flask under a nitrogen atmosphere, and the resulting mixture was cooled to −78° C. A 2.5 M tetrahydrofuran solution (4.36 mL, 10.9 mmol) of n-butyllithium was added dropwise to the cooled reaction solution, and then the resulting mixture was stirred at the same temperature for 1 hour. Thereafter, <Intermediate 1-6> (3.47 g, 6.70 mmol) was introduced thereinto at the same temperature, and then the resulting mixture was slowly warmed to room temperature and stirred for 18 hours. After the completion of the reaction, the reaction was terminated by adding water thereto, and then extraction with ethyl acetate and water was performed. The organic layer was treated with anhydrous magnesium sulfate, and then filtered and concentrated under reduced pressure. From the solid obtained by the reaction, <Intermediate 1-7> (3.2 g, yield 63%) was obtained by using a silica gel column chromatography method with ethyl acetate and n-hexane.

Synthesis Example 8

Synthesis of Intermediate 1-8

Intermediate 1-8 was synthesized according to the following reaction formula.

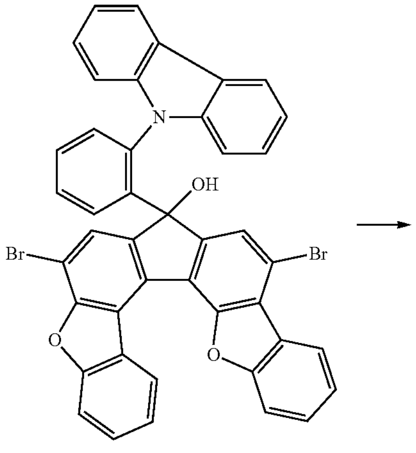

<Intermediate 1-7>

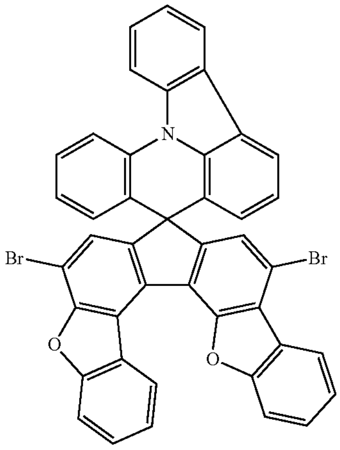

<Intermediate 1-8>

<Intermediate 1-7> (3.2 g, 4.20 mmol), acetic acid (100 mL), and two drops of sulfuric acid were put into a 0.25 L flask, and the resulting mixture was heated and stirred at a temperature of 80° C. for 2 hours. After the completion of the reaction, the produced product was filtered and then washed with water and ethanol, and then was recrystallized with ethyl acetate and hexane to obtain <Intermediate 1-8> (2.9 g, yield 93%).

Synthesis Example 9

Synthesis of Intermediate 2-1

Compound 1 was synthesized according to the following reaction formula.

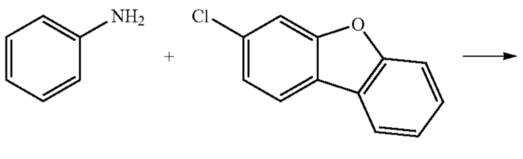

-continued

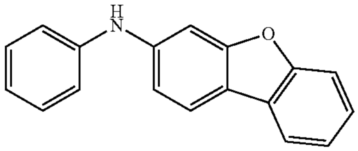

<Intermediate 2-1>

3-chlorobenzo[b,d]furan (25.0 g, 0.123 mol), aniline (12.6 g, 0.135 mol), sodium tert-butoxide (35.6 g, 0.370 mol), and bis(tri-tert-butylphosphine)palladium (0) (1.89 g, 3.70 mmol) were put into 350 mL of toluene in a 1 L flask under a nitrogen atmosphere, and the resulting mixture was refluxed and stirred. When the reaction was terminated, the mixture was cooled to room temperature, and then extraction with toluene and water was performed, and the aqueous layer was removed. The remaining product was treated with anhydrous magnesium sulfate, and then filtered and concentrated under reduced pressure. The product was separated and purified with a column chromatography method, and then recrystallized with toluene and n-hexane to obtain <Intermediate 2-1>(22.0 g, yield 69%).

Mass [M+1]=260

Synthesis Example 10

Synthesis of Compound 1

Compound 1 was synthesized according to the following reaction formula.

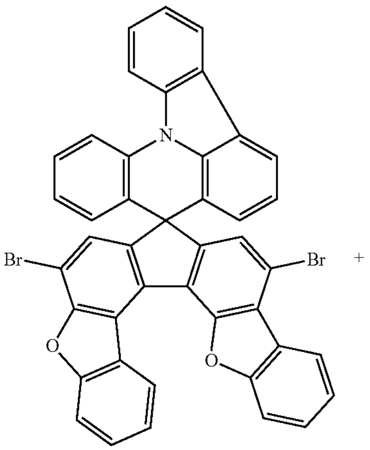

<Intermediate 1-8>

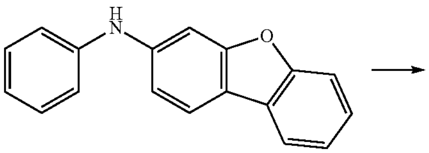

<Intermediate 2-1>

-continued

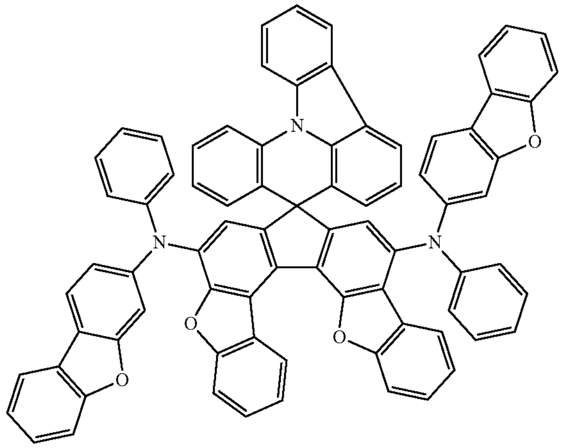

<Compound 1>

<Intermediate 1-8> (2.9 g, 3.90 mmol), <Intermediate 2-1> (2.23 g, 8.58 mmol), sodium tert-butoxide (1.87 g, 19.5 mmol), and bis(tri-tert-butylphosphine)palladium (0) (0.20 g, 0.39 mmol) were put into 50 mL of toluene in a 0.1 L flask under a nitrogen atmosphere, and the resulting mixture was refluxed and stirred. When the reaction was terminated, the mixture was cooled to room temperature, and then extraction with toluene and water was performed, and the aqueous layer was removed. The remaining product was treated with anhydrous magnesium sulfate, and then filtered and concentrated under reduced pressure. The product was separated and purified with a column chromatography method, and then recrystallized with toluene and n-hexane to obtain <Compound 1> (2.1 g, yield 49%).

Mass [M+1]=1100

Synthesis Example 11

Synthesis of Compound 5

Compound 5 was synthesized according to the following reaction formula.

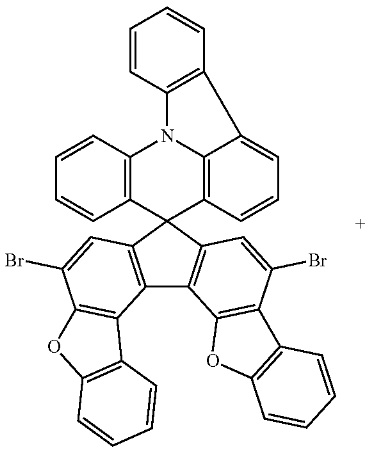

<Intermediate 1-8>

-continued

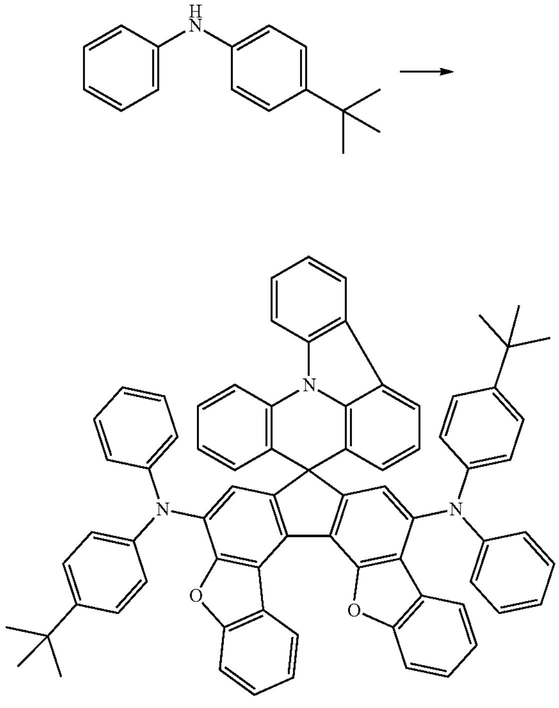

<Compound 5>

Compound 5 was synthesized in the same manner as in Synthesis Example 10 by using <Intermediate 1-8> and 4-(tertbutyl)-N-phenylaniline. The NMR data of Compound 5 are illustrated in the following FIG. 3.

Mass [M+1]=1032

Synthesis Example 12

Synthesis of Intermediate 2-2

<Intermediate 2-2> was synthesized according to the following reaction formula.

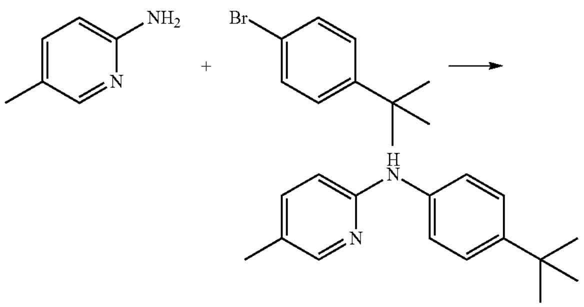

<Intermediate 2-2>

An experiment was performed in the same manner as in Synthesis Example 9 by using 5-methylpyridine-2-amine and 1-bromo-4-(t-butyl)benzene, thereby synthesizing <Intermediate 2-2>.

Mass [M+1]=241

Synthesis Example 13

Synthesis of Compound 20

Compound 20 was synthesized according to the following reaction formula.

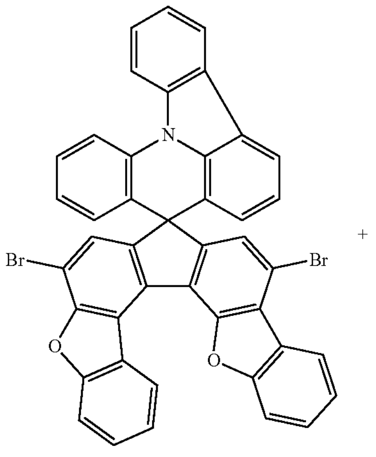

<Intermediate 1-8>

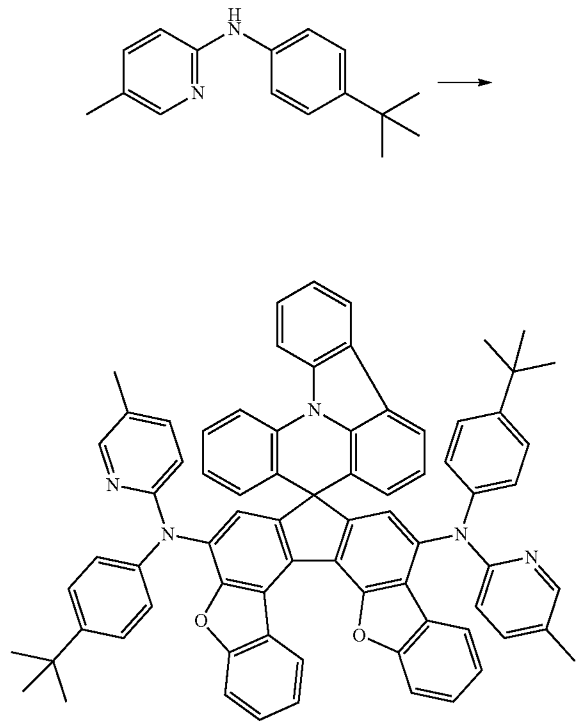

<Compound 20>

An experiment was performed in the same manner as in Synthesis Example 10 by using <Intermediate 1-8> and <Intermediate 2-2>, thereby synthesizing Compound 20.

Mass [M+1]=1100

Synthesis Example 14

Synthesis of Intermediate 2-3

<Intermediate 2-3> was synthesized according to the following reaction formula.

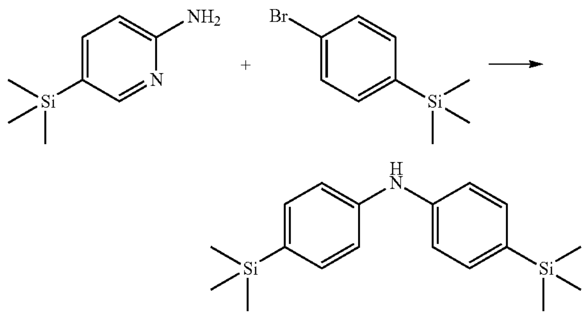

<Intermediate 2-3>

An experiment was performed in the same manner as in Synthesis Example 9 by using 4-(trimethylsilyl)aniline and (4-bromophenyl)trimethylsilane, thereby synthesizing <Intermediate 2-3>.

Mass [M+1]=314

Synthesis Example 15

Synthesis of Compound 25

Compound 25 was synthesized according to the following reaction formula.

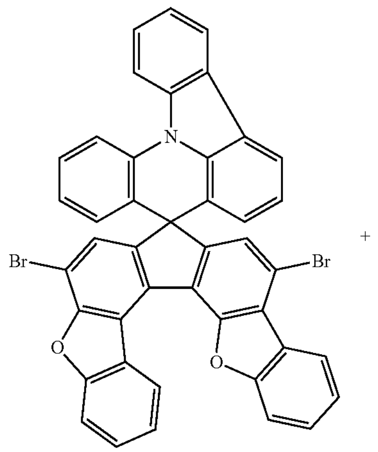

<Intermediate 1-8>

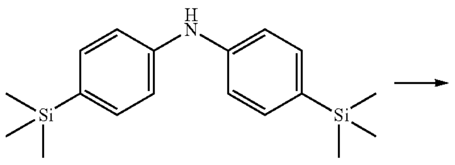

-continued

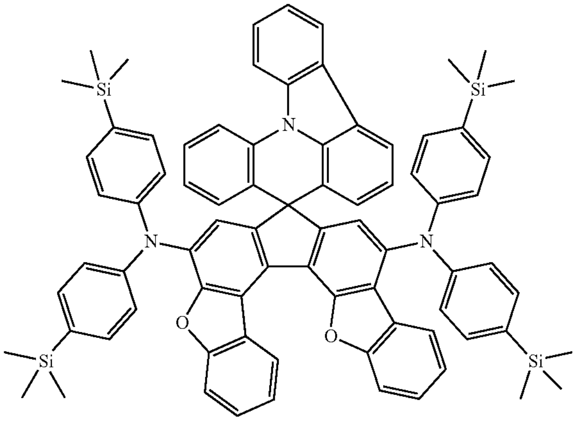

<Compound 25>

An experiment was performed in the same manner as in Synthesis Example 10 by using <Intermediate 1-8>and <Intermediate 2-3>, thereby synthesizing Compound 25.

Mass [M+1]=1208

Synthesis Example 16

Synthesis of Compound 26

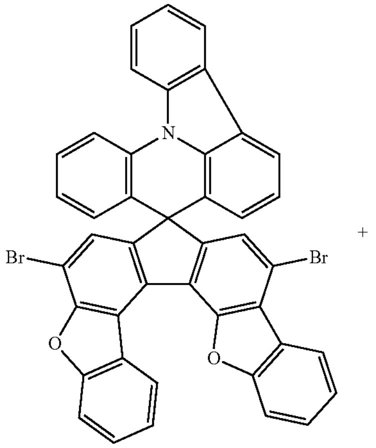

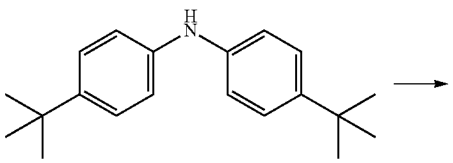

-continued

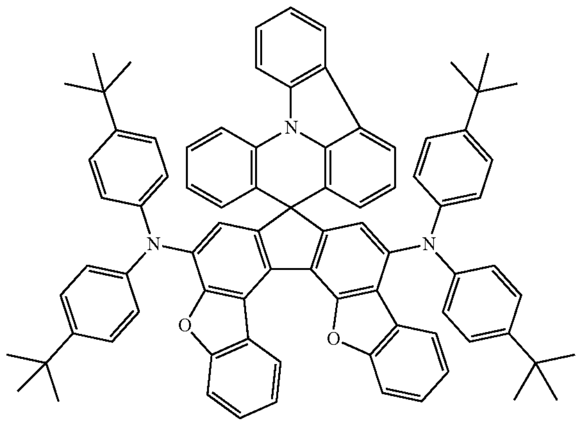

<Compound 26>

An experiment was performed in the same manner as in Synthesis Example 10 by using <Intermediate 1-8> and bis(4-(tert-butyl)phenyl)amine, thereby synthesizing Compound 26.

Mass [M+1]=1145

Synthesis Example 17

Synthesis of Intermediate 2-4

<Intermediate 2-4> was synthesized according to the following reaction formula.

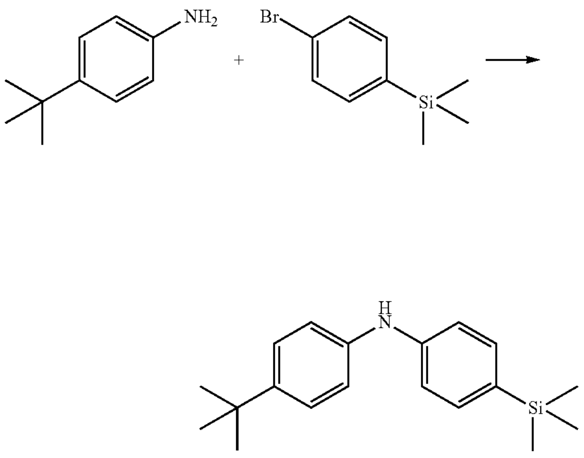

<Intermediate 2-4>

An experiment was performed in the same manner as in Synthesis Example 9 by using 4-(t-butyl)aniline and (4-bromophenyl)trimethylsilane, thereby synthesizing <Intermediate 2-4>.

Mass [M+1]=298

Synthesis Example 18

Synthesis of Compound 42

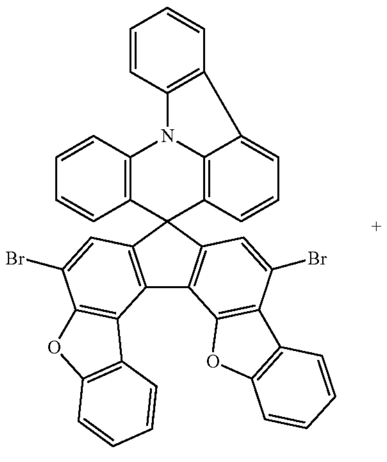

<Intermediate 1-8>

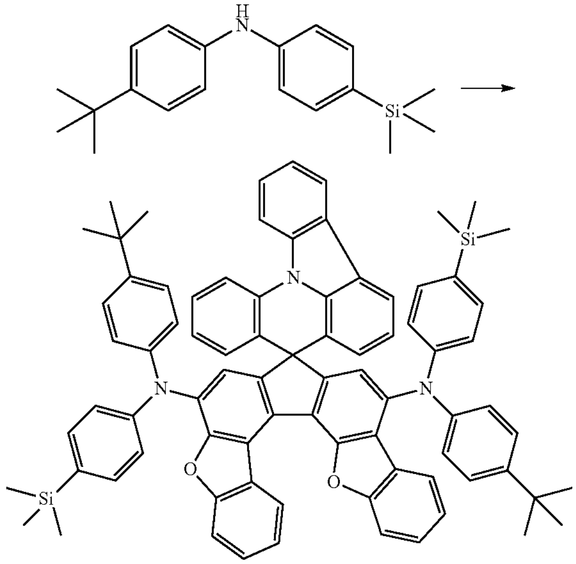

<Compound 42>

An experiment was performed in the same manner as in Synthesis Example 10 by using <Intermediate 1-d> and <Intermediate 2-4>, thereby synthesizing Compound 42.

Mass [M+1]=1100

Synthesis Example 19

Synthesis of Intermediate 3-1

Intermediate 3-1 was synthesized according to the following reaction formula.

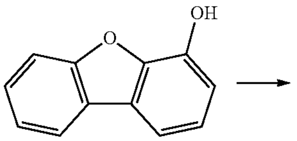

-continued

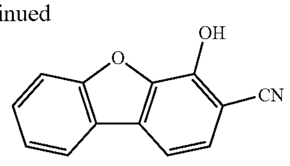

<Intermediate 3-1>

Dibenzo[b,d]furan-4-ol (50.0 g, 0.271 mol), zinc cyanide (51.0 g, 0.434 mol), and tetrakistriphenylphosphine palladium (1.57 g, 1.36 mmol) were put into a 1 L flask, and acetonitrile (500 mL) was introduced thereinto. The mixture was refluxed, stirred, and reacted for 18 hours, and then the reaction was terminated. After the reaction solvent was distilled and removed under reduced pressure, the organic layer obtained by performing extraction with ethyl acetate and water was treated with anhydrous magnesium sulfate, and then filtered and concentrated to obtain <Intermediate 3-1> (29.0 g, yield 51%) by using a column chromatography method.

Mass [M+1]=210

Synthesis Example 20

Synthesis of Intermediate 3-2

Intermediate 3-2 was synthesized according to the following reaction formula.

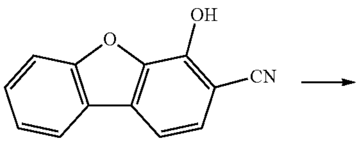

<Intermediate 3-1>

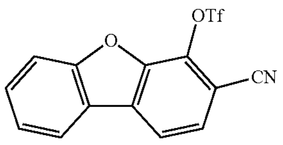

<Intermediate 3-2>

<Intermediate 3-1> (29.0 g, 0.139 mol) was put into a 1 L flask under a nitrogen atmosphere, and was diluted with dichloromethane (600 mL). The flask was transferred to an ice bath, pyridine (16.4 g, 0.208 mol) was added thereto, and subsequently, trifluoromethanesulfonic anhydride (50.9 g, 0.180 mmol) was added dropwise thereto. After the dropwise addition, the ice bath was removed, the mixture was warmed to room temperature, and stirred for 2 hours. After the completion of the reaction, extraction with ethyl acetate and water was performed and the organic layer was treated with anhydrous magnesium sulfate, and then filtered and concentrated to obtain <Intermediate 3-2> (33.0 g, yield 70%) by using a column chromatography method.

The reaction was confirmed with TLC and HPLC.

Synthesis Example 21

Synthesis of Intermediate 3-3

Intermediate 3-3 was synthesized according to the following reaction formula.

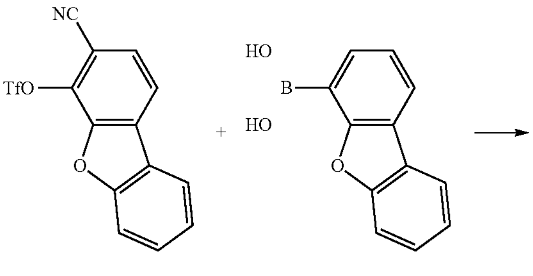

<Intermediate 3-2>

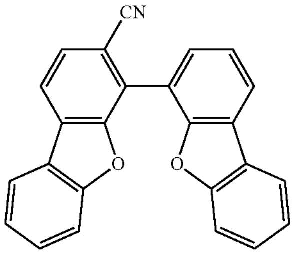

<Intermediate 3-3>

An experiment was performed in the same manner as in Synthesis Example 1 by using <Intermediate 3-2>, thereby synthesizing <Intermediate 3-3>.

Mass [M+1]=360

Synthesis Example 22

Synthesis of Intermediate 3-4

Intermediate 3-4 was synthesized according to the following reaction formula.

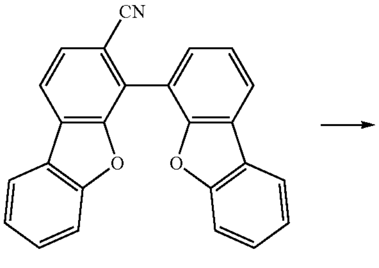

<Intermediate 3-3>

-continued

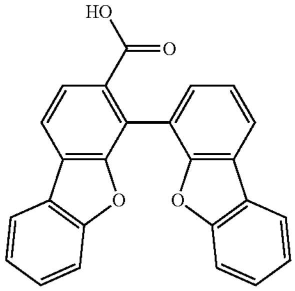

<Intermediate 3-4>

An experiment was performed in the same manner as in Synthesis Example 4 by using <Intermediate 3-3>, thereby synthesizing <Intermediate 3-4>.

The reaction was confirmed with TLC and HPLC.

Synthesis Example 23

Synthesis of Intermediate 3-5

Intermediate 3-5 was synthesized according to the following reaction formula.

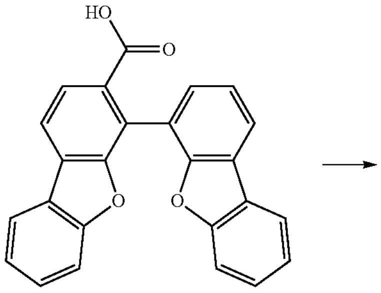

<Intermediate 3-4>

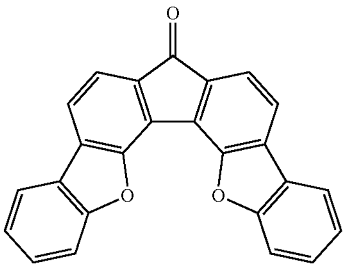

<Intermediate 3-5>

An experiment was performed in the same manner as in Synthesis Example 5 by using <Intermediate 3-4>, thereby synthesizing <Intermediate 3-5>.

Mass [M+1]=361

Synthesis Example 24

Synthesis of Intermediate 3-6

Intermediate 3-6 was synthesized according to the following reaction formula.

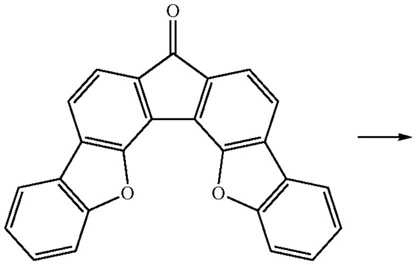

<Intermediate 3-5>

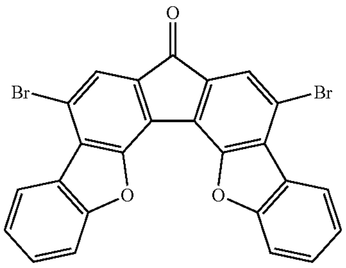

<Intermediate 3-6>

An experiment was performed in the same manner as in Synthesis Example 6 by using <Intermediate 3-5>, thereby synthesizing <Intermediate 3-6>.

Mass [M+1]=517

Synthesis Example 25

Synthesis of Intermediate 3-7

Intermediate 3-7 was synthesized according to the following reaction formula.

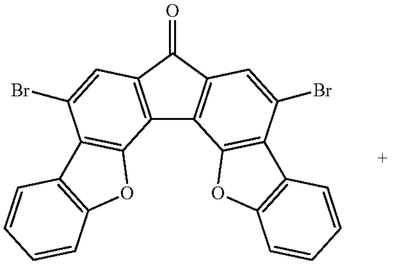

<Intermediate 3-6>

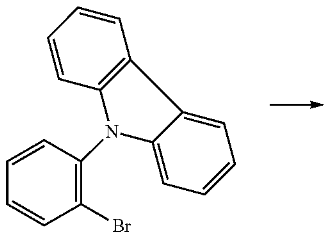

-continued

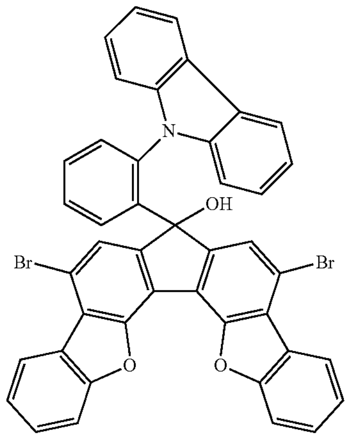

<Intermediate 3-7>

An experiment was performed in the same manner as in Synthesis Example 7 by using <Intermediate 3-6>, thereby synthesizing <Intermediate 3-7>.

Mass [M+1]=760

Synthesis Example 26

Synthesis of Intermediate 3-8

Intermediate 3-8 was synthesized according to the following reaction formula.

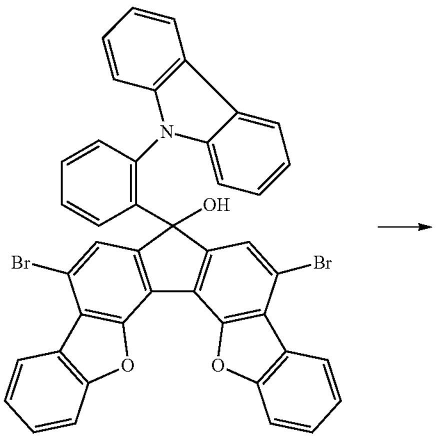

<Intermediate 3-7>

-continued

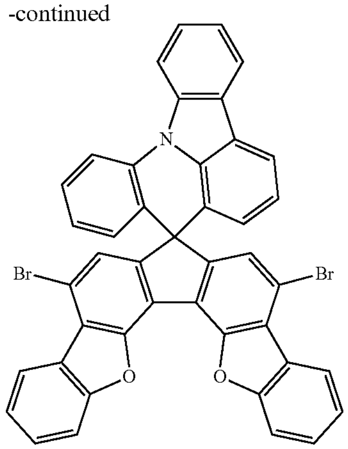

<Intermediate 3-8>

An experiment was performed in the same manner as in Synthesis Example 8 by using <Intermediate 3-6>, thereby synthesizing <Intermediate 3-8>.

Mass [M+1]=742

Synthesis Example 27

Synthesis of Intermediate 2-5

<Intermediate 2-5> was synthesized according to the following reaction formula.

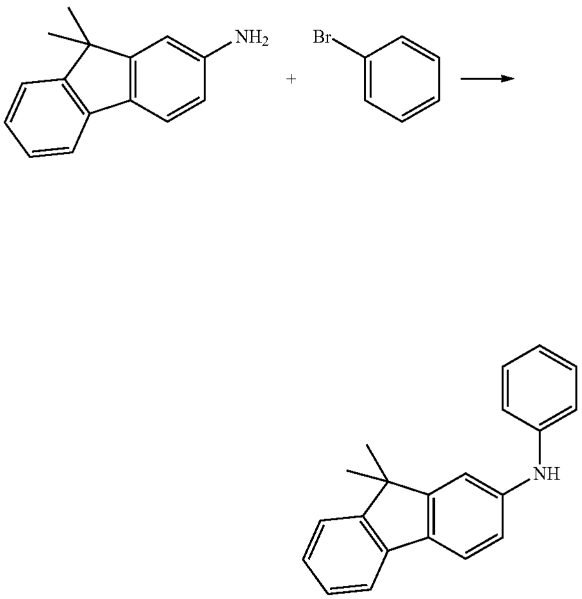

<Intermediate 2-5>

An experiment was performed in the same manner as in Synthesis Example 9 by using 9,9-dimethyl-9H-fluorene-2-amine and bromobenzene, thereby synthesizing <Intermediate 2-5>.

Mass [M+1]=286

Synthesis Example 28

Synthesis of Compound 11

Compound 11 was synthesized according to the following reaction formula.

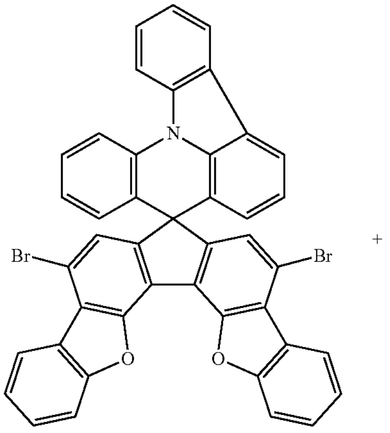

<Intermediate 3-8>

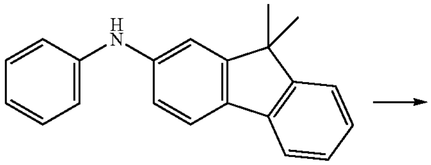

<Intermediate 2-5>

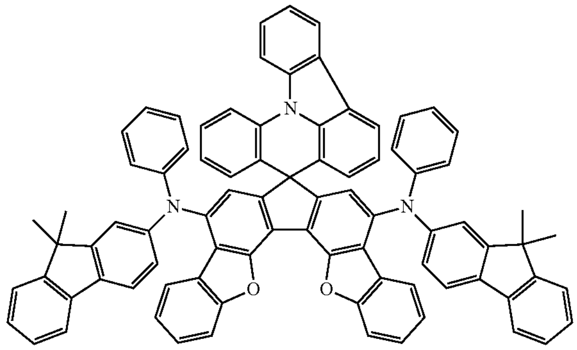

<Compound 11>

An experiment was performed in the same manner as in Synthesis Example 10 by using <Intermediate 3-8> and <Intermediate 2-5>, thereby synthesizing <Compound 11>.

It was confirmed that Mass [M+1]=1152

Synthesis Example 29

Synthesis of Intermediate 4-1

Intermediate 4-1 was synthesized according to the following reaction formula.

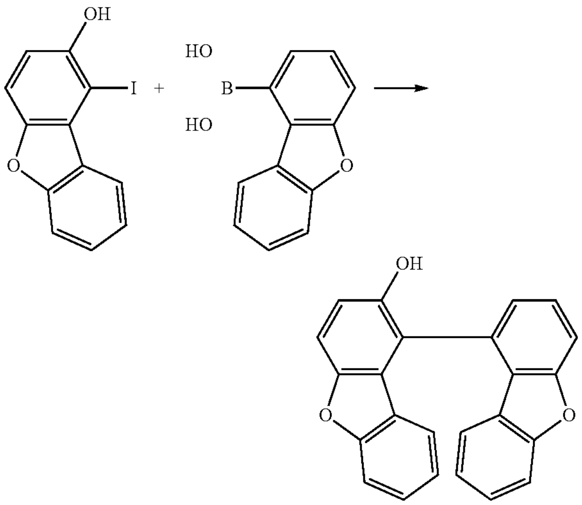

<Intermediate 4-1>

An experiment was performed in the same manner as in Synthesis Example 1 by using dibenzo[b,d]furan-1-ylboronic acid, thereby synthesizing <Intermediate 4-1>.

It was confirmed that Mass [M+1]=351

Synthesis Example 30

Synthesis of Intermediate 4-2

Intermediate 4-2 was synthesized according to the following reaction formula.

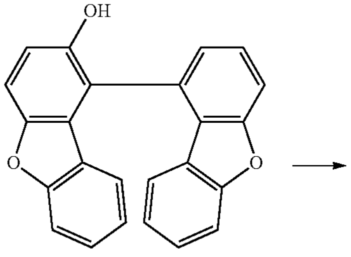

<Intermediate 4-1>

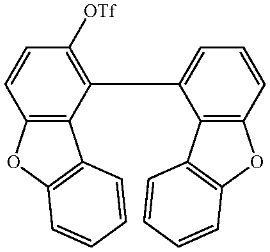

<Intermediate 4-2>

An experiment was performed in the same manner as in Synthesis Example 2 by using <Intermediate 4-2>, thereby synthesizing <Intermediate 4-2>.

The reaction was confirmed with TLC and HPLC.

Synthesis Example 31

Synthesis of Intermediate 4-3

Intermediate 4-3 was synthesized according to the following reaction formula.

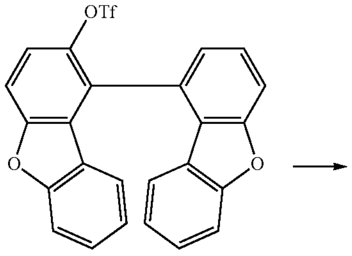

<Intermediate 4-2>

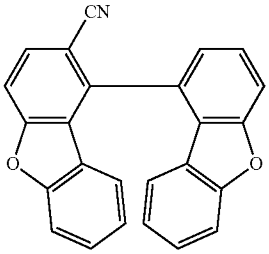

<Intermediate 4-3>

An experiment was performed in the same manner as in Synthesis Example 3 by using <Intermediate 4-2>, thereby synthesizing <Intermediate 4-3>.

Mass [M+1]=360

Synthesis Example 32

Synthesis of Intermediate 4-4

Intermediate 4-4 was synthesized according to the following reaction formula.

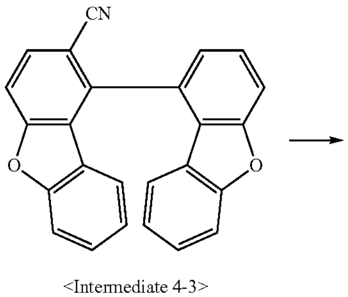

<Intermediate 4-3>

-continued

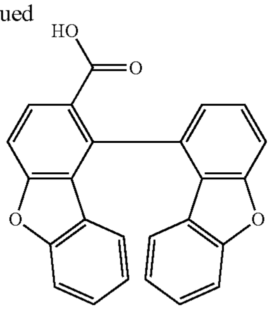

<Intermediate 4-4>

An experiment was performed in the same manner as in Synthesis Example 4 by using <Intermediate 4-3>, thereby synthesizing <Intermediate 4-4>.

The reaction was confirmed with TLC and HPLC.

Synthesis Example 33

Synthesis of Intermediate 4-5

Intermediate 4-5 was synthesized according to the following reaction formula.

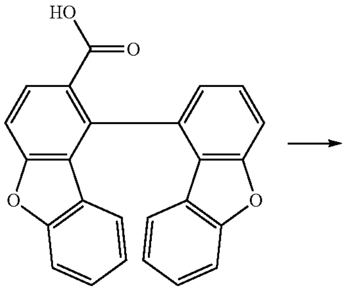

<Intermediate 4-4>

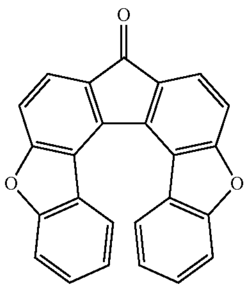

<Intermediate 4-5>

An experiment was performed in the same manner as in Synthesis Example 5 by using <Intermediate 4-4>, thereby synthesizing <Intermediate 4-5>.

Mass [M+1]=361

Synthesis Example 34

Synthesis of Intermediate 4-6

Intermediate 4-6 was synthesized according to the following reaction formula.

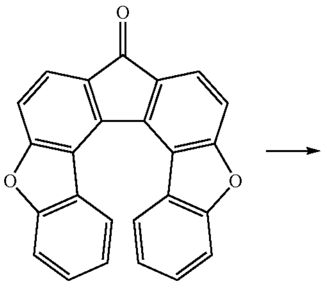

<Intermediate 4-5>

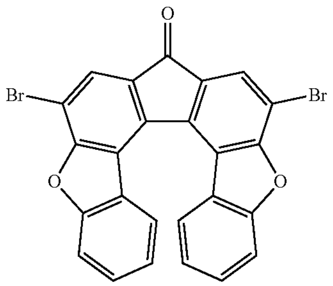

<Intermediate 4-6>

An experiment was performed in the same manner as in Synthesis Example 6 by using <Intermediate 4-5>, thereby synthesizing <Intermediate 4-6>.

Mass [M+1]=517

Synthesis Example 35

Synthesis of Intermediate 4-7

Intermediate 4-7 was synthesized according to the following reaction formula.

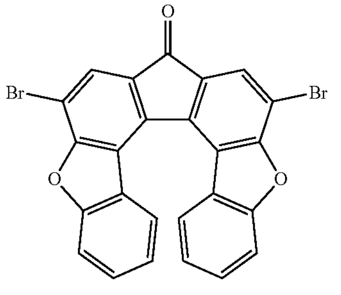

<Intermediate 4-6>

+

-continued

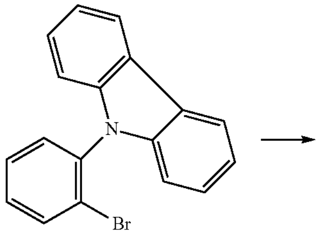

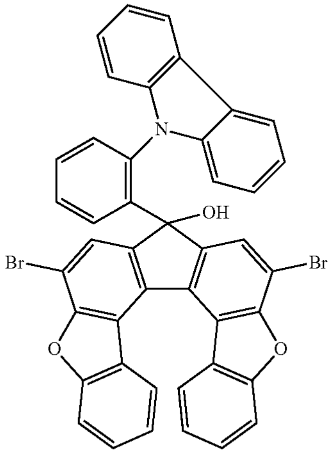

<Intermediate 4-7>

An experiment was performed in the same manner as in Synthesis Example 7 by using <Intermediate 4-6>, thereby synthesizing <Intermediate 4-7>.

Mass [M+1]=762

Synthesis Example 36

Synthesis of Intermediate 4-8

Intermediate 4-8 was synthesized according to the following reaction formula.

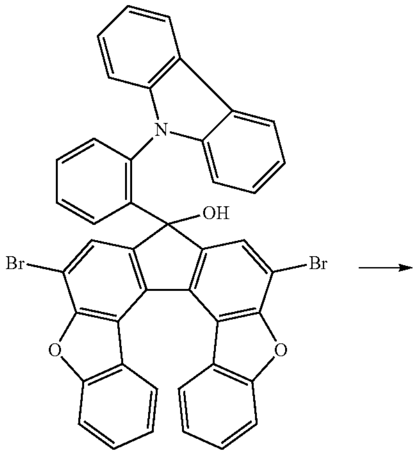

<Intermediate 4-7>

-continued

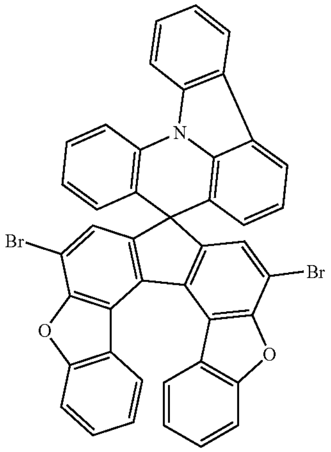

<Intermediate 4-8>

An experiment was performed in the same manner as in Synthesis Example 8 by using <Intermediate 4-7>, thereby synthesizing <Intermediate 4-8>.

Mass [M+1]=743

Synthesis Example 37

Synthesis of Intermediate 2-6

<Intermediate 2-6> was synthesized according to the following reaction formula.

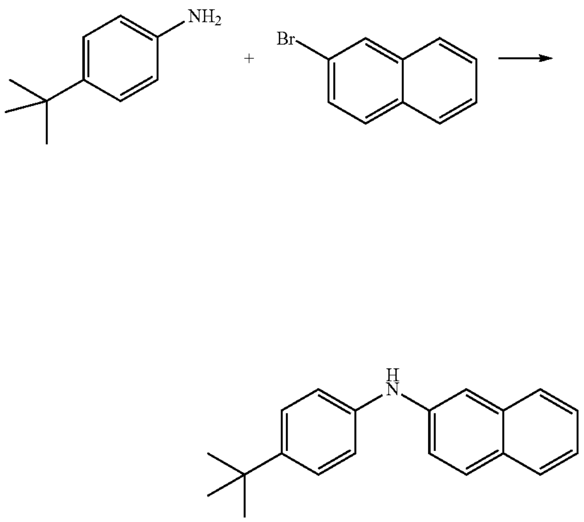

<Intermediate 2-6>

An experiment was performed in the same manner as in Synthesis Example 9 by using 4-(t-butyl)aniline and 2-bromonaphthalene, thereby synthesizing <Intermediate 2-6>.

Mass [M+1]=276

Synthesis Example 38

Synthesis of Compound 24

Compound 24 was synthesized according to the following reaction formula.

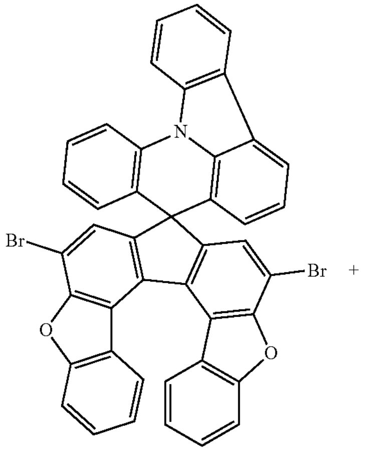

<Intermediate 4-8>

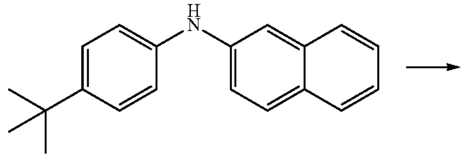

<Intermediate 2-6>

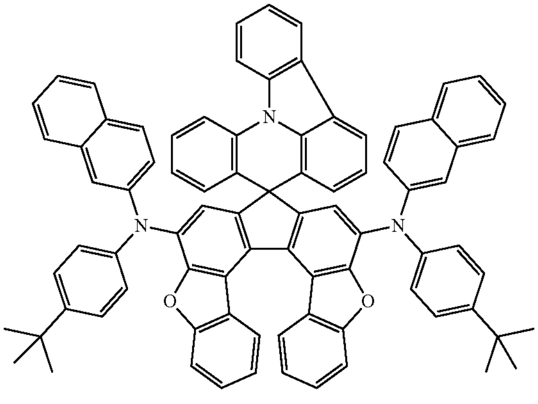

<Compound 24>

An experiment was performed in the same manner as in Synthesis Example 10 by using <Intermediate 4-8> and <Intermediate 2-6>, thereby synthesizing <Compound 24>.

Mass [M+1]=1132

Synthesis Example 39

Synthesis of Intermediate 5-1

Intermediate 5-1 was synthesized according to the following reaction formula.

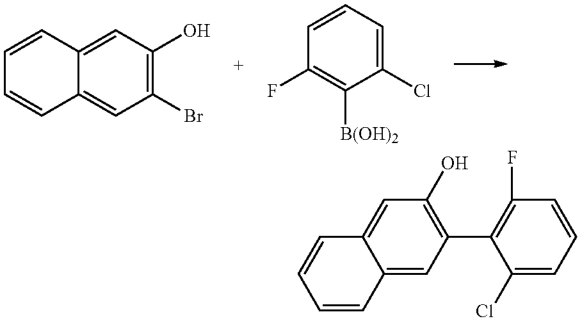

<Intermediate 5-1>

An experiment was performed in the same manner as in Synthesis Example 1 by using 3-bromonaphthalene-2-ol and (2-chloro-6-fluorophenyl)boronic acid, thereby synthesizing <Intermediate 5-1>.

Mass [M+1]=273

Synthesis Example 40

Synthesis of Intermediate 5-2

Intermediate 5-2 was synthesized according to the following reaction formula.

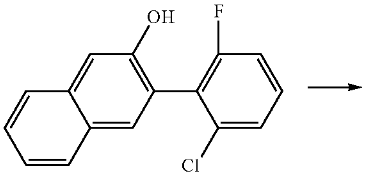

<Intermediate 5-1>

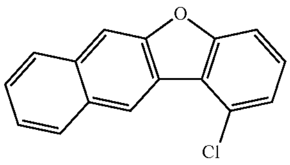

<Intermediate 5-2>

After <Intermediate 5-1> (32.0 g, 0.153 mol) and potassium carbonate (63.4 g, 0.459 mol) were introduced into a 1 L flask, the resulting mixture was diluted with dimethylacetamide (400 mL), the resulting mixture was refluxed and stirred, and reacted for 3 hours, and then the reaction was terminated. After the reaction solvent was distilled under reduced pressure, the organic layer obtained by performing extraction with ethyl acetate and water was treated with anhydrous magnesium sulfate, and then filtered and concentrated, and the resulting product was recrystallized with ethyl acetate and ethanol to obtain <Intermediate 5-2> (33.0 g, yield 85%).

Mass [M+1]=253

Synthesis Example 41

Synthesis of Intermediate 5-3

Intermediate 5-3 was synthesized according to the following reaction formula.

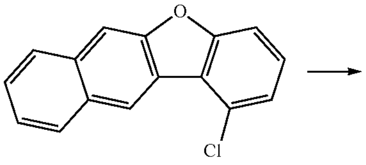

<Intermediate 5-2>

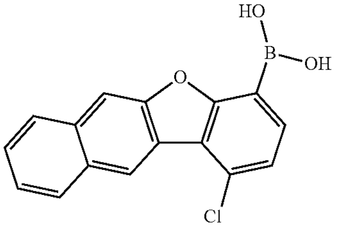

<Intermediate 5-3>

<Intermediate 5-2> (17.0 g, 0.067 mol) and tetrahydrofuran (180 mL) were put into a 0.5 L flask, the flask was transferred to an acetone-dry ice bath to decrease the internal temperature to −78° C., and then a 2.5 M tetrahydrofuran solution (30.9 mL, 0.077 mol) of n-butyllithium was slowly added dropwise thereto, and then the resulting mixture was stirred for 1 hour. Thereafter, trimethyl borate (9.0 mL, 0.081 mol) was slowly added dropwise thereto, and then the resulting mixture was further stirred for 30 minutes. Thereafter, the reaction was terminated 16 hours later, the resulting product was treated with water, and then the organic layer obtained by performing extraction with ethyl acetate and brine was treated with anhydrous magnesium sulfate, and then filtered and concentrated to obtain <Intermediate 5-3> (11.7 g, yield 59%) through recrystallization with ethyl acetate and n-hexane.

The product was confirmed with TLC and HPLC.

Synthesis Example 42

Synthesis of Intermediate 5-4

Intermediate 5-4 was synthesized according to the following reaction formula.

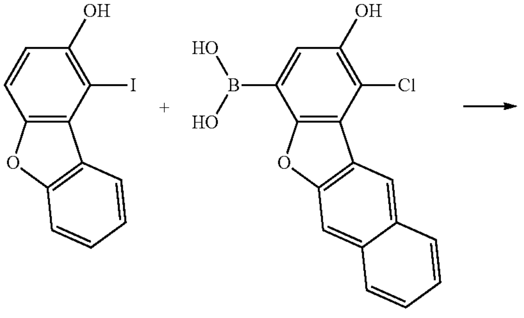

-continued

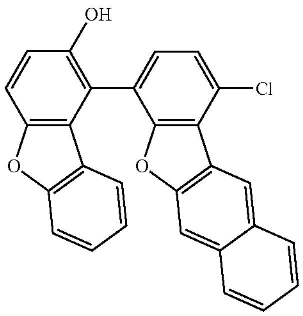

<Intermediate 5-4>

An experiment was performed in the same manner as in Synthesis Example 1 by using <Intermediate 5-3> as a starting material, thereby synthesizing <Intermediate 5-4>.

Mass [M+1]=434

Synthesis Example 43

Synthesis of Intermediate 5-5

Intermediate 5-5 was synthesized according to the following reaction formula.

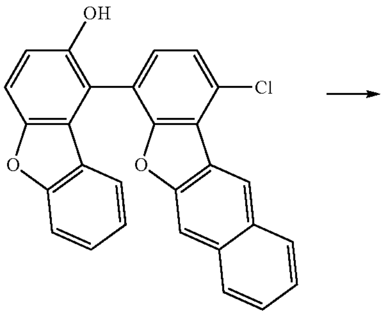

<Intermediate 5-4>

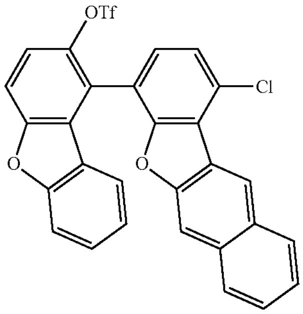

<Intermediate 5-5>

An experiment was performed in the same manner as in Synthesis Example 2 by using <Intermediate 5-4>, thereby synthesizing <Intermediate 5-5>.

The product was confirmed with TLC and HPLC.

Synthesis Example 44

Synthesis of Intermediate 5-6

Intermediate 5-6 was synthesized according to the following reaction formula.

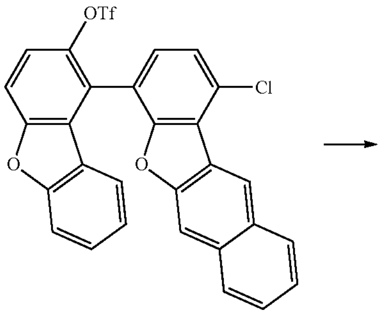

<Intermediate 5-5>

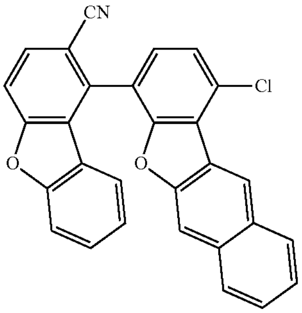

<Intermediate 5-6>

An experiment was performed in the same manner as in Synthesis Example 3 by using <Intermediate 5-5>, thereby synthesizing <Intermediate 5-6>.

Mass [M+1]=444

Synthesis Example 45

Synthesis of Intermediate 5-7

Intermediate 5-7 was synthesized according to the following reaction formula.

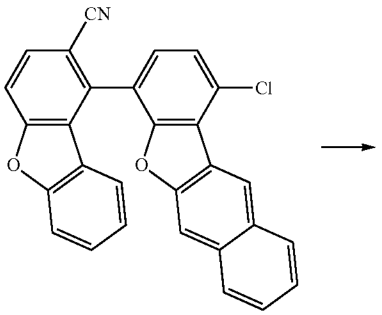

<Intermediate 5-6>

-continued

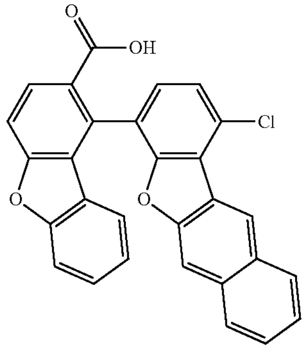

<Intermediate 5-7>

An experiment was performed in the same manner as in Synthesis Example 4 by using <Intermediate 5-6>, thereby synthesizing <Intermediate 5-7>.

The product was confirmed with TLC and HPLC.

Synthesis Example 46

Synthesis of Intermediate 5-8

Intermediate 5-8 was synthesized according to the following reaction formula.

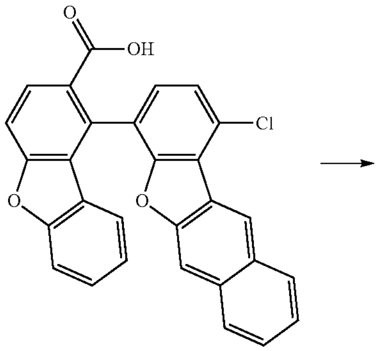

<Intermediate 5-7>

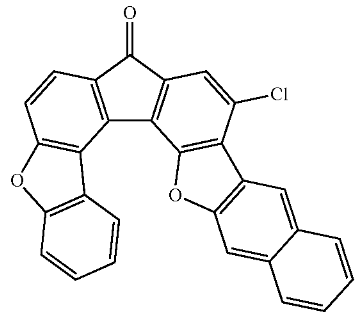

<Intermediate 5-8>

An experiment was performed in the same manner as in Synthesis Example 5 by using <Intermediate 5-7>, thereby synthesizing <Intermediate 5-8>.

Mass [M+1]=445

Synthesis Example 47

Synthesis of Intermediate 5-9

Intermediate 5-9 was synthesized according to the following reaction formula.

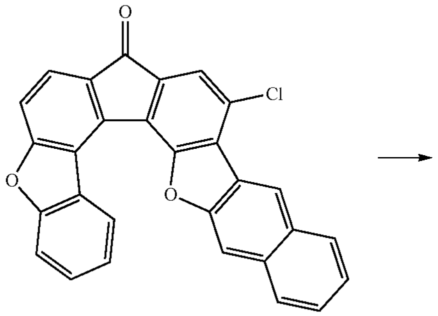

<Intermediate 5-8>

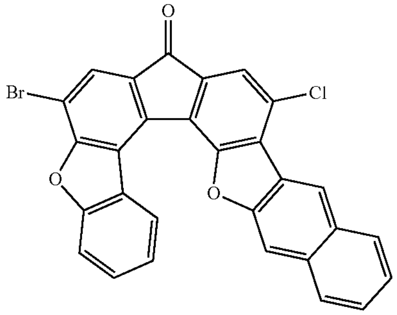

<Intermediate 5-9>

An experiment was performed in the same manner as in Synthesis Example 6 by using <Intermediate 5-8>, thereby synthesizing <Intermediate 5-9>.

Mass [M+1]=523

Synthesis Example 48

Synthesis of Intermediate 5-10

Intermediate 5-10 was synthesized according to the following reaction formula.

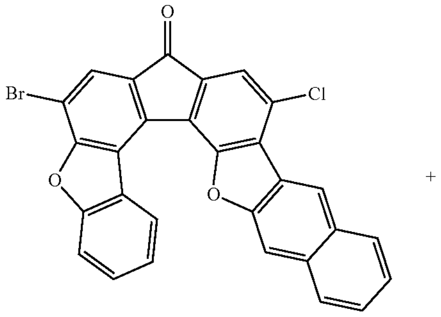

<Intermediate 5-9>

-continued

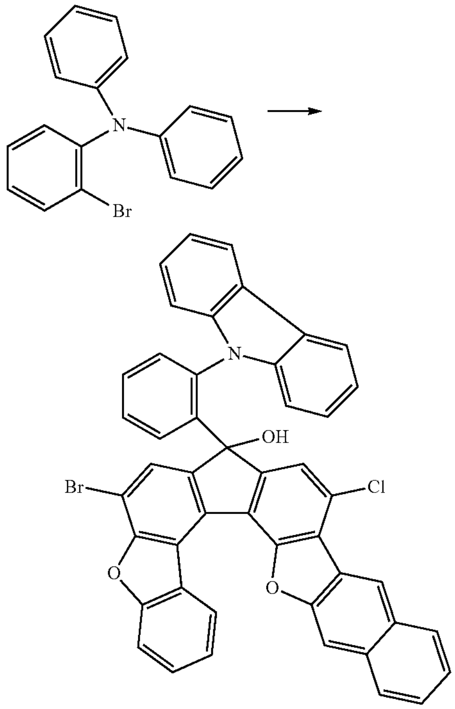

<Intermediate 5-10>

An experiment was performed in the same manner as in Synthesis Example 7 by using <Intermediate 5-9>, thereby synthesizing <Intermediate 5-10>.

Mass [M+1]=766

Synthesis Example 49

Synthesis of Intermediate 5-11

Intermediate 5-11 was synthesized according to the following reaction formula.

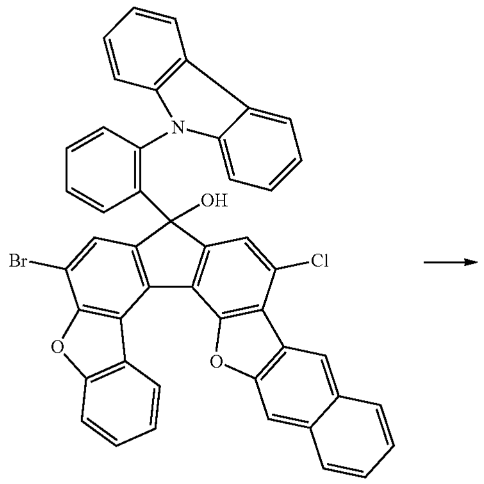

<Intermediate 5-10>

-continued

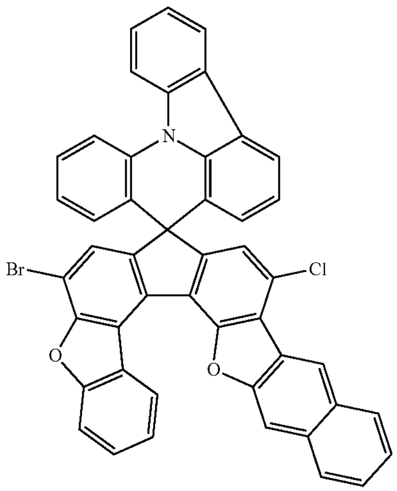

<Intermediate 5-11>

An experiment was performed in the same manner as in Synthesis Example 8 by using <Intermediate 5-10>, thereby synthesizing <Intermediate 5-11>.

Mass [M+1]=748

Synthesis Example 50

Synthesis of Intermediate 2-7

<Intermediate 2-7>was synthesized according to the following reaction formula.

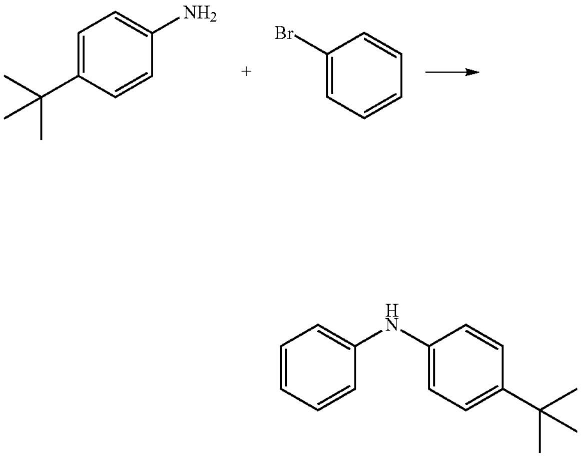

<Intermediate 2-7>

An experiment was performed in the same manner as in Synthesis Example 9 by using 4-t-butylaniline and bromobenzene, thereby synthesizing <Intermediate 2-7>.

Mass [M+1]=226

Synthesis Example 51

Synthesis of Compound 48

Compound 48 was synthesized according to the following reaction formula.

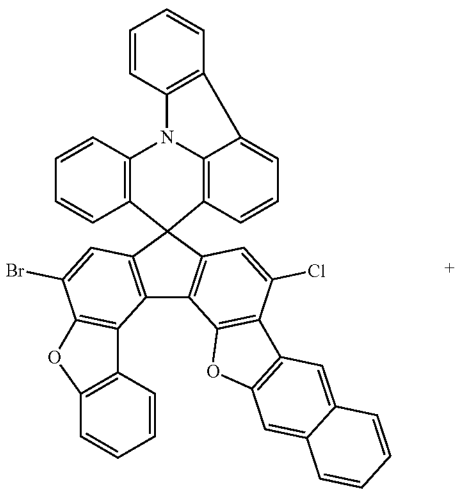

<Intermediate 5-11>

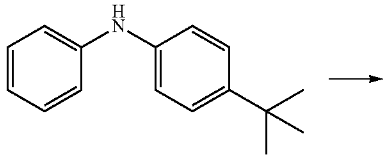

<Intermediate 2-7>

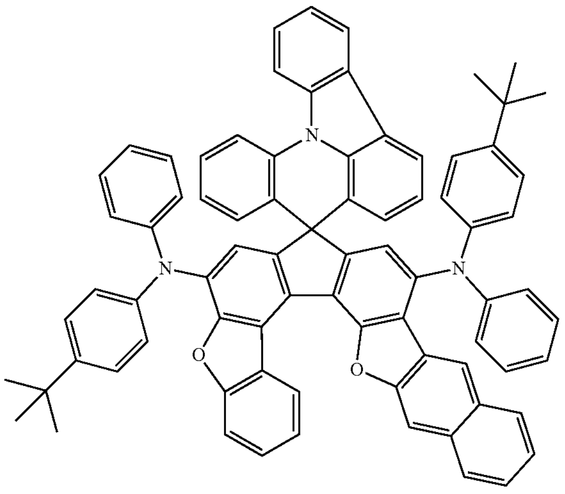

<Compound 24>

An experiment was performed in the same manner as in Synthesis Example 10 by using <Intermediate 5-11>and <Intermediate 2-7>, thereby synthesizing <Compound 48>.

Mass [M+1]=1083

Synthesis Example 52

Synthesis of Intermediate 2-8

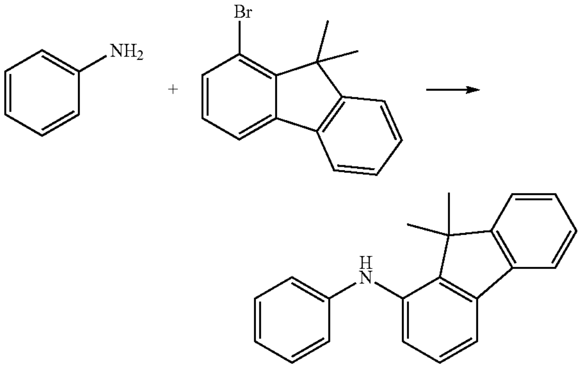

<Intermediate 2-8>

An experiment was performed in the same manner as in Synthesis Example 9 by using aniline and 1-bromo-9,9-dimethylfluorene, thereby synthesizing <Intermediate 2-8>.

Mass [M+1]=226

Synthesis Example 53

Synthesis of Intermediate 6-1

Intermediate 6-1 was synthesized according to the following reaction formula.

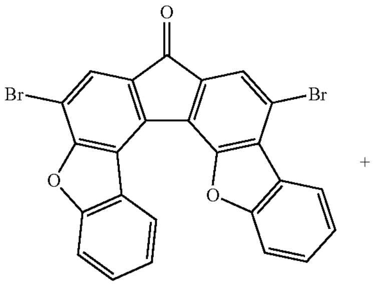

<Intermediate 1-8>

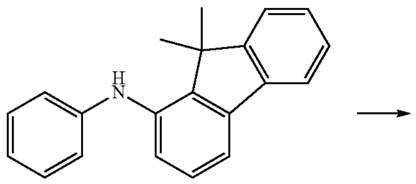

<Intermediate 2-8>

-continued

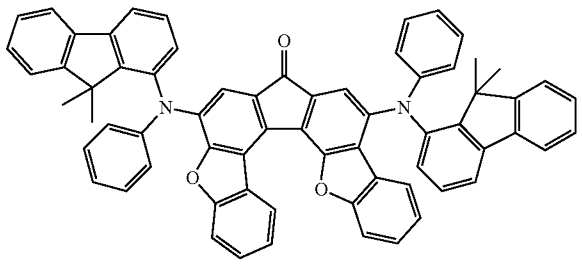

<Intermediate 6-1>

<Intermediate 1-8> (6.5 g, 0.013 mol), <Intermediate 2-8> (9.31 g, 0.033 mol), sodium tert-butoxide (5.42 g, 0.056 mol), and bis(tri-tert-butylphosphine)palladium (0) (0.45 g, 0.88 mmol) were put into 95 mL of toluene in a 0.25 L flask under a nitrogen atmosphere, and the resulting mixture was refluxed and stirred. When the reaction was terminated, the mixture was cooled to room temperature, and then extraction with toluene and water was performed, and the aqueous layer was removed. The remaining product was treated with anhydrous magnesium sulfate, and then filtered and concentrated under reduced pressure. The product was separated and purified with a column chromatography method, and then <Intermediate 6-1> (7.2 g, yield 62%) was obtained.

Mass [M+1]=927

Synthesis Example 54

Synthesis of Intermediate 6-2

Intermediate 6-2 was synthesized according to the following reaction formula.

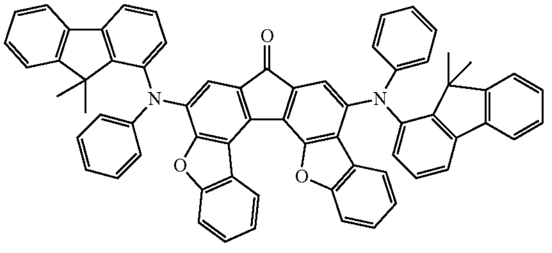

<Intermediate 6-1>

+

-continued

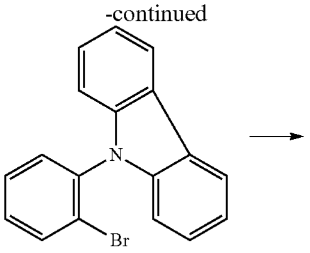

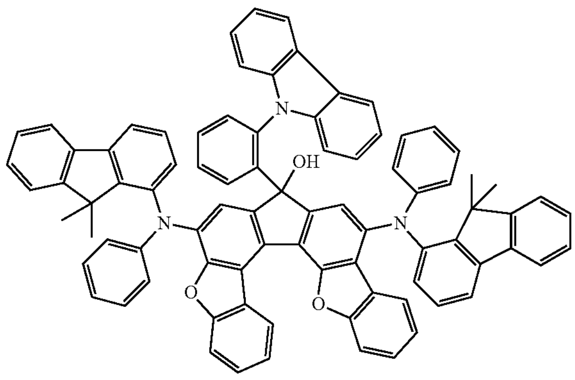

<Intermediate 6-2>

9-(2-bromophenyl)-9H-carbazole (2.5 g, 7.68 mmol) and 100 mL of tetrahydrofuran were put into under a nitrogen atmosphere, and the resulting mixture was cooled to −78° C. A 2.5 M tetrahydrofuran solution (3.57 mL, 8.92 mmol) of n-butyllithium was added dropwise to the cooled reaction solution, and then the resulting mixture was stirred at the same temperature for 1 hour. Thereafter, <Intermediate 6-2> (7.20 g, 7.76 mmol) was introduced thereinto at the same temperature, and then the resulting mixture was slowly warmed to room temperature and stirred for 18 hours. After the completion of the reaction, the reaction was terminated by adding water thereto, and then extraction with ethyl acetate and water was performed. The organic layer was treated with anhydrous magnesium sulfate, and then filtered and concentrated under reduced pressure. From the solid obtained by the reaction, <Intermediate 1-7> (5.6 g, yield 62%) was obtained by using a silica gel column chromatography method with ethyl acetate and hexane.

Mass [M+1]=1171

Synthesis Example 55
Synthesis of Compound 49
Compound 49 was synthesized according to the following reaction formula.
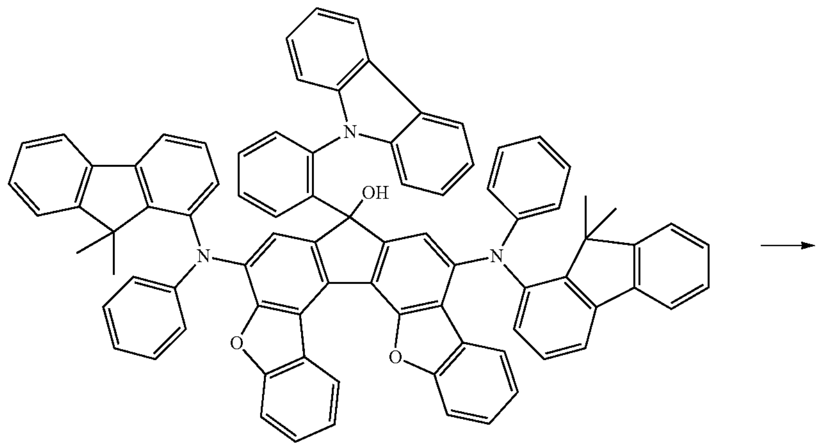
<Intermediate 6-1>
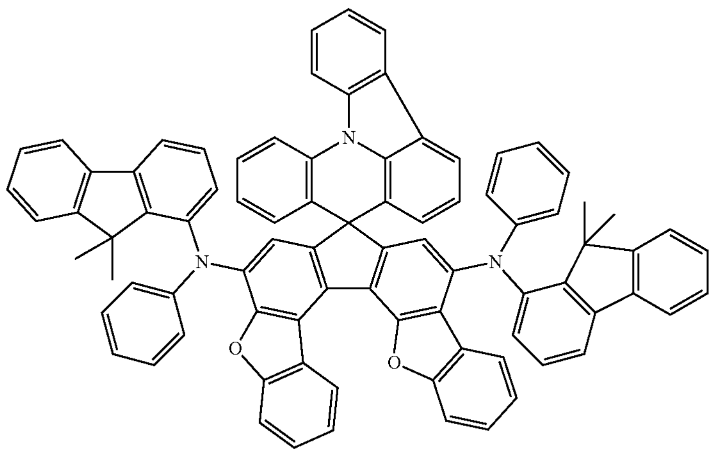
<Compound 49>

<Intermediate 6-1> (3.2 g, 4.20 mmol), acetic acid (100 mL), and two drops of sulfuric acid were put into, and the resulting mixture was heated and stirred at a temperature of 80° C. for 2 hours. After the completion of the reaction, the produced solid was filtered, and then washed with ethanol. The obtained solid was separated and purified by a column chromatography method, and then recrystallized again to obtain <Compound 49> (15 g, yield 62%).

Mass [M+1]=1152

Synthesis Example 56

Synthesis of Intermediate 2-8

<Intermediate 2-8> was synthesized according to the following reaction formula.

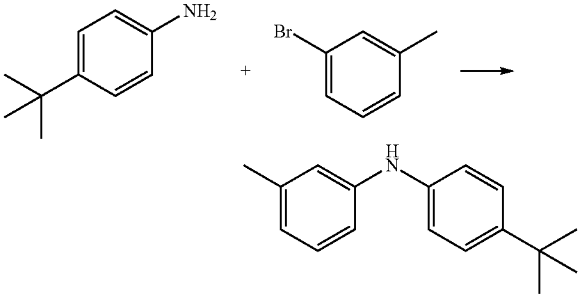

<Intermediate 2-8>

An experiment was performed in the same manner as in Synthesis Example 9 by using 4-t-butylaniline and 1-bromo-3-methylbenzene, thereby synthesizing <Intermediate 2-8>.

Mass [M+1]=226

Synthesis Example 57

Synthesis of Compound 47

Compound 47 was synthesized according to the following reaction formula.

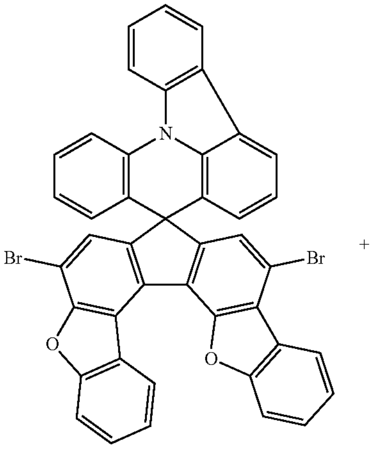

<Intermediate 1-8>

-continued

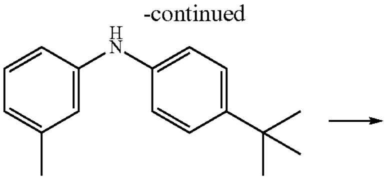

<Intermediate 2-8>

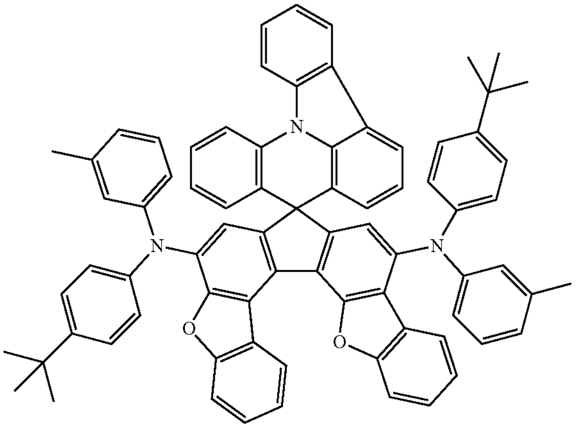

<Compound 47>

An experiment was performed in the same manner as in Synthesis Example 10 by using <Intermediate 1-8> and N-(4-tert-butyl)phenyl-3-methylaniline, thereby synthesizing Compound 47. The NMR data of Compound 47 are illustrated in the following FIG. 4.

Mass [M+1]=1061

Synthesis Example 58

Synthesis of Intermediate 7-1

Intermediate 7-1 was synthesized according to the following reaction formula.

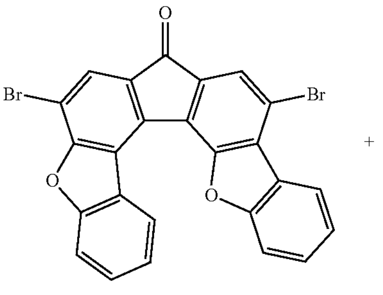

<Intermediate 1-6>

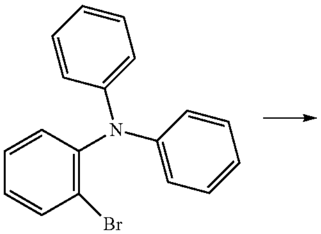

-continued

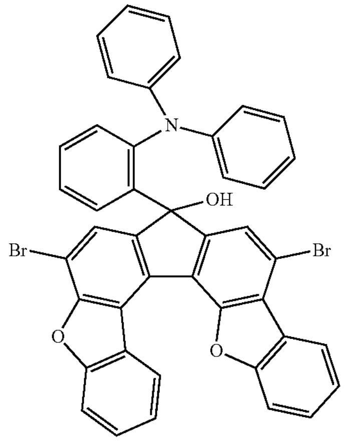

<Intermediate 7-1>

An experiment was performed in the same manner as in Synthesis Example 7 by using <Intermediate 1-6> and 2-bromo-N,N-diphenylaniline, thereby synthesizing <Intermediate 7-1>.

Mass [M+1]=763

Synthesis Example 59

Synthesis of Compound 60

Compound 60 was synthesized according to the following reaction formula.

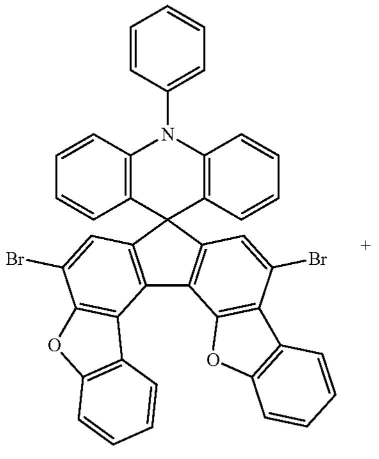

<Intermediate 7-1>

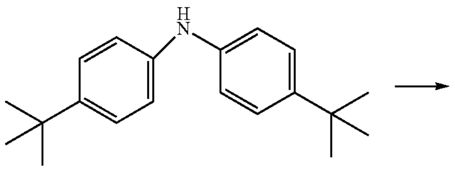

-continued

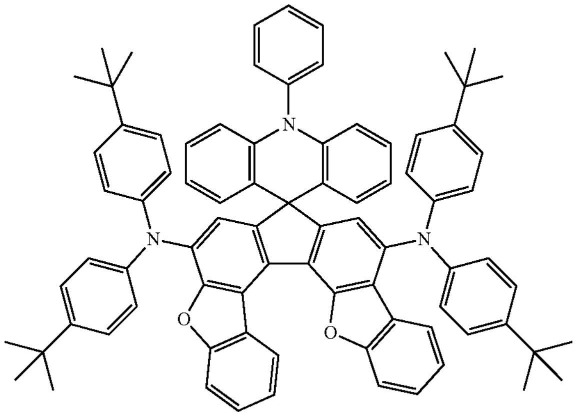

<Compound 60>

An experiment was performed in the same manner as in Synthesis Example 10 by using <Intermediate 7-1> and bis(4-(tert-butyl)phenyl)amine, thereby synthesizing Compound 60. The Mass data of Compound 60 are illustrated in the following FIG. 5.

Mass [M+1]=1147

Through the method which is the same as the synthesis methods described in the Synthesis Examples, it is possible to synthesize the compound corresponding to Chemical Formula 1 of the present application in addition to the compounds synthesized in the Synthesis Examples.

EXAMPLES

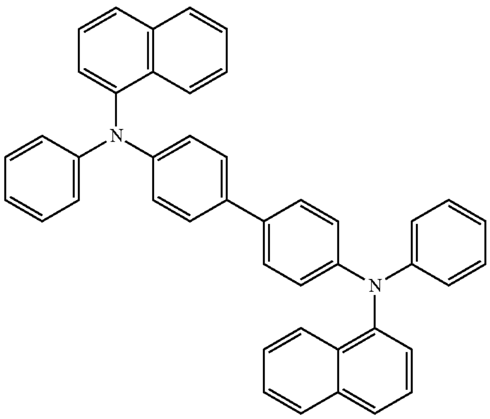

HT-A

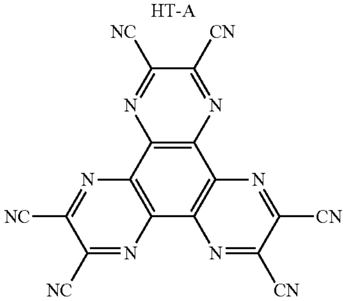

HAT

-continued
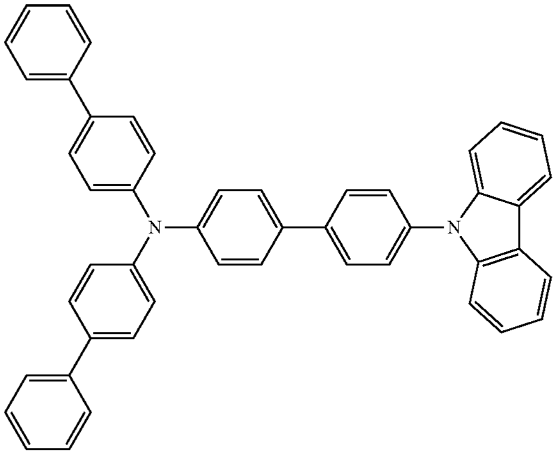
HT-B
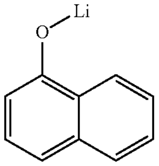
Liq
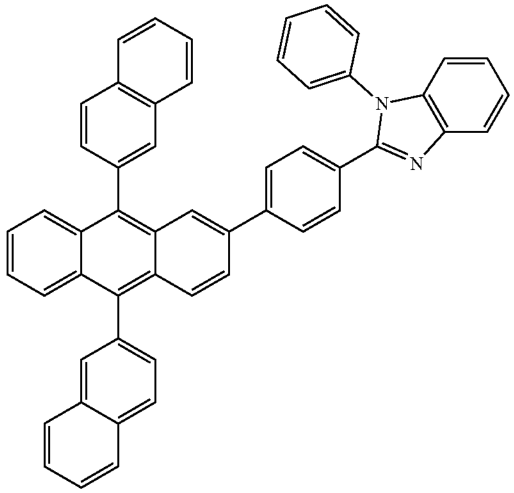
ET-A
-continued
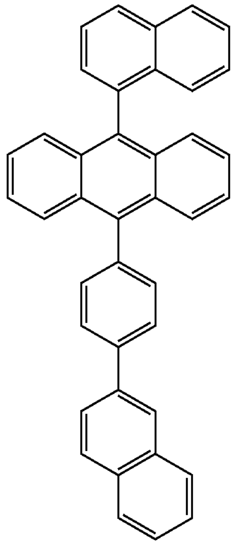
H-A
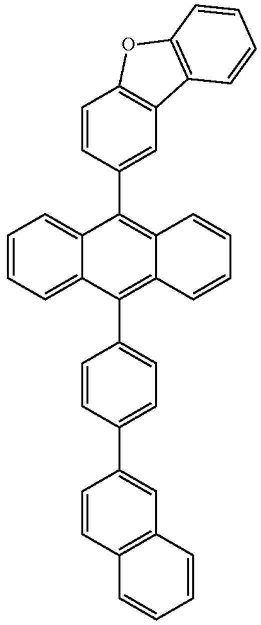
H-B
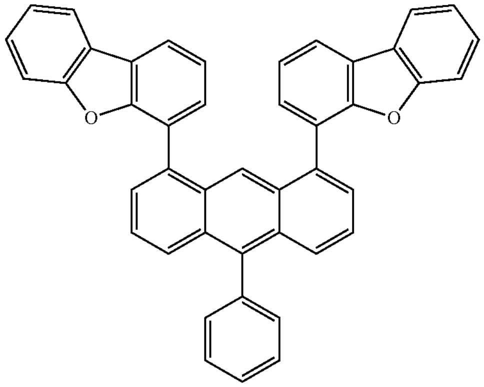
H-C
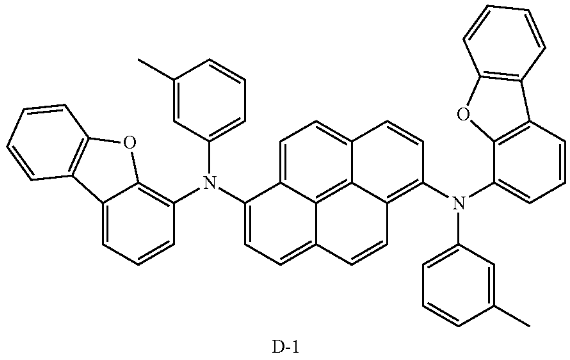
D-1

-continued

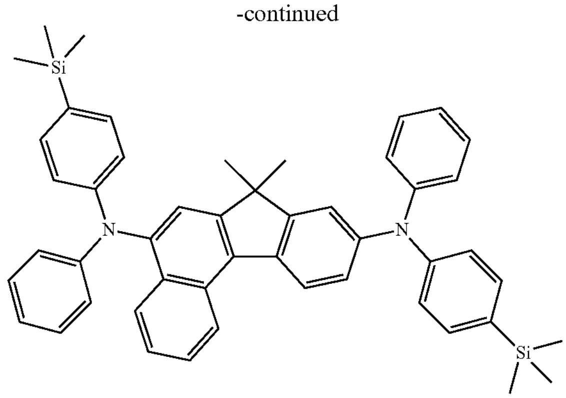

D-2

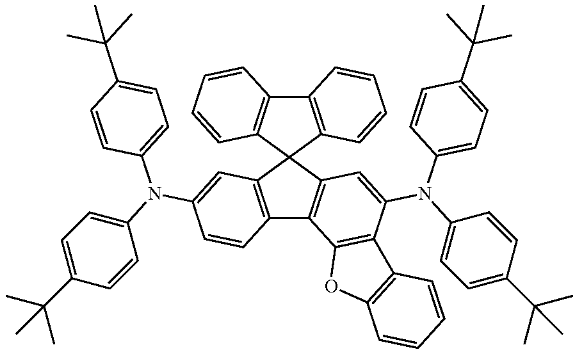

D-3

Example 1

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

HAT was thermally vacuum deposited to have a thickness of 50 Å on the ITO transparent electrode thus prepared, thereby forming a hole injection layer. The following HT-A was vacuum deposited as a hole transporting layer to have a thickness of 1,000 Å thereon, and subsequently, HT-B was deposited to have a thickness of 100 Å. The light emitting layer was doped with H-A as a host and Compound 1 in an amount of 2 to 10 wt %, and vacuum deposited to have a thickness of 200 Å. Next, ET-A and Liq were deposited at a ratio of 1:1 to have a thickness of 300 Å, and magnesium (Mg) doped with 10 wt % of silver (Ag) and having a thickness of 150 Å and aluminum having a thickness of 1,000 Å were deposited thereon to form a negative electrode, thereby manufacturing an organic light emitting device.

In the aforementioned procedure, the deposition rates of the organic material, LiF, and aluminum were maintained at 1 Å/sec, 0.2 Å/sec, and 3 to 7 Å/sec, respectively.

Example 2

An organic light emitting device was manufactured in the same manner as in Example 1, except that Compound 5 was used instead of Compound 1 in Example 1.

Example 3

An organic light emitting device was manufactured in the same manner as in Example 1, except that Compound 17 was used instead of Compound 1 in Example 1.

Example 4

An organic light emitting device was manufactured in the same manner as in Example 1, except that Compound 25 was used instead of Compound 1 in Example 1.

Example 5

An organic light emitting device was manufactured in the same manner as in Example 1, except that Compound 42 was used instead of Compound 1 in Example 1.

Example 6

An organic light emitting device was manufactured in the same manner as in Example 1, except that Compound 48 was used instead of Compound 1 in Example 1.

Example 7

An organic light emitting device was manufactured in the same manner as in Example 1, except that H-B was used instead of the host H-A in Example 1.

Example 8

An organic light emitting device was manufactured in the same manner as in Example 7, except that Compound 5 was used instead of Compound 1 in Example 7.

Example 9

An organic light emitting device was manufactured in the same manner as in Example 7, except that Compound 17 was used instead of Compound 1 in Example 7.

Example 10

An organic light emitting device was manufactured in the same manner as in Example 7, except that Compound 25 was used instead of Compound 1 in Example 7.

Example 11

An organic light emitting device was manufactured in the same manner as in Example 7, except that Compound 42 was used instead of Compound 1 in Example 7.

Example 12

An organic light emitting device was manufactured in the same manner as in Example 7, except that Compound 48 was used instead of Compound 1 in Example 7.

Example 13

An organic light emitting device was manufactured in the same manner as in Example 13, except that H-C was used instead of the host H-A in Example 1.

Example 14

An organic light emitting device was manufactured in the same manner as in Example 13, except that Compound 5 was used instead of Compound 1 in Example 13.

Example 15

An organic light emitting device was manufactured in the same manner as in Example 13, except that Compound 17 was used instead of Compound 1 in Example 13.

Example 16

An organic light emitting device was manufactured in the same manner as in Example 13, except that Compound 25 was used instead of Compound 1 in Example 13.

Example 17

An organic light emitting device was manufactured in the same manner as in Example 13, except that Compound 42 was used instead of Compound 1 in Example 13.

Example 18

An organic light emitting device was manufactured in the same manner as in Example 13, except that Compound 48 was used instead of Compound 1 in Example 13.

COMPARATIVE EXAMPLE

Comparative Example 1

An organic light emitting device was manufactured in the same manner as in Example 1, except that D-1 was used instead of Compound 1 in Example 1.

Comparative Example 2

An organic light emitting device was manufactured in the same manner as in Example 1, except that D-2 was used instead of Compound 1 in Example 1.

Comparative Example 3

An organic light emitting device was manufactured in the same manner as in Example 1, except that D-3 was used instead of Compound 1 in Example 1.

Comparative Example 4

An organic light emitting device was manufactured in the same manner as in Example 7, except that D-1 was used instead of Compound 1 in Example 7.

Comparative Example 5

An organic light emitting device was manufactured in the same manner as in Example 7, except that D-2 was used instead of Compound 1 in Example 7.

Comparative Example 6

An organic light emitting device was manufactured in the same manner as in Example 7, except that D-3 was used instead of Compound 1 in Example 7.

Comparative Example 7

An organic light emitting device was manufactured in the same manner as in Example 13, except that D-1 was used instead of Compound 1 in Example 13.

Comparative Example 8

An organic light emitting device was manufactured in the same manner as in Example 13, except that D-2 was used instead of Compound 1 in Example 13.

Comparative Example 9

An organic light emitting device was manufactured in the same manner as in Example 13, except that D-3 was used instead of Compound 1 in Example 13.

For the organic light emitting devices of Examples 1 to 18 and Comparative Examples 1 to 9, the driving voltage and the light emitting efficiency were measured at a current density of 10 mA/cm, and a time (LT95) for reaching a 95% value compared to the initial luminance was measured at a current density of 20 mA/cm. The results are shown in the following Table 1.

TABLE 1

| | | | @10 mA/cm$^2$ | | | @20 mA/cm$^2$ |
|---|---|---|---|---|---|---|
| Example | Host | Dopant | Voltage (V) | Efficiency (cd/A) | CIE (x, y) | Service life (hr) |
| Example 1 | H-A | Compound 1 | 4.1 | 6.25 | (0.141, 0.043) | 160 |
| Example 2 | H-A | Compound 5 | 4.2 | 6.22 | (0.141, 0.042) | 150 |
| Example 3 | H-A | Compound 17 | 4.5 | 6.34 | (0.142, 0.042) | 160 |
| Example 4 | H-A | Compound 25 | 4.1 | 5.80 | (0.143, 0.043) | 155 |
| Example 5 | H-A | Compound 42 | 4.0 | 6.25 | (0.143, 0.043) | 165 |
| Example 6 | H-A | Compound 48 | 4.3 | 5.60 | (0.144, 0.046) | 130 |
| Example 7 | H-B | Compound 1 | 4.0 | 6.10 | (0.141, 0.043) | 160 |
| Example 8 | H-B | Compound 5 | 4.2 | 6.25 | (0.141, 0.042) | 130 |
| Example 9 | H-B | Compound 17 | 4.0 | 6.05 | (0.142, 0.043) | 145 |
| Example 10 | H-B | Compound 25 | 4.0 | 5.85 | (0.143, 0.043) | 140 |
| Example 11 | H-B | Compound 42 | 3.9 | 6.15 | (0.143, 0.043) | 135 |
| Example 12 | H-B | Compound 48 | 4.3 | 5.80 | (0.144, 0.046) | 155 |
| Example 13 | H-C | Compound 1 | 4.2 | 5.90 | (0.141, 0.046) | 170 |
| Example 14 | H-C | Compound 5 | 4.3 | 5.80 | (0.141, 0.045) | 165 |
| Example 15 | H-C | Compound 17 | 4.5 | 6.00 | (0.143, 0.045) | 140 |
| Example 16 | H-C | Compound 25 | 4.2 | 5.60 | (0.143, 0.043) | 165 |
| Example 17 | H-C | Compound 42 | 4.2 | 5.90 | (0.143, 0.043) | 155 |

TABLE 1-continued

| Example | Host | Dopant | @10 mA/cm$^2$ Voltage (V) | @10 mA/cm$^2$ Efficiency (cd/A) | @10 mA/cm$^2$ CIE (x, y) | @20 mA/cm$^2$ Service life (hr) |
|---|---|---|---|---|---|---|
| Example 18 | H-C | Compound 48 | 4.4 | 5.50 | (0.144, 0.048) | 150 |
| Comparative Example 1 | H-A | D-1 | 4.4 | 5.13 | (0.144, 0.045) | 75 |
| Comparative Example 2 | H-A | D-2 | 4.4 | 3.50 | (0.142, 0.045) | 50 |
| Comparative Example 3 | H-A | D-3 | 4.3 | 5.12 | (0.142, 0.046) | 85 |
| Comparative Example 4 | H-B | D-1 | 4.3 | 5.03 | (0.143, 0.042) | 80 |
| Comparative Example 5 | H-B | D-2 | 4.2 | 3.61 | (0.141, 0.045) | 50 |
| Comparative Example 6 | H-B | D-3 | 4.3 | 5.22 | (0.142, 0.045) | 70 |
| Comparative Example 7 | H-C | D-1 | 4.1 | 4.98 | (0.144, 0.045) | 80 |
| Comparative Example 8 | H-C | D-2 | 4.2 | 3.66 | (0.141, 0.044) | 55 |
| Comparative Example 9 | H-C | D-3 | 4.2 | 5.12 | (0.142, 0.046) | 90 |

When Examples 1 to 18 and Comparative Examples 1 to 9 in Table 1 are compared with each other, the case of the organic light emitting device manufactured by comprising the compound represented by Chemical Formula 1 exhibits excellent performance by preventing intermolecular fluorescence quenching caused by intermolecular dense packing due to the 3-dimensional structure. Further, in a state where one electron is lost (cation condition), the electron density distribution of HOMO is distributed at a spiro indolo acridine portion including nitrogen known to have a generally stable cation state, thereby bringing about an improvement in service life of the device. Therefore, it can be confirmed that the organic light emitting devices manufactured in Examples 1 to 18 have better efficiency and service life characteristics than those of the organic light emitting devices manufactured in Comparative Examples 1 to 9, which include a pyrene-based or fluorene-based compound.

EXPLANATION OF REFERENCE NUMERALS AND SYMBOLS

10, 11: Organic light emitting device

20: Substrate

30: First electrode

40: Light emitting layer

50: Second electrode

60: Hole injection layer

70: Hole transporting layer

80: Electron blocking layer

90: Electron transporting layer

100: Electron injection layer

The invention claimed is:

1. A compound represented by the following Chemical Formula 4 or 5:

[Chemical Formula 4]

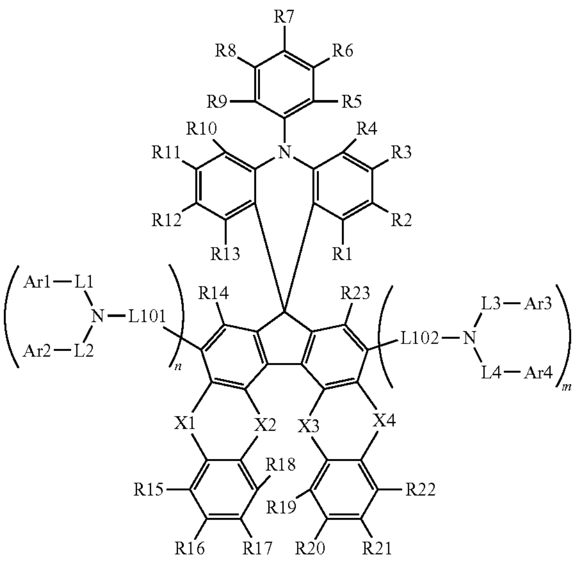

[Chemical Formula 5]

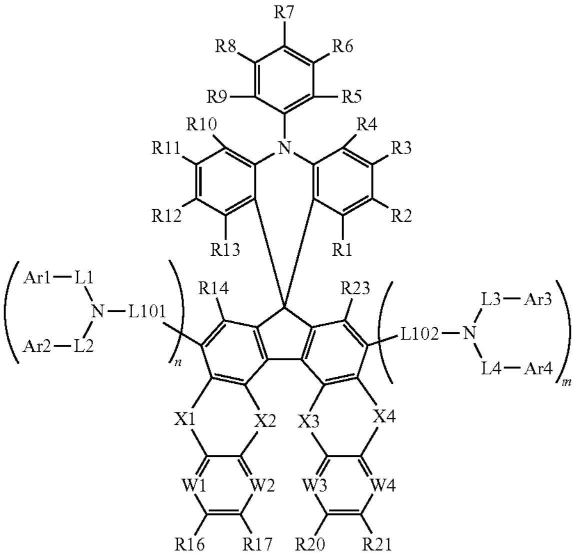

in Chemical Formulae 4 and 5, any one of X1 and X2 is a direct bond, and the other is O, S, or CY1Y2, any one of X3 and X4 is a direct bond, and the other is O, S, or CY3Y4, W1 to W4 are the same as or different from each other, and are each independently N or CRa, and one or more of W1 to W4 are N, and Y1 to Y4 are the same as or different from each other, and are each independently an alkyl group having 1 to 20 carbon atoms, Ra, R14 and R23 are hydrogen, R15 to R22 are hydrogen; or form an aromatic hydrocarbon ring having 6 to 30 carbon atoms by bonding to an adjacent group among Ra, and R14 to R23, L101, L102, and L1 to L4 are each a direct bond, Arl to Ar4 are the same as or different from each other, and are each independently a substituted or unsubstituted phenyl group; a substituted or unsubstituted naphthyl group; a substituted or unsubstituted biphenyl group; a substituted or unsubstituted fluorenyl group; a substituted or unsubstituted pyridyl group; a substituted or unsubstituted dibenzofuran group; a substituted or unsubstituted dibenzothiophene group; or the moieties

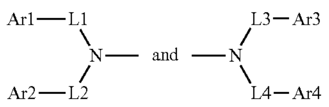

of the Chemical

Formula 4 or 5 can be each independently a substituted or unsubstituted carbazole, R1 to R9 are the same as or different from each other, and are each independently hydrogen; deuterium; or an alkyl group having 1 to 20 carbon atoms, R10 to R13 are hydrogen, R4 and R5 are bonded to each other to form a pentagonal ring, m and n are an integer of 0 or 1, and at least one of m and n is an integer of 1.

2. The compound of claim 1, wherein the compound of Chemical Formula 4 or 5 is represented by one of the following Chemical Formulae 10 to 13 and Chemical Formulae 18 to 21:

[Chemical Formula 10]

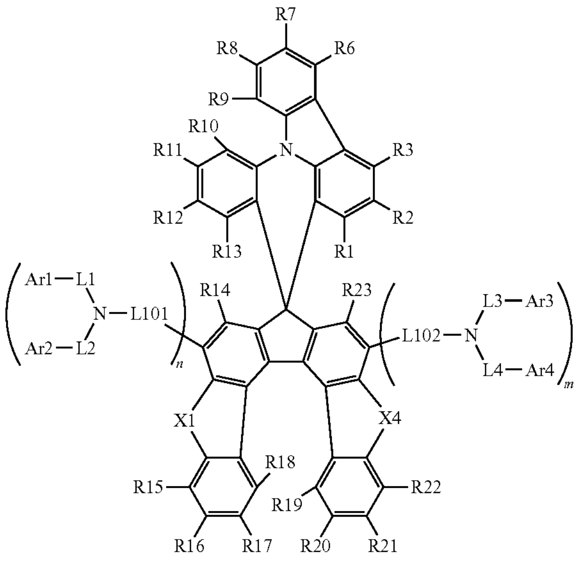

-continued

[Chemical Formula 11]

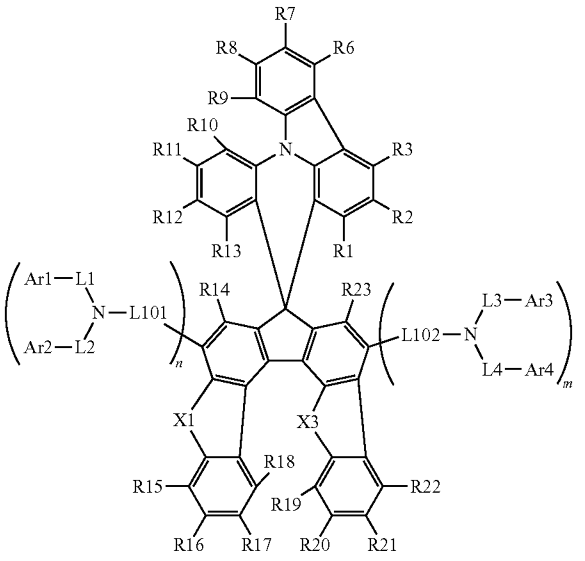

[Chemical Formula 12]

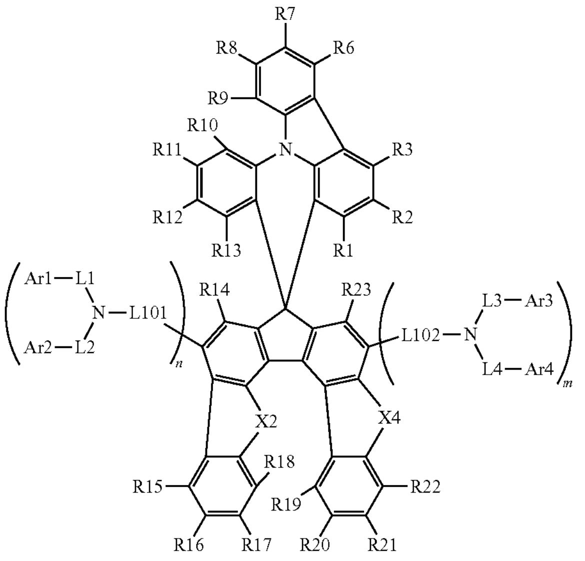

-continued
[Chemical Formula 13]
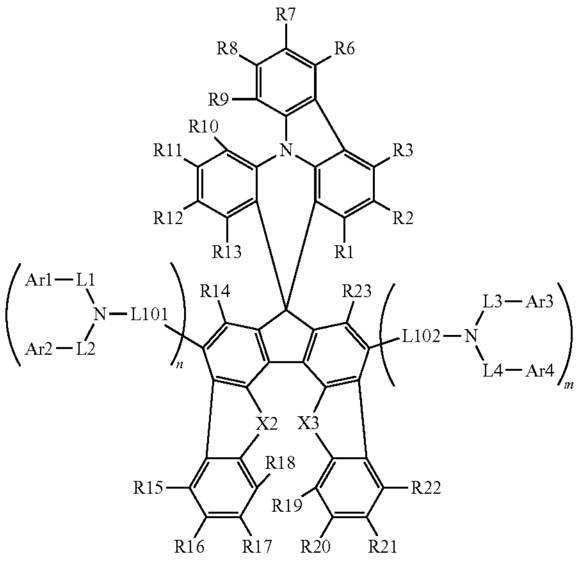
[Chemical Formula 18]
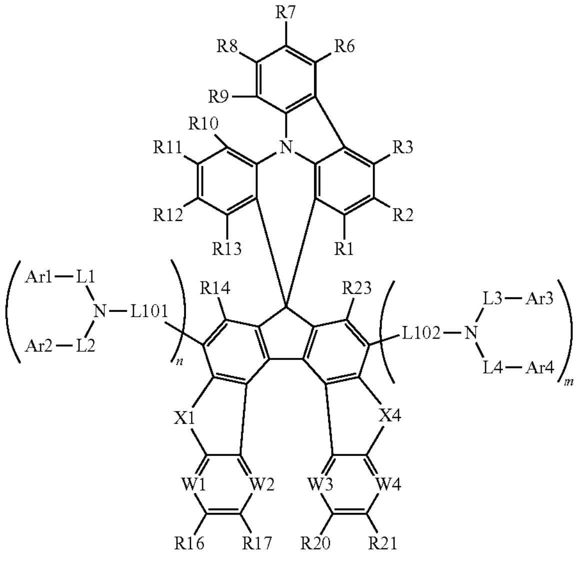
-continued
[Chemical Formula 19]
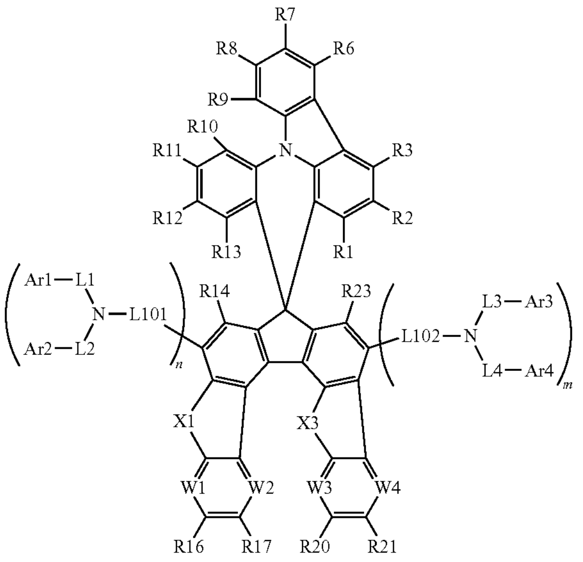
[Chemical Formula 20]
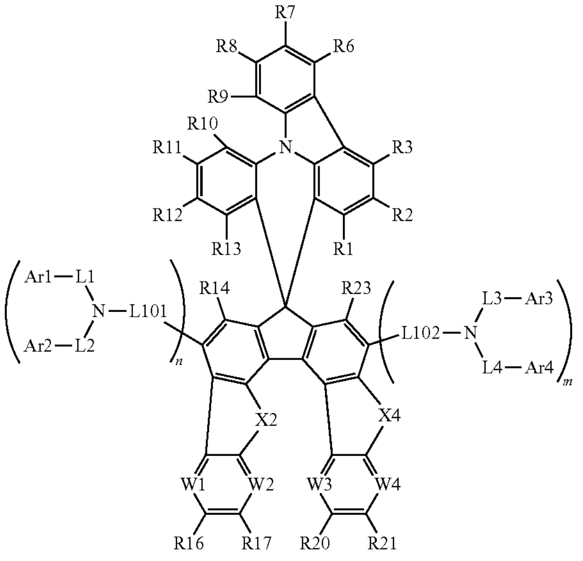

-continued

[Chemical Formula 21]

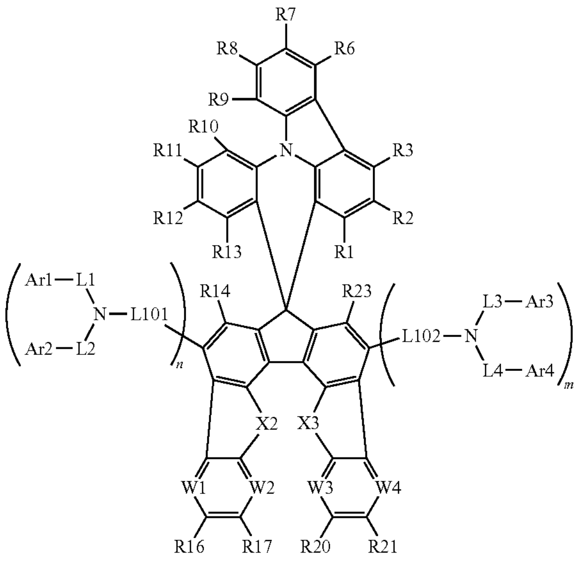

in Chemical Formulae 10 to 13 and Chemical Formulae 18 to 21,

L101, L102, L1 to L4, Ar1 to Ar4, R1 to R3, R6 to R23, m, n, X1 to X4, and W1 to W4 are the same as defined in Chemical Formulae 4 and 5.

3. The compound of claim 1, wherein Ar1 to Ar4 are any one selected from the substituents described below:

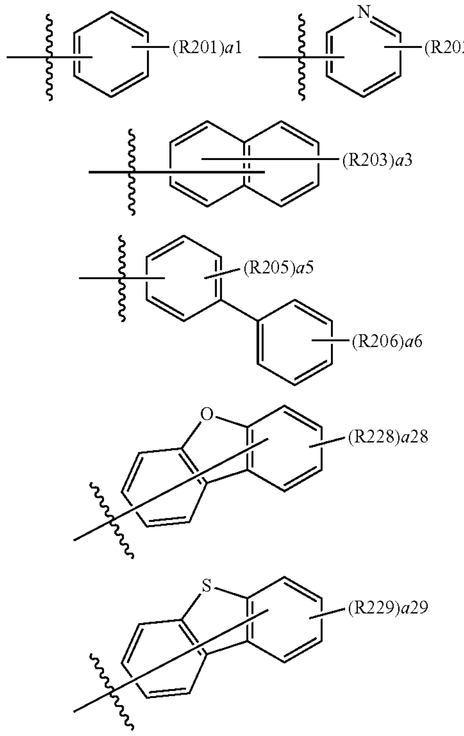

-continued

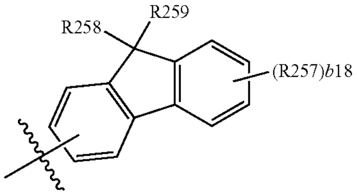

in the structures,

R201, R203, R205, R206, and R257 to R259 are the same as or different from each other, and are each independently hydrogen; deuterium; a halogen group; a nitrile group; a silyl group; or an alkyl group having 1 to 20 carbon atoms, R202, R228, and R229 are the same as or different from each other, and are each independently hydrogen; or an alkyl group having 1 to 20 carbon atoms, and a1 to a3, a5, a6, a8, a9, and b18 are each an integer of 0 or 1.

4. The compound of claim 1, wherein the compound of Chemical Formula 4 or 5 is any one selected from the following compounds:

Compound 1

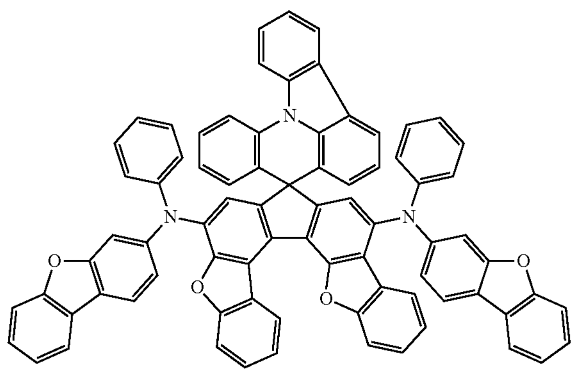

Compound 2

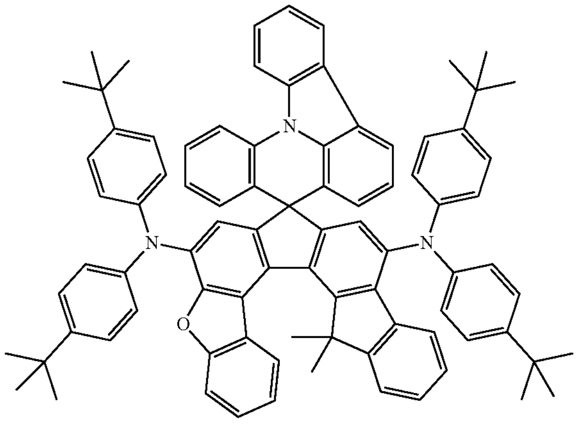

Compound 3
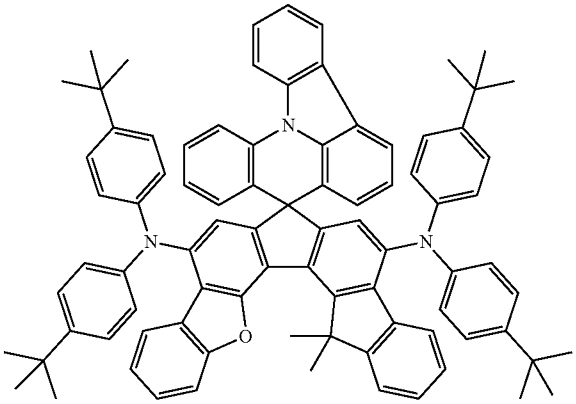
Compound 4
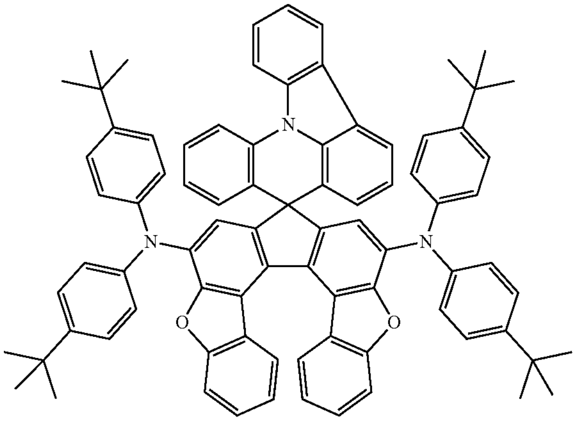
Compound 5
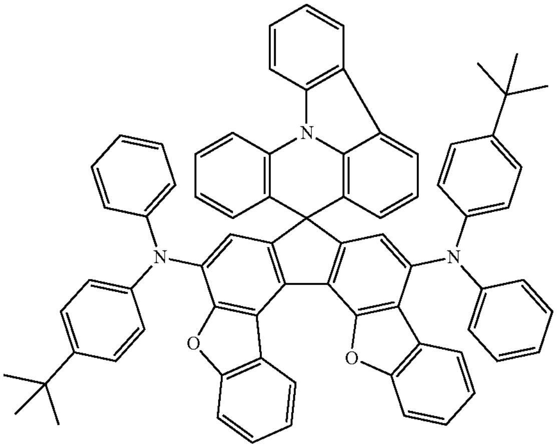
Compound 6
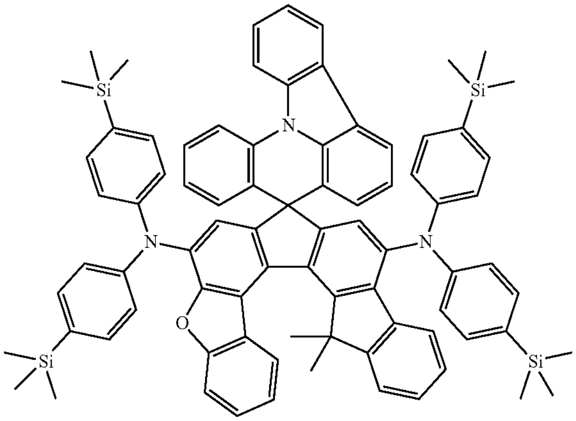
Compound 9
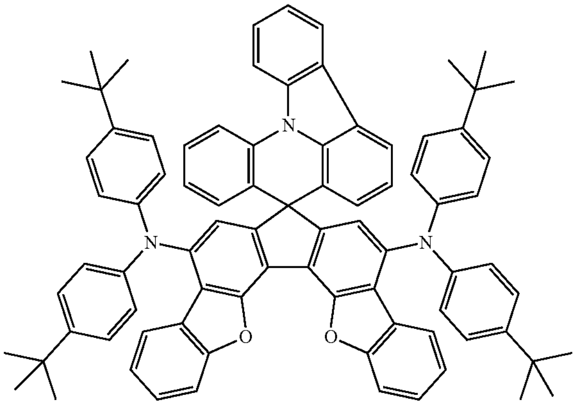
Compound 10
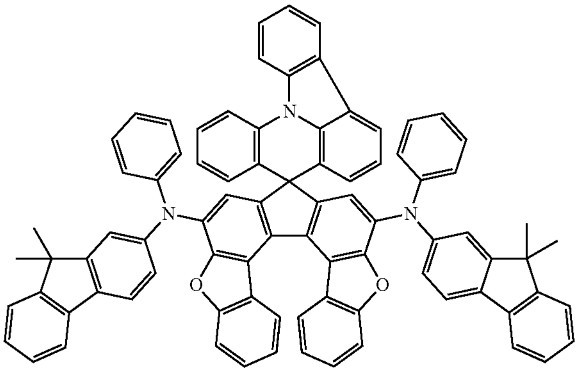
Compound 11
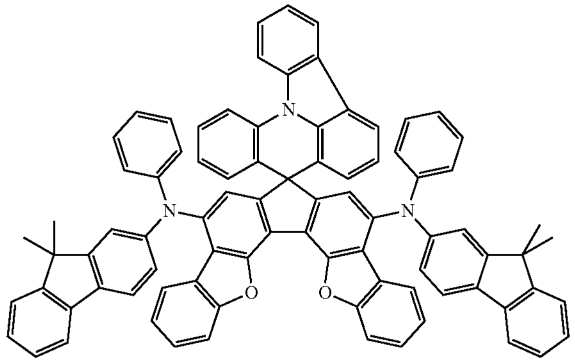

-continued
Compound 13
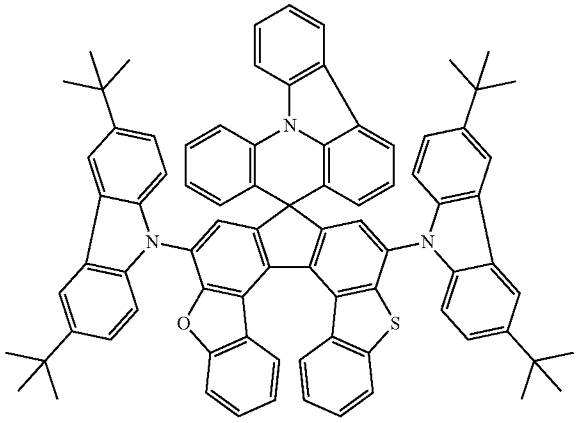
Compound 14
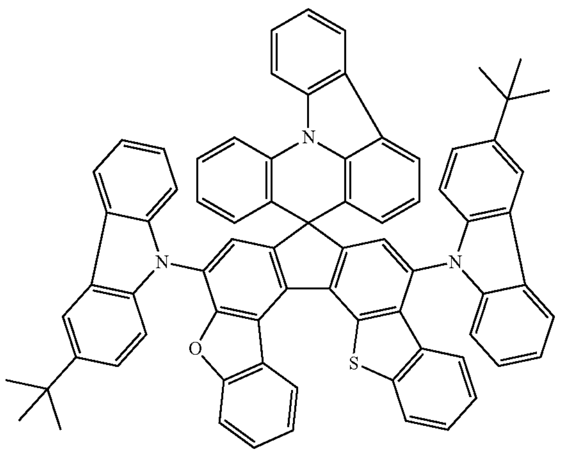
Compound 15
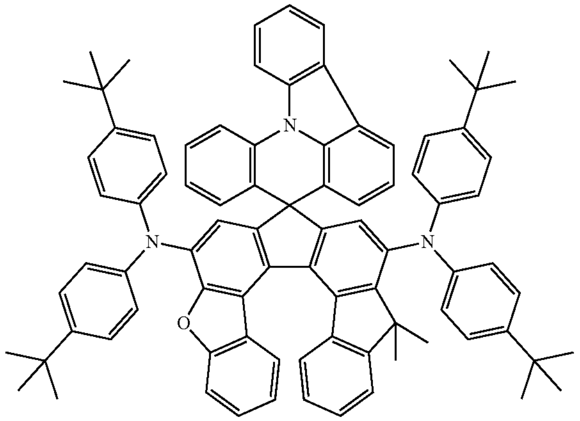
-continued
Compound 16
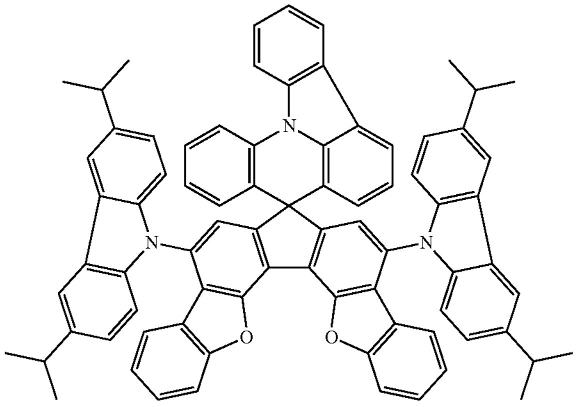
Compound 17
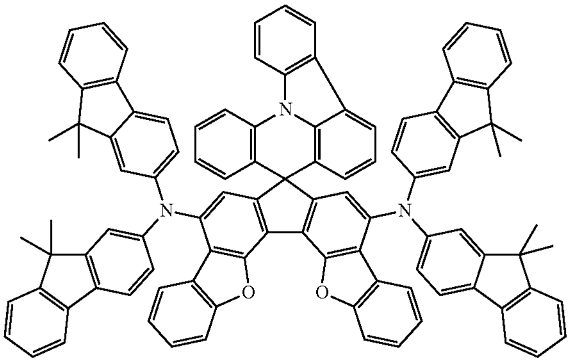
Compound 18
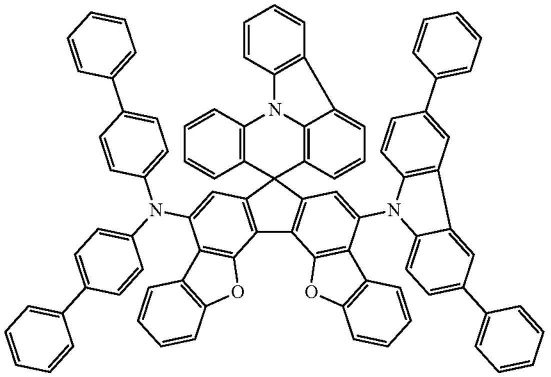

-continued
Compound 19
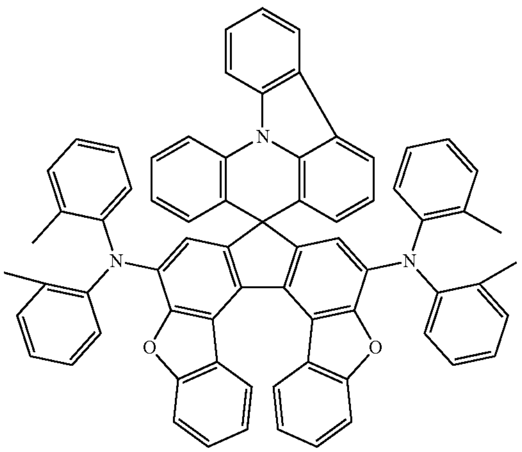
Compound 20
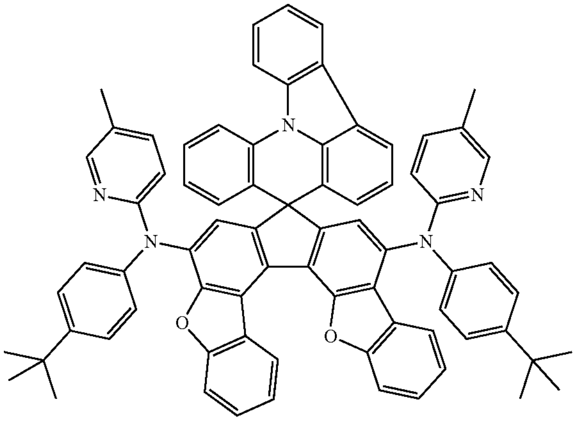
Compound 21
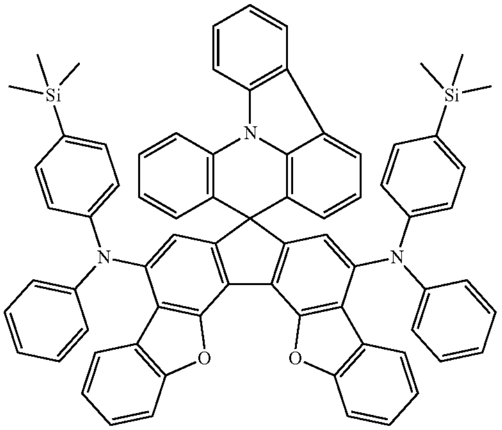
-continued
Compound 22
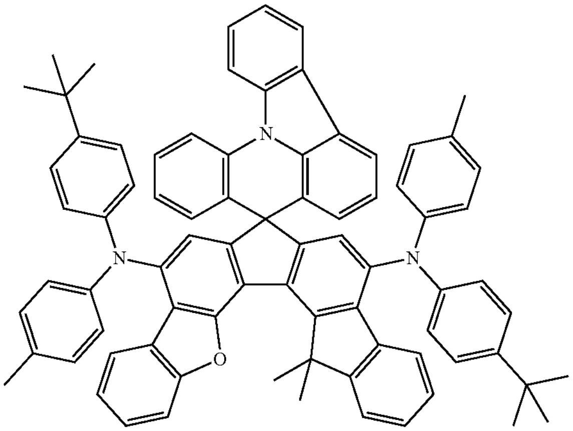
Compound 24
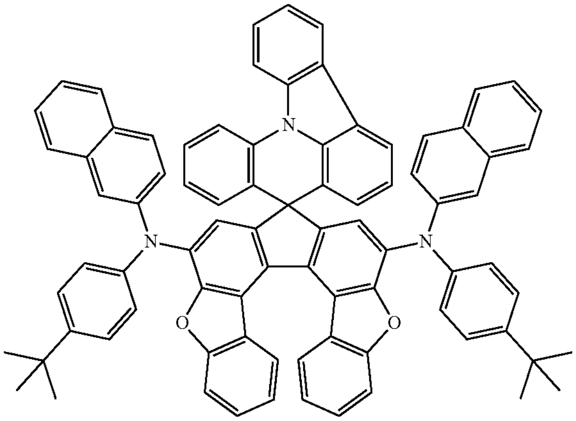
Compound 25
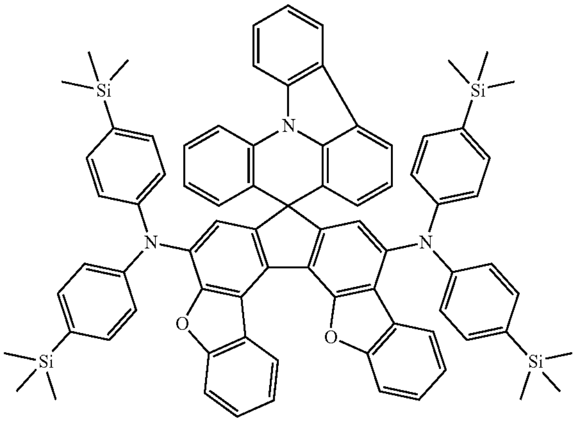

-continued
Compound 26
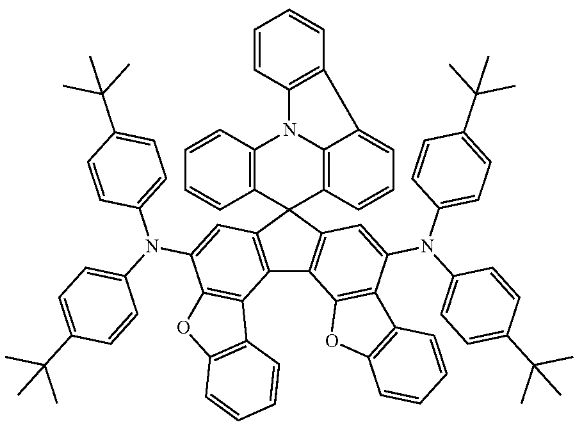
Compound 28
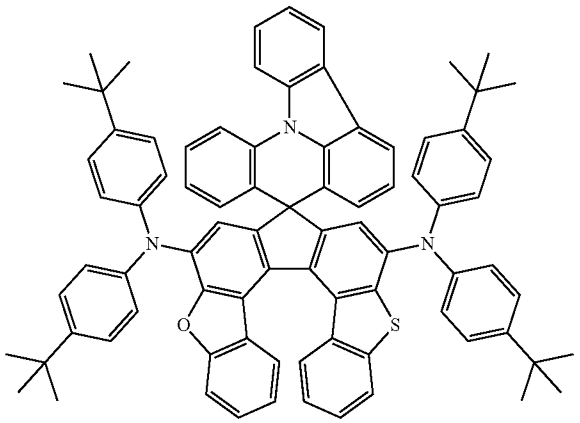
Compound 29
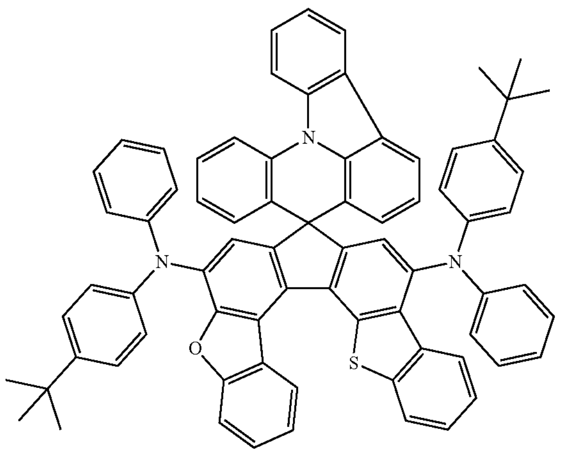
-continued
Compound 30
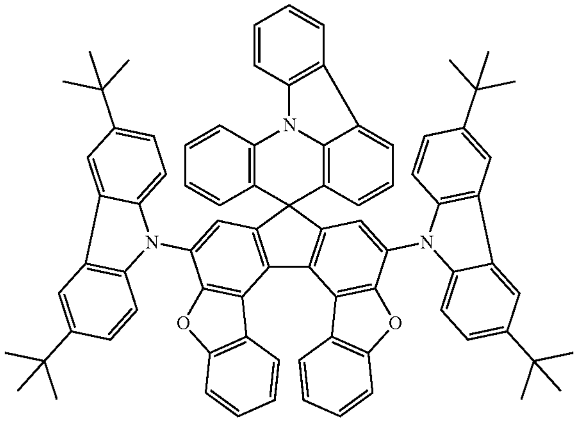
Compound 31
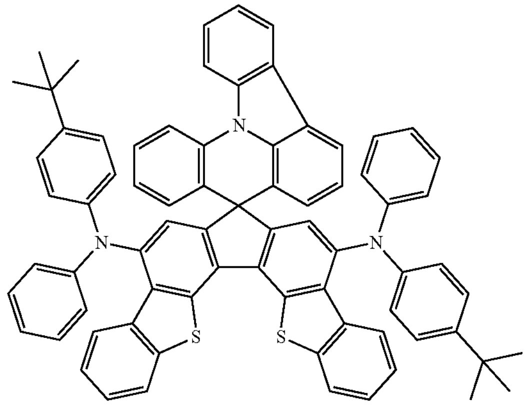
Compound 32
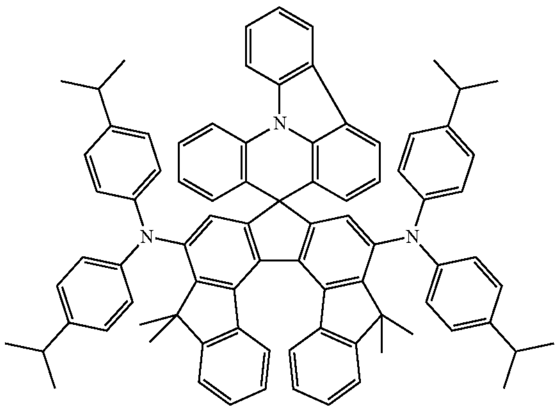

-continued
Compound 34
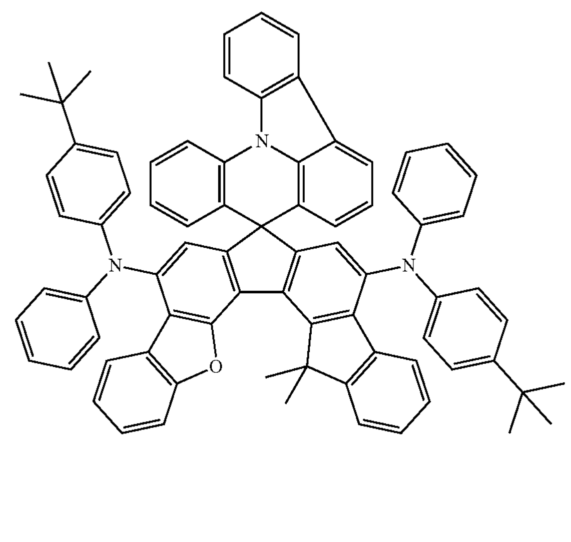
Compound 35
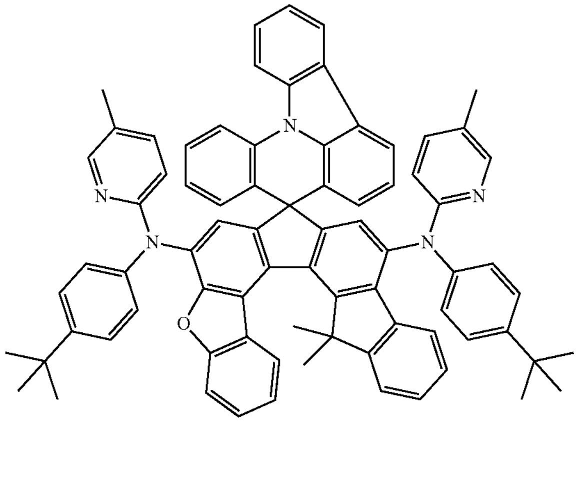
Compound 36
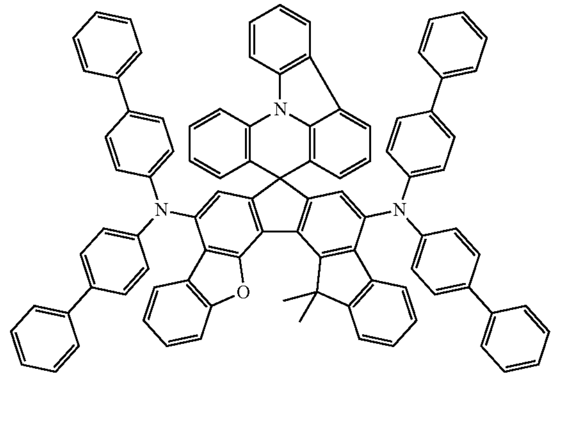
-continued
Compound 37
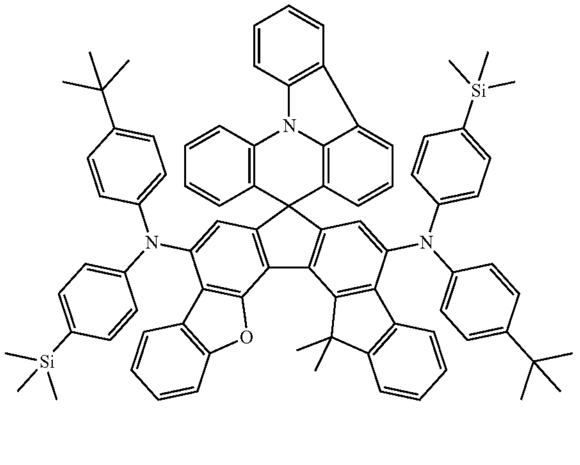
Compound 38
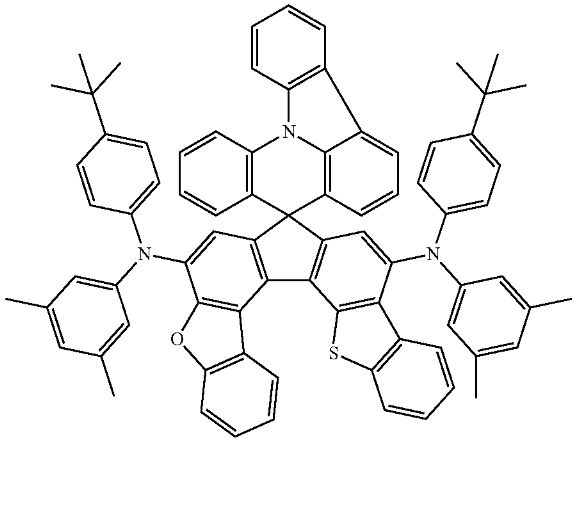
Compound 41
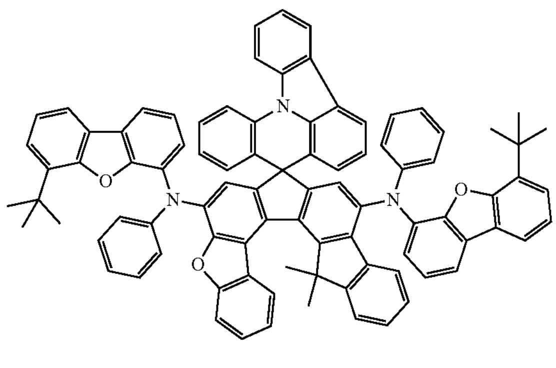

Compound 42
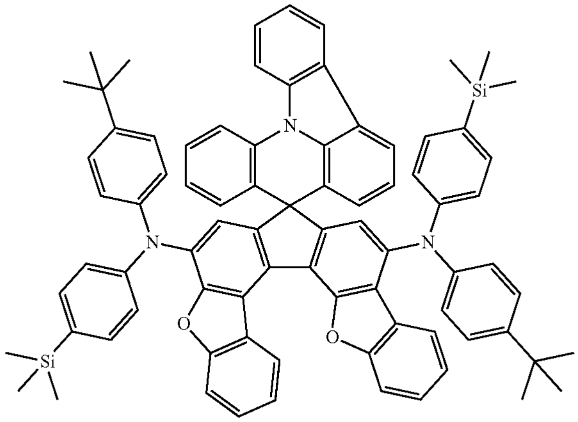
Compound 43
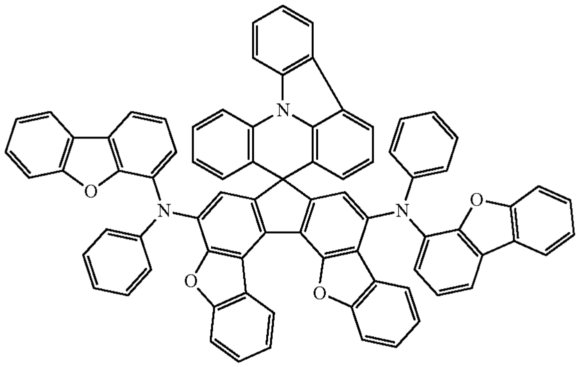
Compound 44
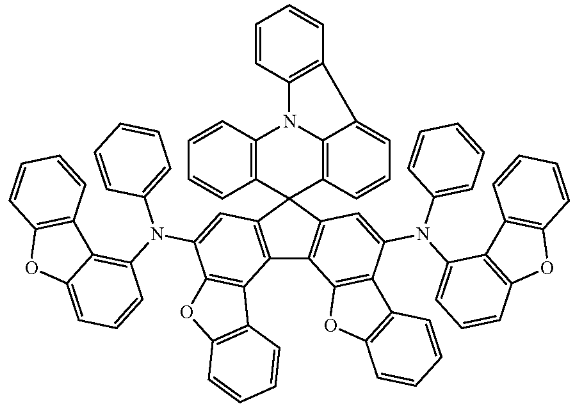
Compound 45
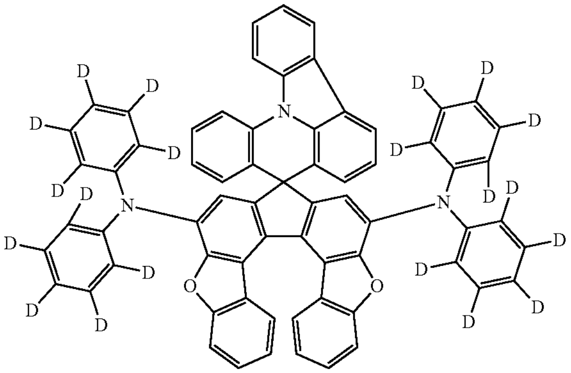
Compound 46
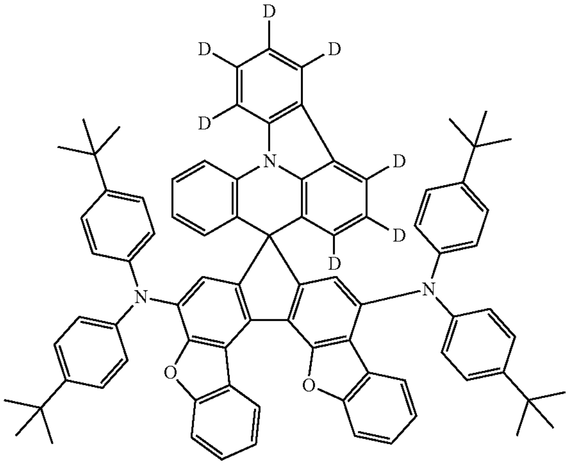
Compound 47
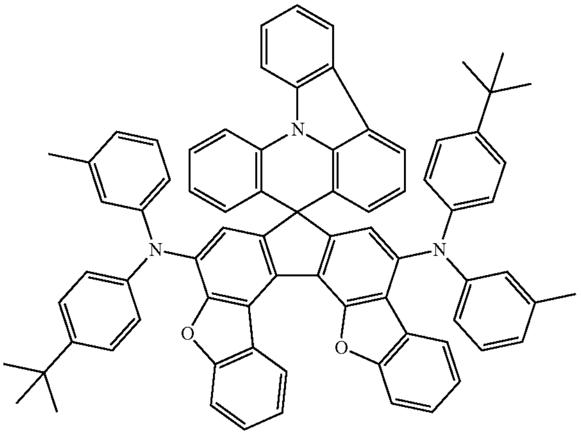
Compound 48
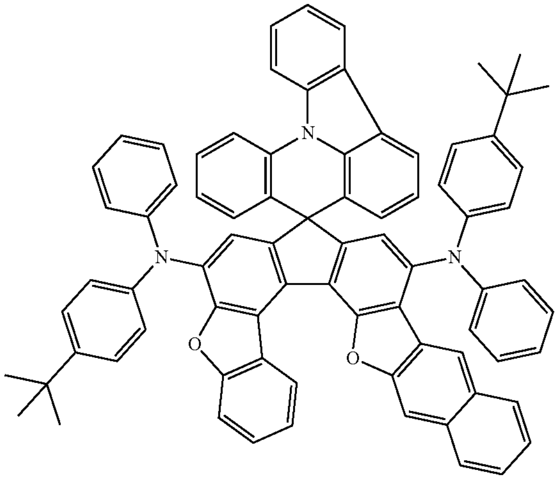

Compound 49
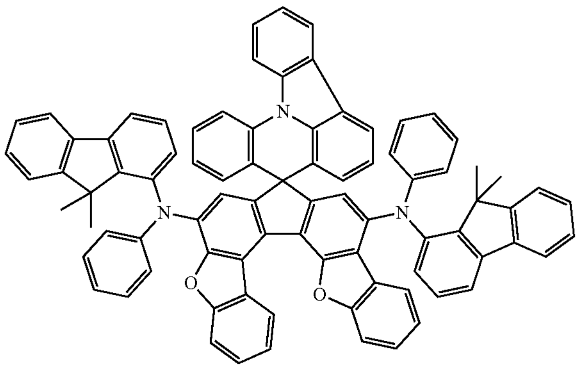
Compound 50
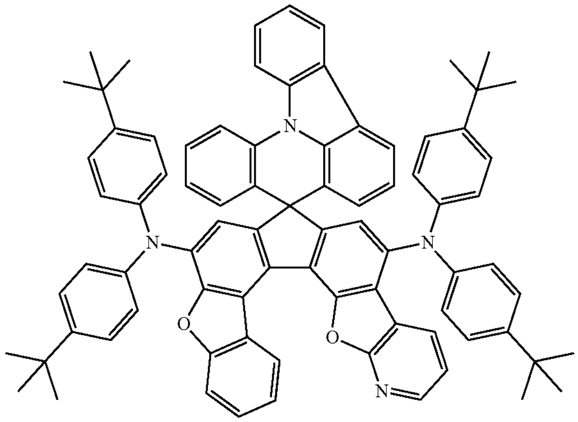
Compound 51
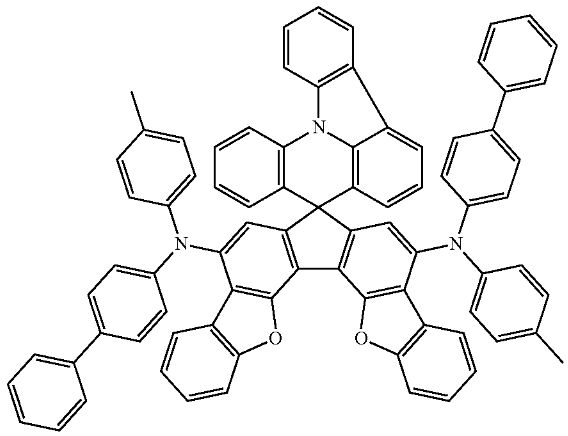
Compound 52
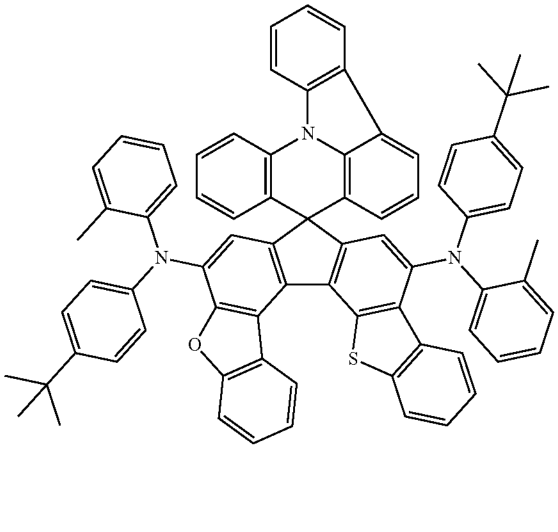
Compound 54
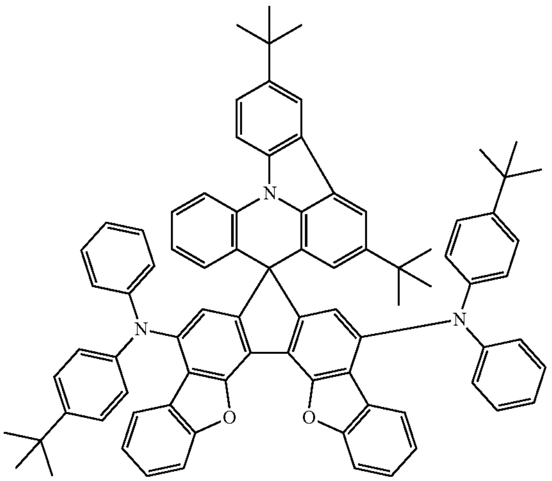
Compound 55
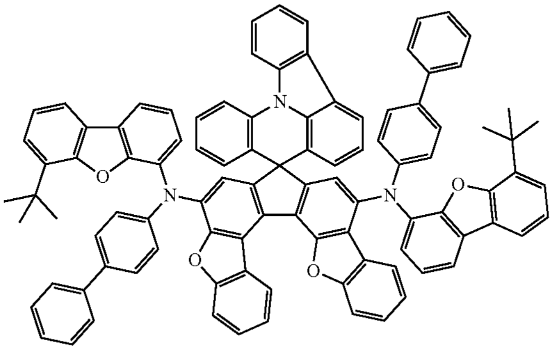

-continued

Compound 56

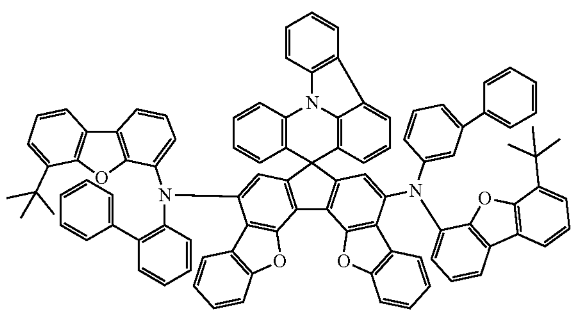

Compound 57

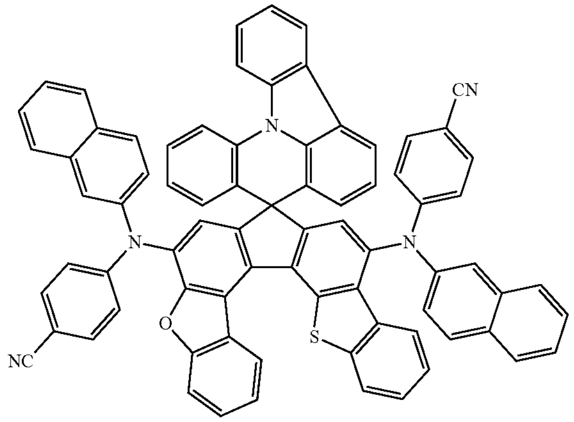

Compound 58

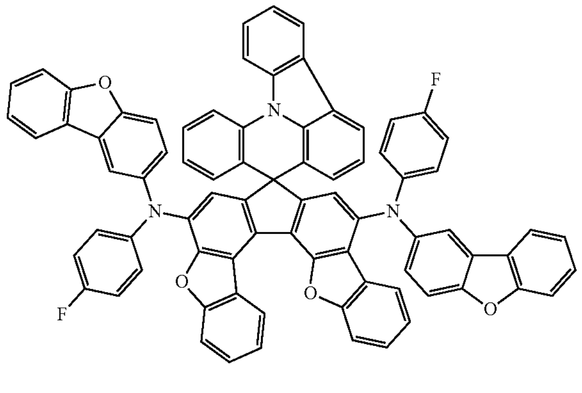

Compound 59

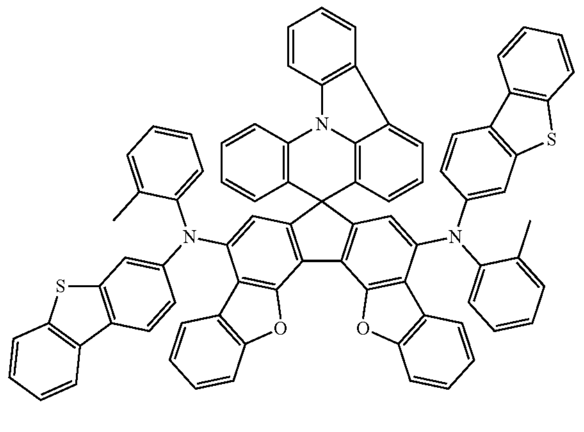

-continued

Compound 62

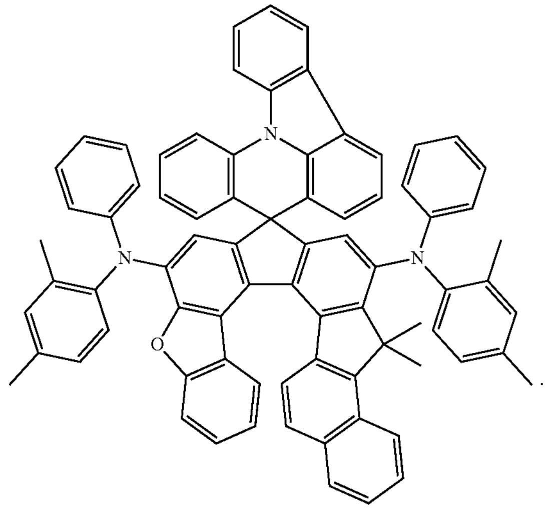

5. An organic electronic device comprising:

a first electrode;

a second electrode disposed to face the first electrode; and an organic material layer having one or more layers disposed between the first electrode and the second electrode, wherein the organic material layer comprises a light emitting layer, and the light emitting layer comprises the compound of claim 1 as a dopant of the light emitting layer.

6. The organic electronic device of claim 5, wherein the organic material layer comprises a light emitting layer, and the light emitting layer comprises a compound represented by the following Chemical Formula 1A:

[Chemical Formula 1A]

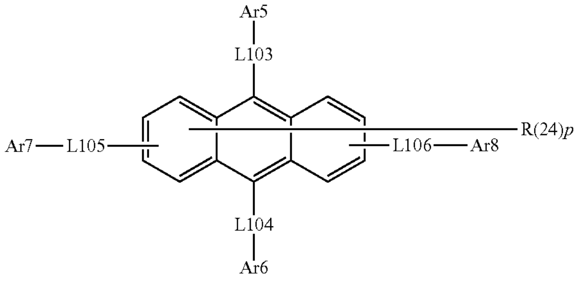

in Chemical Formula 1A,

L103 to L106 are the same as or different from each other, and are each independently a direct bond; a substituted or unsubstituted arylene group; or a substituted or unsubstituted heteroarylene group, Ar5 to Ar8 are the same as or different from each other, and are each independently hydrogen; a substituted or unsubstituted aryl group; or a substituted or unsubstituted heteroaryl group, R24s are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, p is an integer from 0 to 6, and when p is 2 or more, substituents in the parenthesis are the same as or different from each other.

7. The organic electronic device of claim 6, wherein Ar5 to Ar8 are the same as or different from each other, and are each independently hydrogen; or selected from the following structures:

RA1

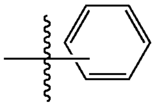

RA2

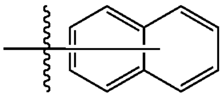

RA3

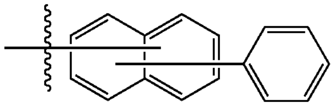

RA4

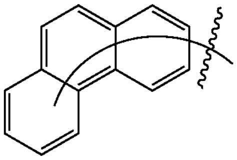

RA5

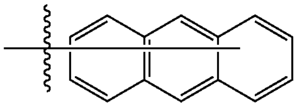

RA6

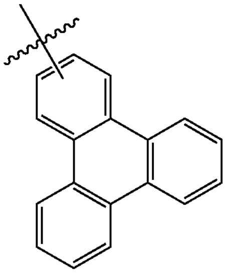

RA7

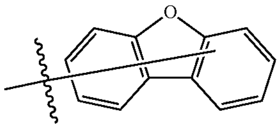

RA8

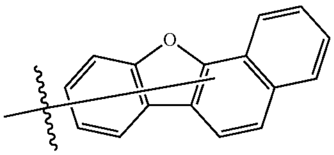

RA9

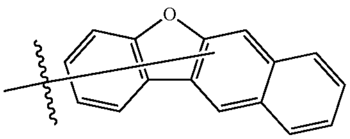

-continued

RA10

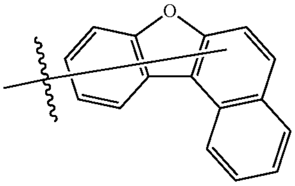

RA11

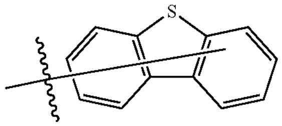

RA12

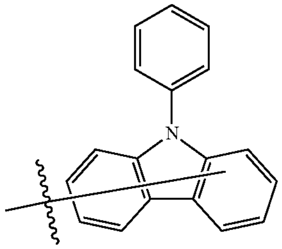

RA13

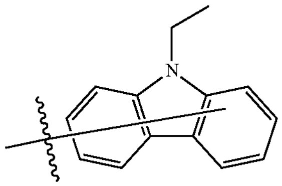

RA14

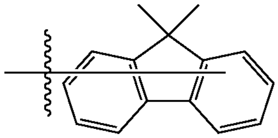

RA15

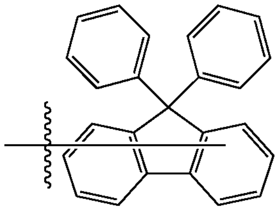

RA16

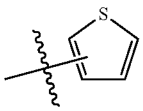

RA17

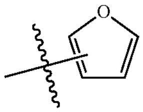

RA18

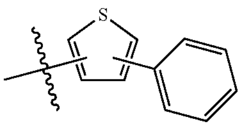

-continued
RA19
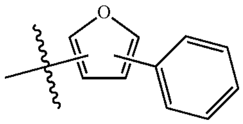
RA20
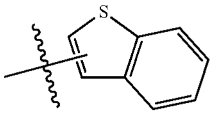
RA21
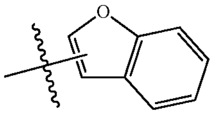
RA22
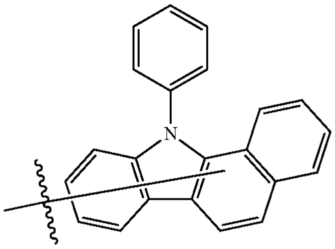
RA23
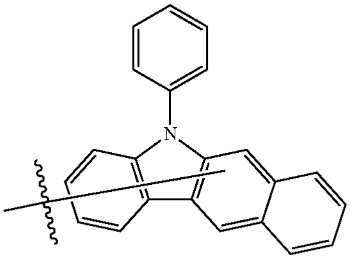
RA24
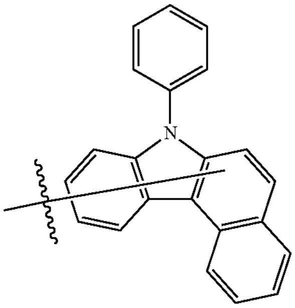
RA25
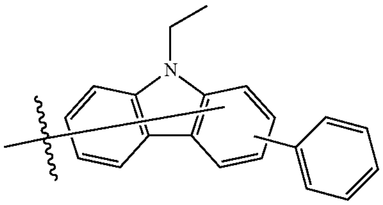
RA26
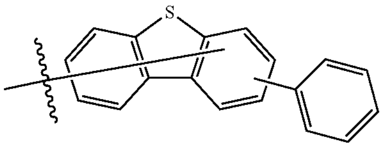
-continued
RA27
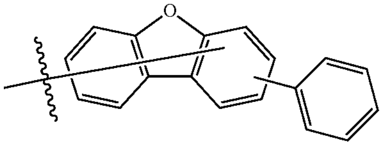
RA28
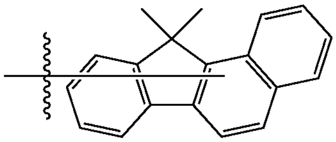
RA29
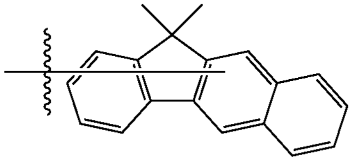
RA30
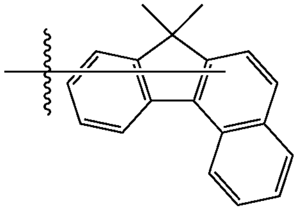
RA31
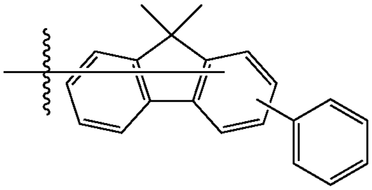
RA32
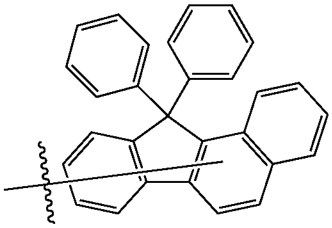
RA33
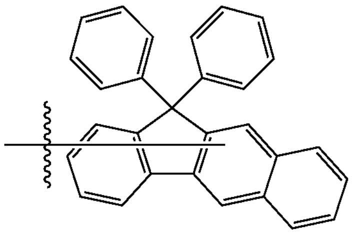

-continued
RA34
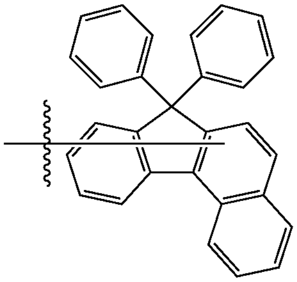
RA35
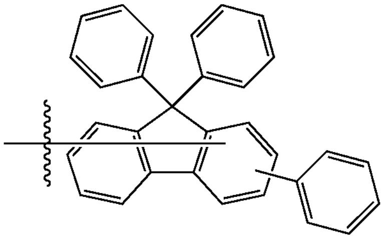
RA36
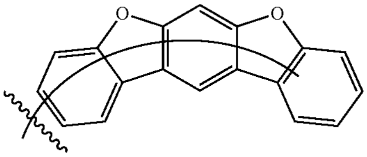
RA37
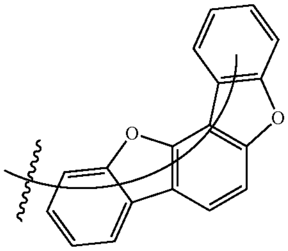
RA38
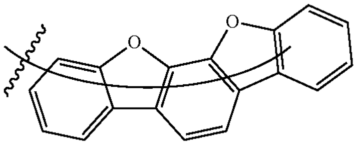
RA39
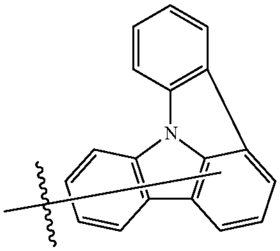
RA40
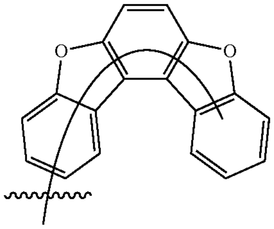
-continued
RA41
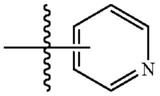
RA42
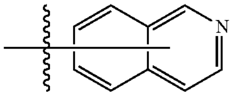
RA43
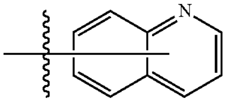
RA44
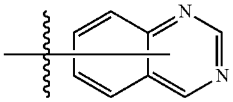
RA45
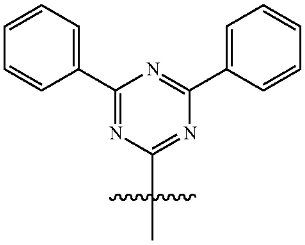
RA46
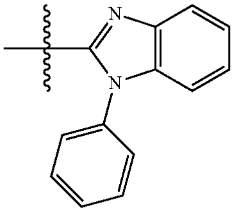
RA47
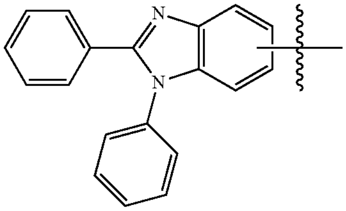
RA48
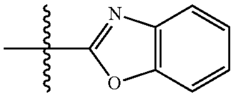
RA49
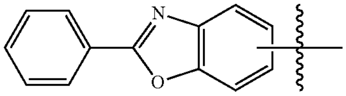
RA50
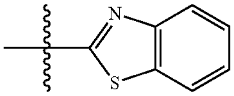
RA51
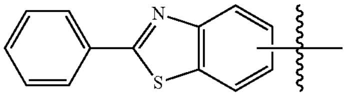

-continued

RA52

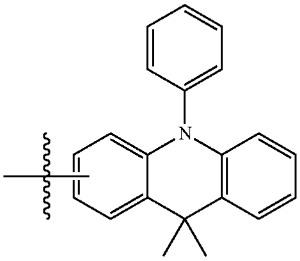

RA53

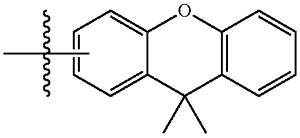

RA54

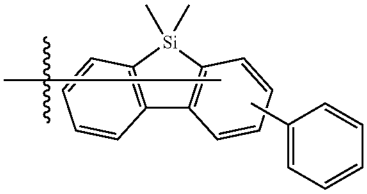

RA55

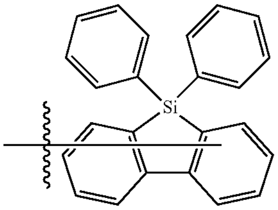

RA56

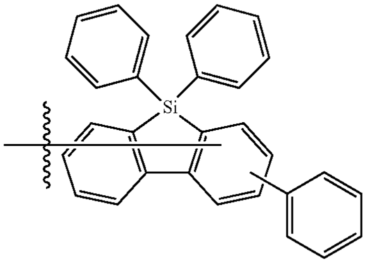

RA57

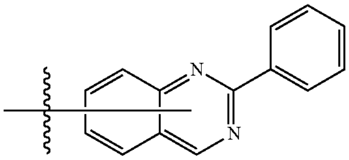

RA58

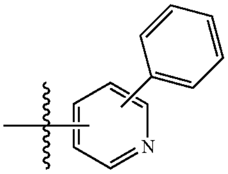

RA59

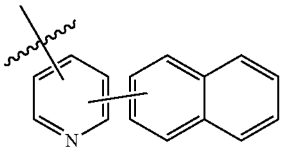

-continued

RA60

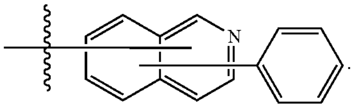

8. The organic electronic device of claim 5, wherein the organic material layer comprises a light emitting layer, and the light emitting layer comprises a compound represented by the following Chemical Formula 1B:

[Chemical Formula 1B]

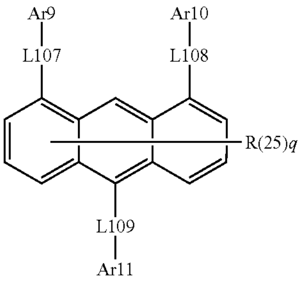

in Chemical Formula 1B,

L107 to L109 are the same as or different from each other, and are each independently a direct bond; a substituted or unsubstituted arylene group; or a substituted or unsubstituted heteroarylene group, Ar9 to Ar11 are the same as or different from each other, and are each independently a substituted or unsubstituted aryl group; or a substituted or unsubstituted heteroaryl group, R25s are the same as or different from each other, and are each independently hydrogen; deuterium; a halogen group; a nitrile group; a nitro group; a substituted or unsubstituted alkyl group; a substituted or unsubstituted cycloalkyl group; a substituted or unsubstituted silyl group; a substituted or unsubstituted phosphine oxide group; a substituted or unsubstituted aryl group; or a substituted or unsubstituted heteroaryl group, q is an integer from 0 to 7, and when q is 2 or more, substituents in the parenthesis are the same as or different from each other.

9. The organic electronic device of claim 8, wherein L107 to L109 are the same as or different from each other, and are each independently a direct bond; or selected from the following structures:

LC1

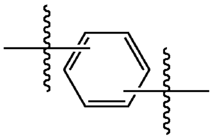

LC2

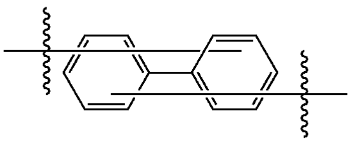

-continued
LC3
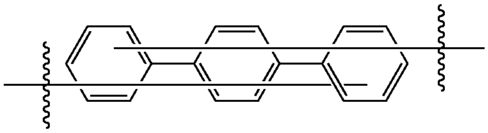
LC4
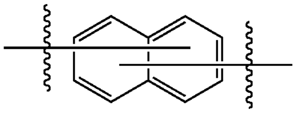
LC5
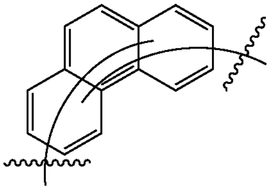
LC6
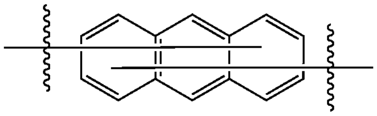
LC7
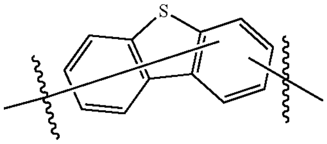
LC8
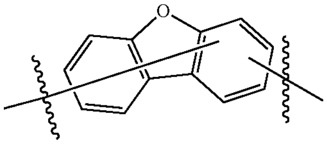
LC9
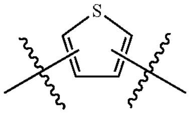
LC10
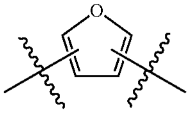
LC11
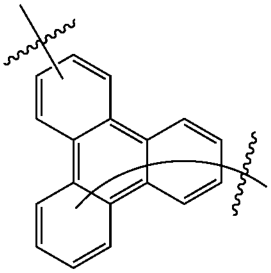
-continued
LC12
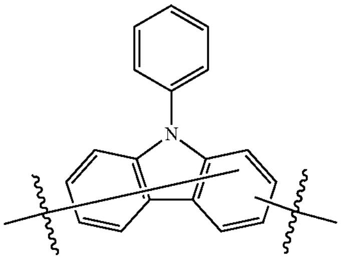
LC13
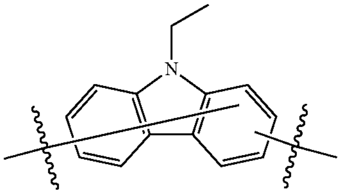
LC14
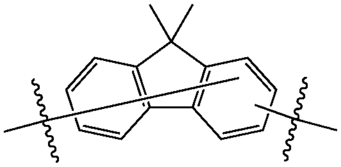
LC15
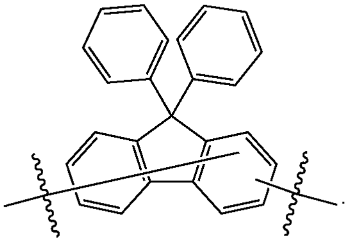
10. The organic electronic device of claim 8, wherein Ar9 to Ar11 are the same as or different from each other, and are each independently selected from the following structures:
RB1
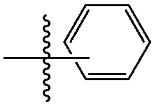
RB2
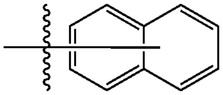
RB3
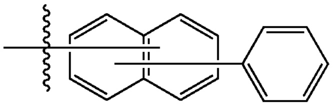
RB4
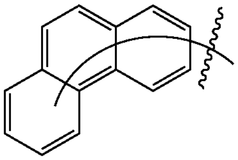

-continued
RB5
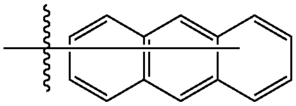
RB6
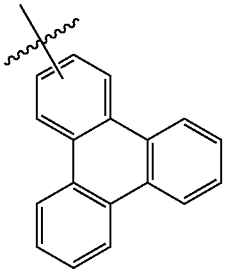
RB7
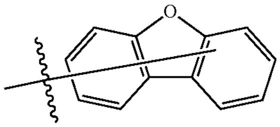
RB8
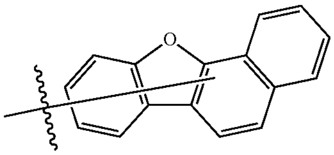
RB9
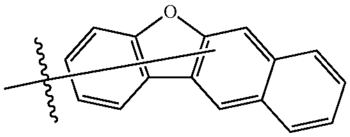
RB10
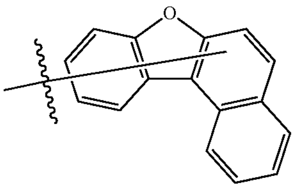
RB11
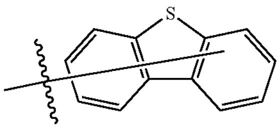
RB12
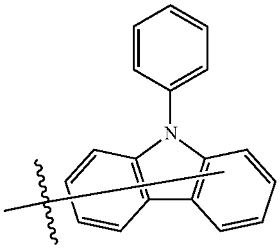
RB13
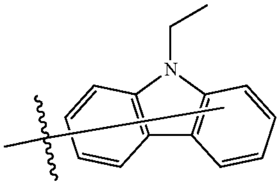
-continued
RB14
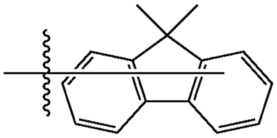
RB15
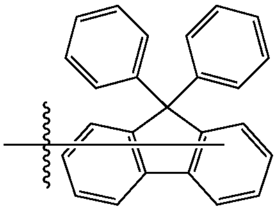
RB16
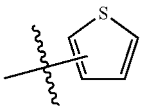
RB17
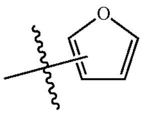
RB18
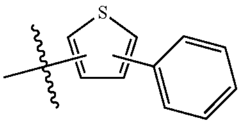
RB19
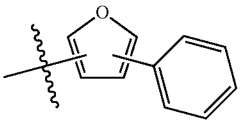
RB20
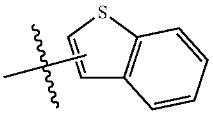
RB21
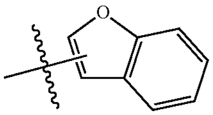
RB22
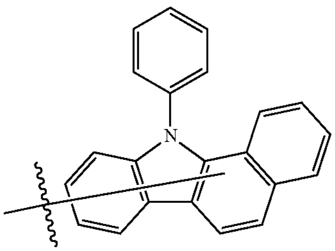

-continued
RB23
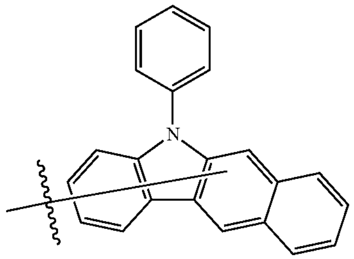
RB24
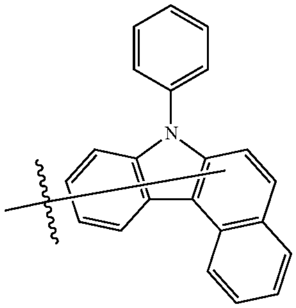
RB25
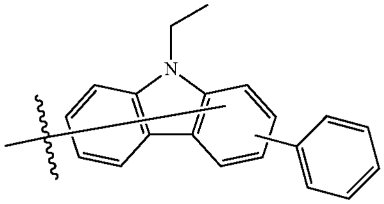
RB26
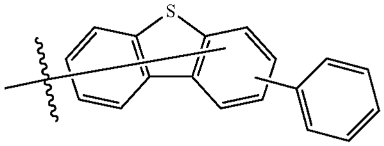
RB27
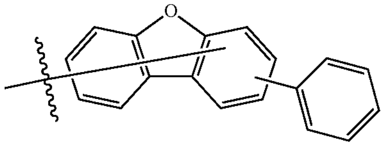
RB28
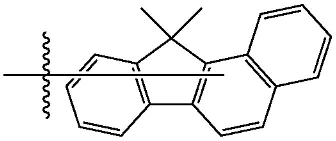
RB29
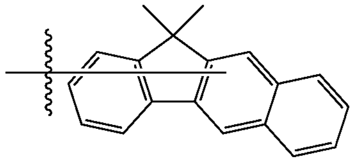
-continued
RB30
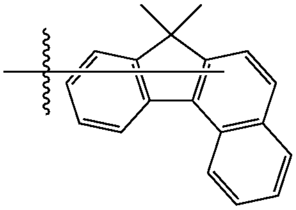
RB31
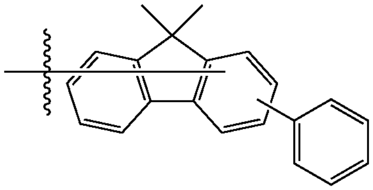
RB32
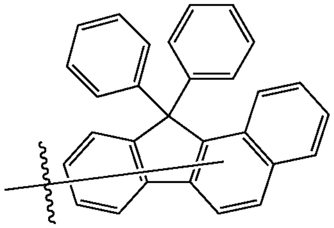
RB33
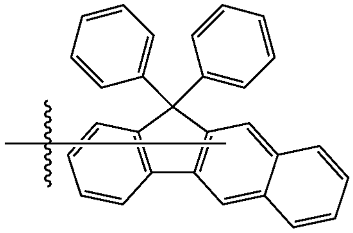
RB34
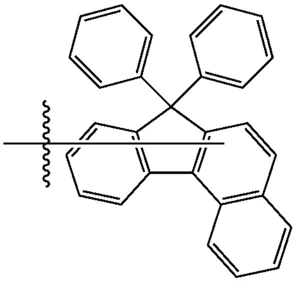
RB35
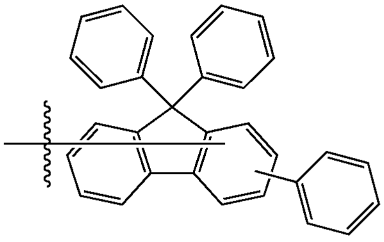
RB36
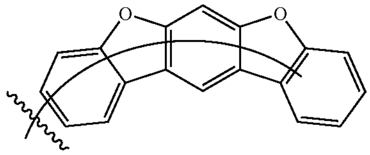

-continued
RB37
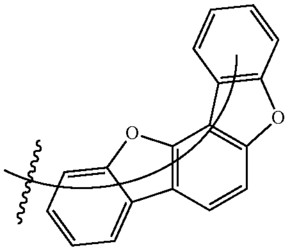
RB38
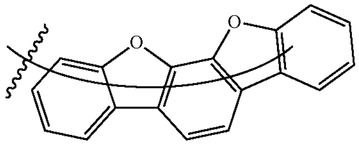
RB39
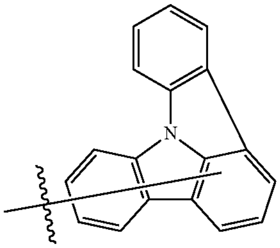
RB40
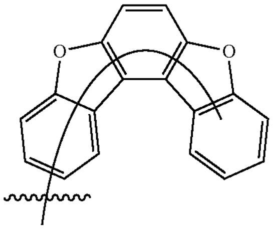
RB41
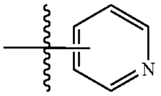
RB42
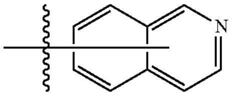
RB43
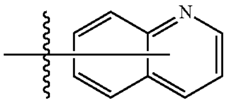
RB44
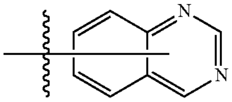
RB45
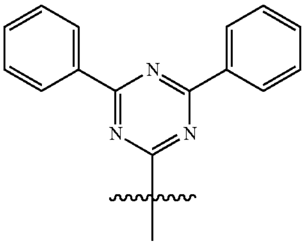
-continued
RB46
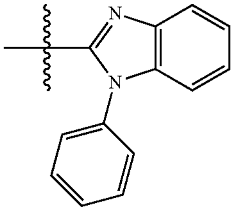
RB47
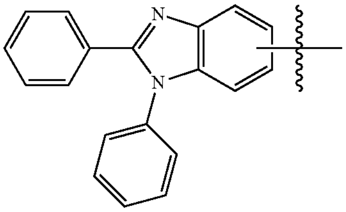
RB48
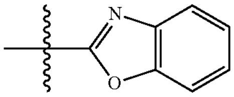
RB49
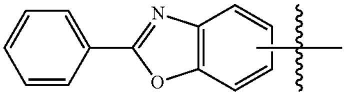
RB50
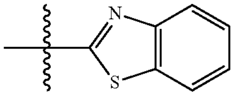
RB51
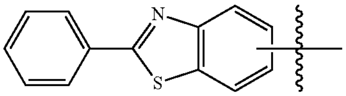
RB52
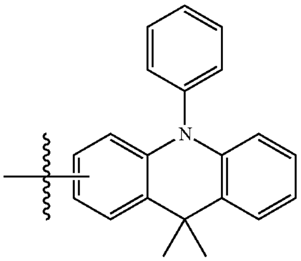
RB53
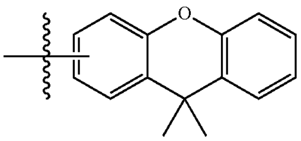
RB54
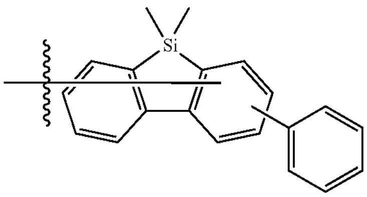

-continued

RB55

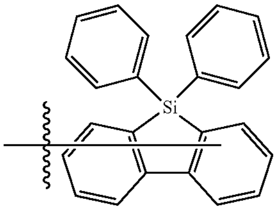

RB56

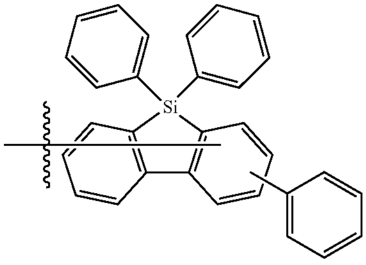

RB57

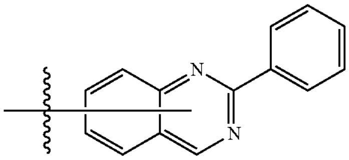

RB58

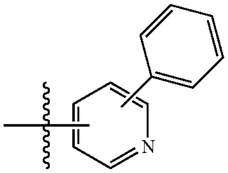

-continued

RB59

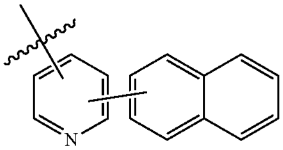

RB60

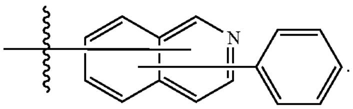

11. The organic electronic device of claim 5, further comprising:

one or two or more layers selected from the group consisting of a light emitting layer, a hole injection layer, a hole transporting layer, an electron injection layer, an electron transporting layer, an electron blocking layer, and a hole blocking layer.

12. The organic electronic device of claim 5, wherein the organic electronic device is selected from the group consisting of an organic light emitting device, an organic phosphorescent device, an organic solar cell, an organic photoconductor (OPC), and an organic transistor.

* * * * *